(12) United States Patent
Waters et al.

(10) Patent No.: US 11,339,407 B2
(45) Date of Patent: May 24, 2022

(54) SYSTEMS AND METHODS FOR POINT/CENTER-OF-CARE IMMUNOTHERAPY

(71) Applicant: Miltenyi Biotec GmbH

(72) Inventors: Timothy Wayne Waters, San Francisco, CA (US); Stefan Miltenyi, Bergish Gladbach (DE); Alexander Scheffold, Cologne (DE)

(73) Assignee: Miltenyi Biotec GmbH, Bergisch Gladbach (DE)

( * ) Notice: Subject to any disclaimer, the term of this patent is extended or adjusted under 35 U.S.C. 154(b) by 710 days.

(21) Appl. No.: 15/663,702

(22) Filed: Jul. 28, 2017

(65) Prior Publication Data
US 2018/0080049 A1    Mar. 22, 2018

Related U.S. Application Data

(63) Continuation-in-part of application No. 15/486,362, filed on Apr. 13, 2017, now Pat. No. 10,273,504, which is a continuation-in-part of application No. 14/351,889, filed as application No. PCT/EP2012/072431 on Nov. 13, 2012, now abandoned.

(30) Foreign Application Priority Data

Nov. 18, 2011   (EP) ..................... 11189754

(51) Int. Cl.
| | |
|---|---|
| *G01N 33/48* | (2006.01) |
| *G01N 33/50* | (2006.01) |
| *C12N 15/87* | (2006.01) |
| *C12N 15/85* | (2006.01) |
| *C12M 1/42* | (2006.01) |
| *G16B 20/00* | (2019.01) |
| *C12M 1/00* | (2006.01) |
| *C12M 3/04* | (2006.01) |
| *C12N 5/0783* | (2010.01) |
| *C12M 1/36* | (2006.01) |

(52) U.S. Cl.
CPC ............ *C12N 15/87* (2013.01); *C12M 23/20* (2013.01); *C12M 27/10* (2013.01); *C12M 35/04* (2013.01); *C12M 35/08* (2013.01); *C12M 41/48* (2013.01); *C12M 45/05* (2013.01); *C12N 5/0636* (2013.01); *C12N 15/85* (2013.01); *G16B 20/00* (2019.02); *C12N 2510/00* (2013.01); *C12N 2525/00* (2013.01)

(58) Field of Classification Search
CPC ...... C12N 15/87; C12N 5/0636; C12N 15/85; C12N 2510/00; C12N 2525/00; C12M 23/20; C12M 27/10; C12M 35/08; C12M 41/48; C12M 45/05; C12M 35/04; G16B 20/00
See application file for complete search history.

(56) References Cited

U.S. PATENT DOCUMENTS

| | | |
|---|---|---|
| 6,867,040 B2 | 3/2005 | Helmstetter |
| 6,977,138 B2 | 12/2005 | Lahann |
| 2008/0255004 A1 | 10/2008 | Neurauter |
| 2009/0186411 A1 | 7/2009 | Hoffman |
| 2010/0143913 A1 | 6/2010 | Strehl |

FOREIGN PATENT DOCUMENTS

| | | |
|---|---|---|
| EP | 1627914 | 2/2006 |
| WO | WO 1995030432 | 11/1995 |
| WO | WO 2008037458 | 4/2008 |
| WO | WO 2009072003 | 6/2009 |

OTHER PUBLICATIONS

Bagnis et al. A genetic strategy to control expression of human blood group antigens in red blood cells generated in vitro. Tranfusion, vol. 49, pp. 967-976. (Year: 2009).*
Anonymous: "Retronectin—Takara," May 7, 2006, URL<https://www.westburg.eu/products/protein-analysis/expression-systems/retroviral-mammalian-expression/retronectin/$13701>, retrieved Jan. 19, 2017.
Galimberti, et al., "Hypergravity speeds up the development of T-lymphocyte motility," Eur. Biophys. J., 2006, 35(5):393-400.
International Search Report and Written Opinion in PCT Appln. No. PCT/EP2012/072431, dated Jan. 7, 2013, 8 pages.
Morbidelli, et al., "Effect of hypergravity on endothelial cell function and gene expression," Microgravity Sci. Technol., 2009, 21:135-140.
Stark, et al., "Organotypic cocultures as skin equivalents: a complex and sophisticated in vitro system," Biological Procedures Online, 2004, 19(4):201-260.
Tonks, et al., "Optimized retroviral transduction protocol which preserves the primitive subpopulation of human hematopoietic cells," Biotechnol. Prog., 2005, 21(3):953-958.
Versari, et al., "Effects of gravity on proliferation and differentiation of adipose tissue-derived stem cells," J. Gravit. Physiol., 2007, 14(1):127-128.

* cited by examiner

*Primary Examiner* — Russell S Negin
(74) *Attorney, Agent, or Firm* — Serge Sira, Esq.; Gregory J. Hwa, Esq.; Fish & Richardson P.C.

(57) ABSTRACT

A cell modification device, comprising a centrifugation chamber with at least one cell modifying surface with a normal vector having an angle of 135-45° to the rotational axis of the centrifugation chamber, wherein the centrifugation chamber comprises at least one input/output port and the cells to be modified are immobilized at the cell modifying surfaces by the rotation of the centrifugation chamber at 2 to 2000 g. In an embodiment, the device is used as a point-of-care and/or portable device. Further, the present disclosure describes software that, when executed by a processor, causes the device to perform the disclosed functions.

21 Claims, 17 Drawing Sheets

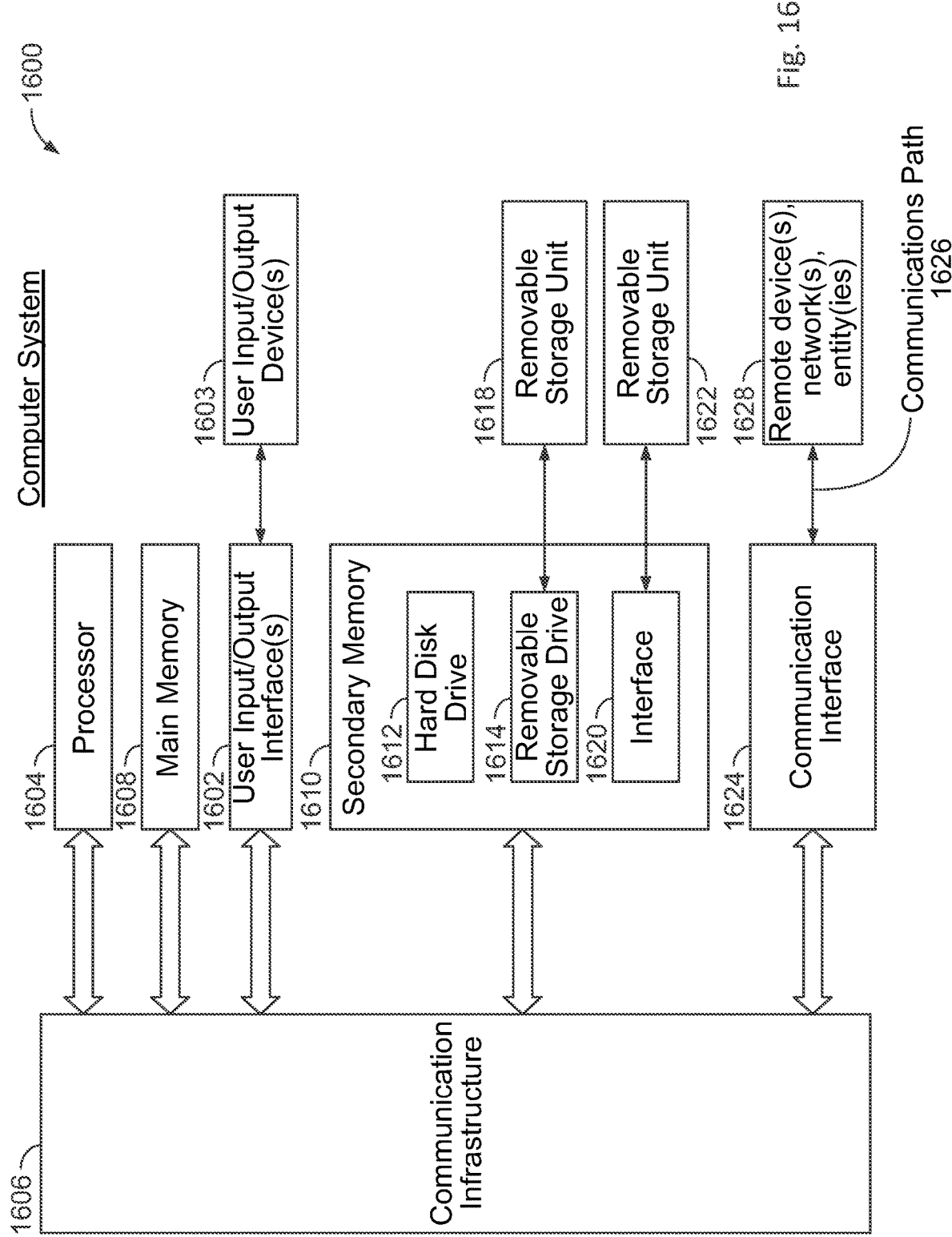

SYSTEMS AND METHODS FOR POINT/CENTER-OF-CARE IMMUNOTHERAPY

CROSS REFERENCE TO RELATED APPLICATIONS

This U.S. Patent Application is a Continuation-in-Part of U.S. patent application Ser. No. 15/486,362 filed on Apr. 13, 2017, which is a Continuation-in-Part of U.S. patent application Ser. No. 14/351,889 filed Apr. 15, 2014, which is a U.S. National Stage application under 35 U.S.C. 371 of PCT/EP2012/072431 filed Nov. 13, 2012, which claims priority to European Patent Application EP 11189754.2, filed Nov. 18, 2011, each of which is hereby incorporated by reference in its entirety.

BACKGROUND

Field

Embodiments of the present invention relate to methods and devices for modifying eukaryotic cells on functionalized surfaces of a centrifugation apparatus.

Background

The conditions during cell culturing have a substantial impact on the phenotypes of the cells and desired or not, cell culturing leads to the manipulation of cells.

Cell culture refers to methods under which eukaryotic cells, especially of mammalian origin, are maintained at appropriate conditions with supply of cell culture medium in a cell incubator or a fermenter. Cell culture conditions vary widely depending on the cell type and the desired application. Variation of cell culture conditions can be utilized for cell expansion, cell differentiation or manufacturing of different phenotypes of the cell type. The most commonly varied factor in culture systems is the cell culture medium, for which a vast number of recipes is known for example "Cell Culture Techniques" Humana Press, 1st. Edition, 2011).

Typically culture systems utilize a large amount of medium compared to the mass of the cells to provide a sufficient reservoir for nutrients. In static systems, the medium covering the cells is limiting the gas diffusion to the cells if the cell culture surface itself does not allow gas diffusion. Slow macroscopic convection of the medium results in uncontrolled and uneven supply of nutrients to the cells and may result in different differentiated i.e. manipulated cells.

Culturing large numbers of cells adhered to a surface without the use of carriers or large volume cell suspension is difficult and requires frequent change of the medium. The known static systems for cell culturing are labor-intensive and need clean room conditions during handling the cell cultures, for example media exchange or transfer cells from and into storing devices or adequate incubators for proper cell growth. In dynamic systems for cell culturing like roller fermenters, cells can dislocate from the surface of the fermenter and are suspended in the media. The conditions for growing and supply of nutrients is not uniform for adhered and suspended cells and will result in different differentiated or modified cells. Centrifugation systems for the separation or modification of cells are known.

It is long known to separate cells from a cell mixture into fractions of different cell types with the aid of centrifugal forces in a centrifuge according to their density i.e. their sedimentation velocity. The cell separation is carried out in a specially designed centrifuge, rotor and container (flask) for the cells. For example, whole blood is fractionated or separated by centrifugation into blood plasma (as upper phase), buffy coat (thin layer of leukocytes mixed with platelets in the middle phase), and erythrocytes as lower phase.

The effect of enhanced gravity generated by centrifugation on cells under culturing conditions has been investigated in various publications. Huang et al (2009) disclose in "Gravity, a regulation factor in the differentiation of rat bone marrow mesenchymal stem cells" in J. Biomed. Here, rBMSCs are first plated on glass coverslips; after 24 h the cells had adhered to the coverslips and the coverslips were transferred to a biocompatible polyethylene culture bag, are incubated with medium and then cultured on a cell centrifuge at 2 g hypergravity for several days. The medium was changed every 3 days during HG/SMG culture.

Gaubin et al. described in Microgravity Sci. Technol. 1991 February; 3(4):246-50 the effects of hypergravity on adherent human cells. Galimberti et al disclose in "Hypergravity speeds up the development of T-lymphocyte motility", Eur Biophys J, May 1, 2006; 35(5): 393-400 a hypergravity cell culture for 1 to 11 days. Cell culture is performed in flasks which were positioned vertically to the centrifugation axis in the centrifuge. The use of flasks within a centrifuge is furthermore proposed by Versati et al in "Effects of gravity on proliferation and differentiation of adipose tissue-derived stem cells", J Gravit Physiol, 14(1): P127-128 (2007). Here, a commercial available medium sized centrifuge (MidiCAR) is used to accommodate cell culture flasks to investigate cell growth under hypergravity conditions. Morbidelli et al. investigated in Microgravity Sci. technol (2009) 21:135-140 the effect of hypergravity on endothelial cell function and gene expression. Cell manipulation or cell modification is not disclosed in this publication.

The methods disclosed in these publications are with the exception of hypergravity conditions nearly identical to common cell culturing and involve manual handling steps like medium change. Change of medium i.e. the supply of cells to be cultured with nutrients involves stopping of the centrifugation process, thereby interruption of the enhanced gravitational forces. Manual handling steps are not only laborious and prone to contamination, but also destroy the micro environment of the cells like cell/cell contact or cell/cell interaction. An unaffected micro environment of the cells is important for cell cultivation, e.g. for the activation of lymphocytes or viral or retroviral transduction processes. There is no disclosure in the prior art about the nature of the surface of the flasks or the centrifugation chamber.

It is further known that retroviral transduction of cells can be accelerated by hypergravity, for example described by Tonks et al in Biotechnol Prog. 2005 21(3): 953-8. With this technique, retrovirus vectors are coated on plates and cells are brought into contact with the virus. In order to promote the contact between target cells and the virus vector, the plate comprising adhered virus and cells are placed into a centrifuge. This requires manual handling steps and the cells are not supplied with medium during centrifugation.

WO 2009/072003 discloses a centrifugation system for cell proliferation. Cell manipulation or cell modification is not disclosed in this publication.

Embodiments of the invention provide a novel device and method for modifying cell populations on functionalized cell modifying surfaces under hypergravity conditions generated by the rotation of a centrifugation chamber. With a device and method in accordance with an embodiment of the invention, eukaryotic cells can be modified and/or eukaryotic cells with new or modified features can be generated.

SUMMARY

It is a first object of an embodiment of the invention to provide a cell modification device, comprising a centrifugation chamber with at least one cell modifying surface with a normal vector having an angle of 135–45° to the rotational axis of the centrifugation chamber, wherein the centrifugation chamber comprises at least one input/output port and the cells to be modified are immobilized at the cell modifying surfaces by the rotation of the centrifugation chamber at 2 to 2000 g.

A device according to an embodiment of the invention comprises a centrifugation chamber with at least one input/output port through which cells, cell culturing liquids (media), gases and other materials can enter and leave the chamber without the need of stopping the rotation of the centrifugation chamber. The device comprises preferable one input port and one output port for liquids and at least one, especially two for gases.

Another object according to an embodiment of the invention is a method for modifying cells comprising the steps
  introducing cells in a cell modification device, comprising a centrifugation chamber with at least one cell modifying surface with a normal vector having an angle of 135–45° to the rotational axis of the centrifugation chamber wherein and comprising at least one input/output port,
  immobilizing the cells on the cell modifying surfaces by the rotation of the centrifugation chamber at 2 to 2000 g
  maintaining the rotation of the rotation of the centrifugation chamber until the cells are modified.

Cell modification according to an embodiment of the invention relates to all methods where cells are kept physiologically active and are modified. The modification may result for example in a change of the phenotype, function, number or differentiation status of the cells, like
  a) cell division, differentiation or cell proliferation
  b) activation of a signal transduction cascade
  c) change of the cellular activation status and/or cell function
  d) genetic modification of cells
  e) growing of layers of different or identical cell types involving cell-cell contact.

The modification of the cells results for example in a change of expression of certain proteins, of RNA molecules, of miRNA, in a change of post translational modification, in a change of DNA methylation or in histone modification.

The cell modification device comprises cell modifying surfaces which can be functionalized for cell modification.

The mechanical/chemical stimulus changing the phenotypes of the cells is provided or triggered by the functionalized cell modifying surfaces of the centrifugation chamber of an embodiment of the invention. The term "functionalized surface" as used in this application includes all types of surfaces which can provide a stimulus to a cell. Typically, functionalized cell modifying surface comprise a coating of chemical or physical immobilized bioactive compounds, like
  proteins, peptides, nucleic acids;
  spacer molecules enhancing the adhesion of cells or bioactive compounds to the cell modifying surfaces like hydrophilic polymers (functionalized poly lactate, polyvinyl alcohols, polysaccharides; functionalized dextrans);
  organic or inorganic particles as carrier of bioactive compounds, especially magnetic particles coated with functionalized poly lactate, poly vinyl alcohols or functionalized dextrans;
  substances enhancing cell adhesion, e.g. polypeptides, lipids, polysaccharides;
  viruses and retroviruses or particles thereof
  cells which can be used for modification of a target cell, such as antigen presenting cells, "accessory cells" producing certain bioactive factors or cell lines transfected with certain functional molecules.
  stimulus provided by mitogens, cytokines, stimulatory antibodies or receptor ligands The cell modification device according to an embodiment of the invention comprises at least one cell modifying surface which is functionalized for example for adherence, proliferation, genetic and/or cellular modification of the cells, or for proliferation of cells in one or more layers.

The cell modification device according to an embodiment of the invention comprises preferable at least one cell modifying surface which is functionalized with at least one substance enhancing proliferation of cells, and/or inducing genetic modification and/or inducing cellular modification of cells. The cell modifying surface can further be functionalized with particles being functionalized with at least one substance enhancing proliferation of cells, and/or inducing genetic modification and/or inducing cellular modification of cells.

Surface Functionalization with Cell Binding Systems

In a first embodiment of the invention, the cell modifying surfaces may be functionalized with any substance which is suitable for cell culture and useful or required to introduce preferable cell culture conditions for a given cell type.

The cell modifying surfaces can be functionalized in order to enhance adherence and/or proliferation of cells on the cell modifying surfaces. Suitable substances for functionalization of the surfaces are glycoproteins, polypeptides, glycosaminoglycans, disaccharides, biotin binding molecules or protein tags. For example, the surface may be coated with extracellular matrix proteins including all collagen types (I to VIII).

Furthermore, the cell modifying surfaces may comprise an affinity binding system. One of the most widely used affinity binding system is the avidin-biotin or streptavidin-biotin system. For example, the cell modifying surface may be first coated with avidin and/or streptavidin (or derivatives thereof) to facilitate binding of a biotinylated molecule like a biotinylated antibody. It is furthermore possible to coat the cell modifying surface first with biotin (or derivatives thereof) to facilitate binding of another molecule functionalized with streptavidin and/or avidin. Both variants result in high affinity binding of the second molecule to the cell modifying surfaces. The strong interaction between streptavidin or avidin-biotin is made much weaker by using a combination of modified streptavidin or avidin and modified biotin like desthiobiotin or a derivative thereof like DSB-X Biotin (Hirsch et al. 2002: "Easily reversible desthiobiotin binding to streptavidin, avidin, and other biotin-binding proteins: uses for protein labeling, detection, and isolation". Analytical Biochemistry 308: 343-357; US2008/0255004A1). A protein, such as an antibody may be biotinylated With the modified biotin. When this protein is immobilized by binding the modified biotin to an optionally modified streptavidin or avidin molecule bound to the cell modifying surface, it may be released under mild conditions by adding free biotin.

The functionalizing of the cell modifying surface like coating with biotin or (strept)avidin may be performed before or during a process according to an embodiment of the invention, both inside or outside of the centrifugation chamber or a device according to an embodiment of the invention. The renewal of the coating or the functionalization of the cell modifying surface may be performed between two process steps and without interruption of the rotation of the centrifugation chamber. For example, the renewal of the functionalized cell modifying surface is possible by adding biotinylated molecules or molecules with (strept)avidin to a cell modifying surface which is coated with streptavidin or biotin, respectively.

Further affinity binding systems suitable for the cell modifying surfaces comprise antibodies, for example antibodies against biotin or protein tags for example IIsopeptago, BCCP or Myc-tag.

The cell modifying surfaces may be further be coated with libraries of substances synthesized with methods of combinatorial chemistry in order to identify substances which work best as binding system for a given cell type.

Certain bioactive polymers may be used as spacer molecules enhancing the adhesion of cells or the binding of other substances on the cell modifying surfaces like functionalized poly lactic acid, polyvinyl alcohols, polysaccharides or dextrans or derivatives thereof. This binding system is especially useful as basic coating of a cell modifying surface produced from a hydrophobic plastic material like poly carbonate, polystyrene or polyethylene. The cell modifying surfaces may be coated with highly reactive polymers as e.g. disclosed in U.S. Pat. No. 6,977,138B2.

The cell modifying surfaces can comprise one or more substances which enhance adhesion and/or proliferation of cells. Especially useful are one or more substances selected from the group consisting of collagen types (I to VIII), fibronectin, gelatin, laminin, elastin, hyaluronic acid, keratan sulfate, chondroitin sulfate, heparan sulfate proteoglycans, poly-d-lysine, avidin, streptavidin, biotin, antibodies, antibodies against biotin or protein tags, protein tags like IIsopeptag, BCCP, Myc-tag, Calmodulin-tag, FLAG-tag, HA-tag, His-tag, Maltose binding protein-tag, Nus-tag, Glutathione-S-transferase-tag. Green fluorescent protein-tag, Thioredoxin-tag, S-tag, Softag 1, Softag 3, Strep-tag, SBP-tag, Ty tag, certia, poly lactate, polyvinyl alcohols, polysaccharides and dextran.

Surface Functionalization for Cellular Modification

In a second embodiment of the method of invention, cell modification comprises cellular modification like activation, proliferation, dedifferentiation and/or differentiation of cells. Accordingly, the cell modifying surfaces may be functionalized with any substance which is suitable for cellular modification of cells like cell activation, proliferation, dedifferentiation and differentiation of cells. The cell modifying surface can further be functionalized with particles being functionalized with at least one substance suitable for cellular modification of cells like cell activation, proliferation, dedifferentiation and differentiation of cells.

In particular, cell modification by a method and device of an embodiment of the invention comprises the alteration of gene expression, protein expression, post-translational or posttranscriptional modifications of genes, mRNAs or proteins, protein phosphorylation, histone modification, or modification of intracellular signaling cascades (e.g. $Ca^{2+}$ influx).

Furthermore, cellular modification may comprise cell activation for example by agonistic or antagonistic antibodies, cytokines, growth factors, (de-)activating ligands, pharmacologically active substances, mitogens, DNA or RNA-modifying substances.

The cell modifying surfaces can be functionalized for one or more cellular modification steps, Surface Functionalization for Genetic Modification In a third embodiment of the invention, the cell modifying surfaces may be functionalized with any substance which is suitable for genetic modification of cells, i.e. modification of cells using genetic material or any other substances interacting, binding or integrating into cellular polynucleotides or the genome and/or altering their function. Again, the cell modifying surface can further be functionalized with particles being functionalized with at least one substance suitable for genetic modification of cells, i.e. modification of cells using genetic material or any other substances interacting, binding or integrating into cellular polynucleotides or the genome and/or altering their function.

Genetic modification of a cell according to this invention includes for example transduction by viral, such as adenoviral or retroviral or lentiviral vectors or transfection with nucleic acids, i.e. coding RNAs, non-coding small or large RNAs (i.e. siRNA, miRNA, shRNA), DNA, mRNA- or snRNA-epression plasmids or other substances interacting or binding or integrating into cellular polynucleotides or the genome and/or altering their function.

Genetic modification furthermore comprises contacting the cells for example with a virus, viral particle, RNA, DNA, protein, ligand, receptor, cytokine, stimulating or deactivating antibody, pharmacological agent, other cells (e.g. feeder cells) or layers of several cells or cell types. The contacting agent can be soluble in the cell culturing liquid or attached to the cell modifying surfaces, or can be expressed or anchored to the surface of another cell used for co-culture.

The cell modifying surfaces can be functionalized for one or more genetic modification steps.

Surface Fractionalization for Cell Layers

Culturing cells on flat cell modifying surfaces often results in two-dimensional sheets, which is an artificial environment for any cell. Eukaryotic cells experience in vivo a three-dimensional environment and are surrounded by other cells, membranes, fibrous layers and adhesion proteins. Three-dimensional cell cultures are known and use as support extracellular matrices, scaffolds and proteins to provide an in vivo-like morphology and physiologically relevant environment. Commercially available 3D cell culture systems are e.g. MaxGel™ human Extracellular Matrix (ECM), HydroMatrix™ synthetic peptide, and mouse ECM, from Sigma® to support stem cell and other cell cultures.

A fourth object according to an embodiment of the invention is to provide a layered cell composition, wherein cells are grown in a layered system like tissue or organs. For this purpose, a device and method in accordance with an embodiment of the invention is used to immobilize cells at defined positions, e.g. in successive layers of same or different cell types, and to keep the cells at a fixed position by the centrifugal forces, allowing building of complex layers, in addition to be grown in a layered system, the cells may further be modified as described above.

The cell modifying surfaces of a device according to an embodiment of the invention can comprise one or a plurality of identical or different functionalized cell modifying surfaces. For example, the cell modifying surfaces can be equipped with an affinity binding system in addition to functionalization of the surface for genetic modification of the cells.

Processing Modules and/or Software

Embodiments of the system described herein include a computer control system or unit providing monitoring and/or control of one or more aspects of the system. The computer control system can include one or more processing modules or systems to process information (e.g., flow information, etc.) within the system and can include a wide variety of proprietary and/or commercially available computers, components or electronics having one or more processing structures and the like, with such systems comprising data processing hardware and/or software configured to implement any one or a combination of operations as described herein. Each control software module, when executed by a processor of the device, causes the device to perform the various functionality as described herein.

BRIEF DESCRIPTION OF THE DRAWINGS/FIGURES

The accompanying drawings, which are incorporated herein and form a part of the specification, illustrate embodiments of the present disclosure and, together with the description, further serve to explain the principles of the disclosure and to enable a person skilled in the pertinent art to make and use the embodiments.

Figure 8:
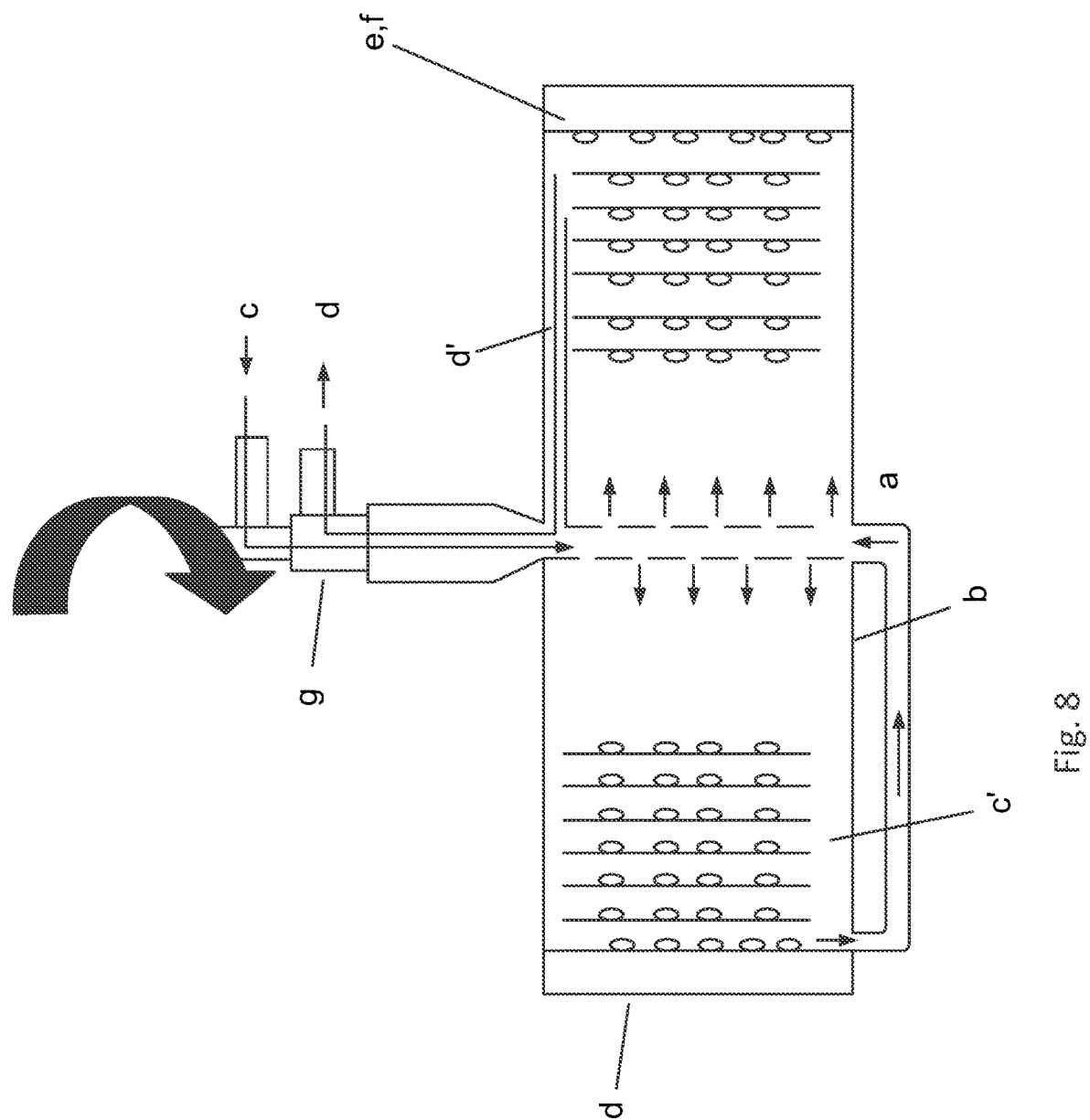

FIG. 8 shows an embodiment in which the cell modifying surfaces (e) are not or not throughout connected to the second cell modifying surface f) and the top cover of the chamber, thereby allowing a flow of cell culturing liquid and gases via tubing or channels c' and d'. Optionally tubing or channel d' comprises apertures for distribution of the cell culturing liquid and gases over the cell modifying surfaces (e).

Figure 9:
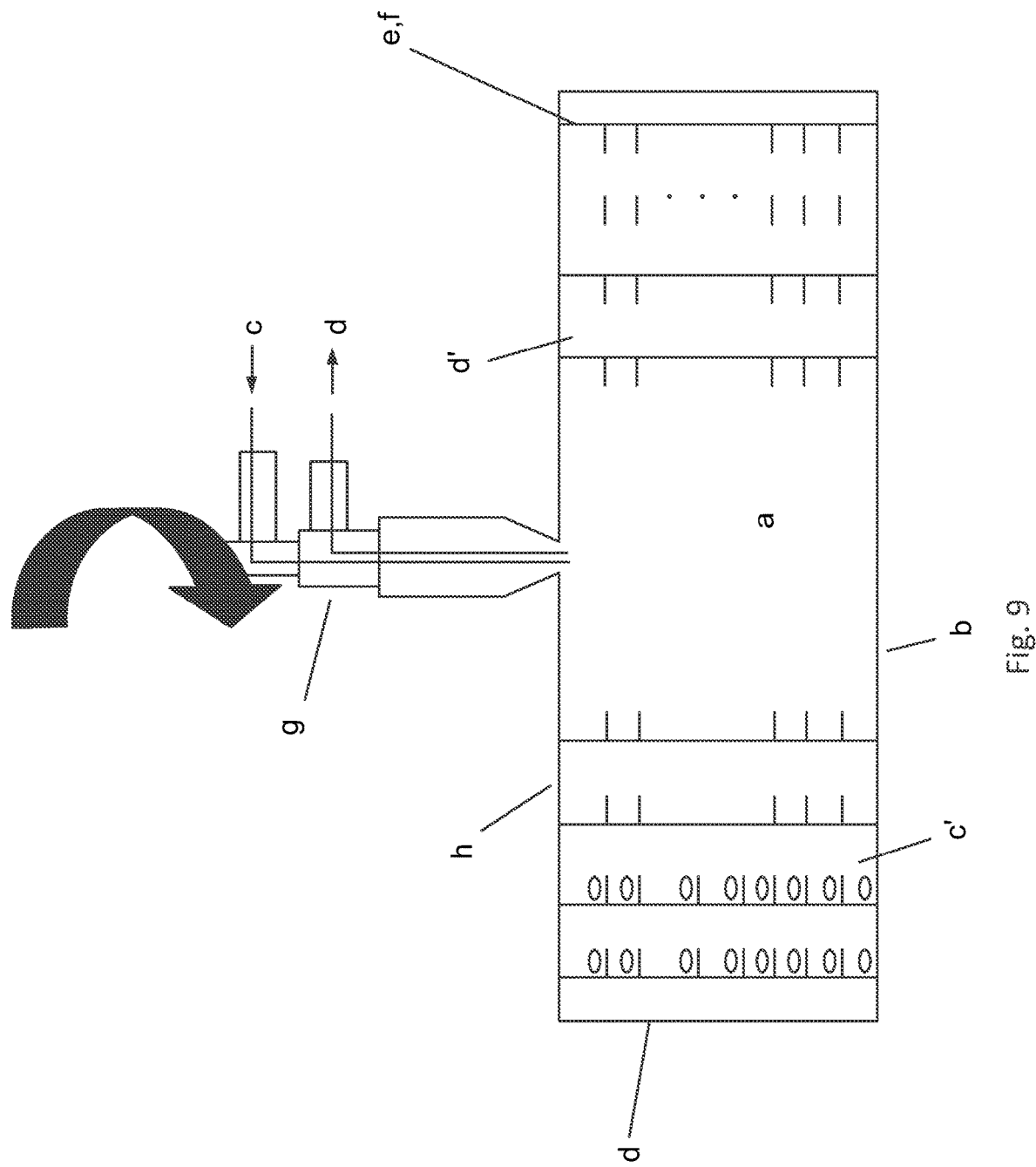

FIG. 9 shows an embodiment in which concentric or spiral-shaped cell modifying surfaces (f) with a normal vector having an angle of 135–45° (shown 90°) to the rotational axis of the centrifugation chamber and second cell modifying surface (h) with a normal vector having an angle of (−45)–45° (shown 0°) to the rotational axis of the centrifugation chamber are combined.

Figure 10:
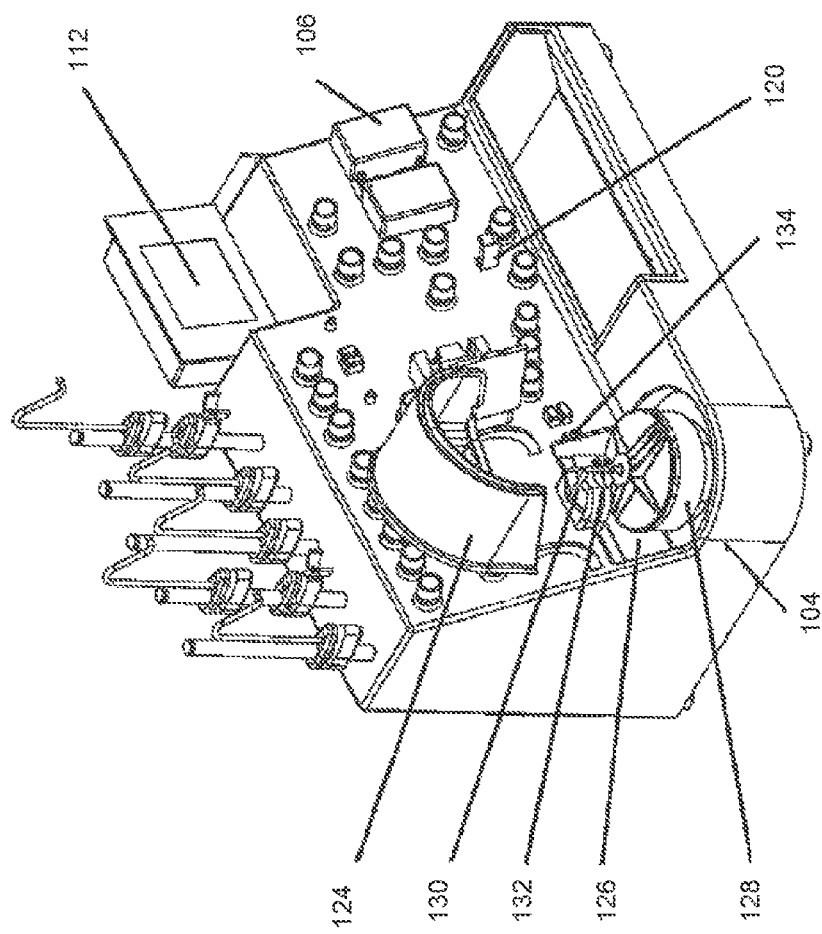

FIG. 10 is a system level drawing illustrating a portable, point of care device in accordance with embodiments described herein.

Figure 11B:
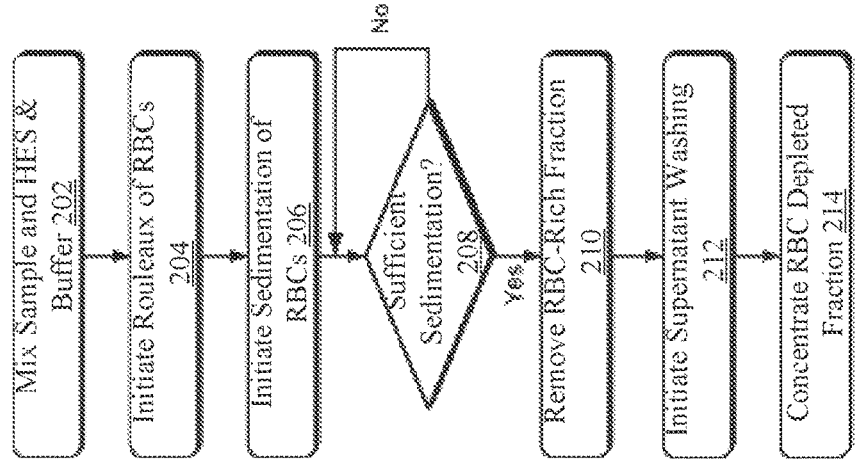
Figure 11A:
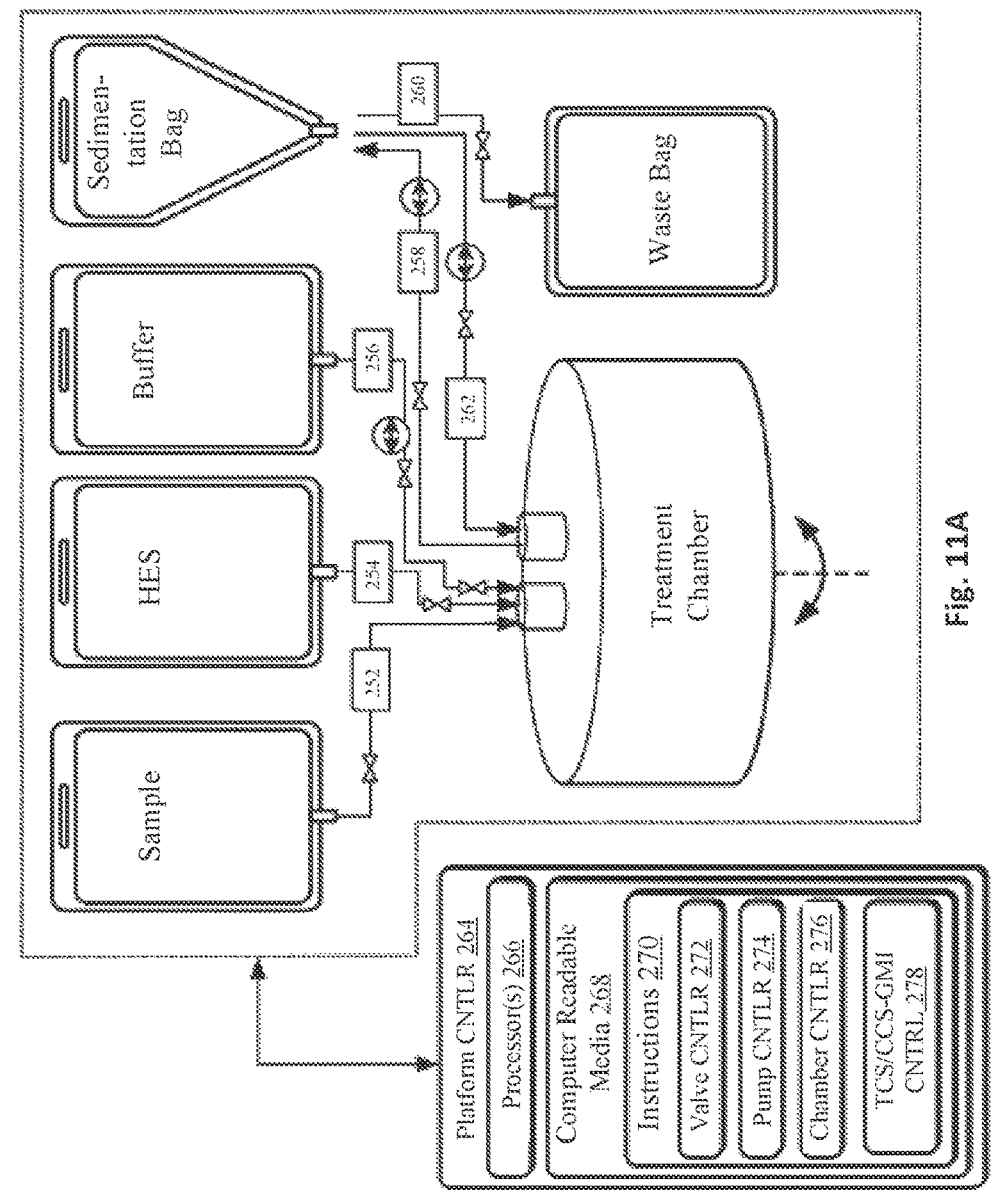
Figure 11C:
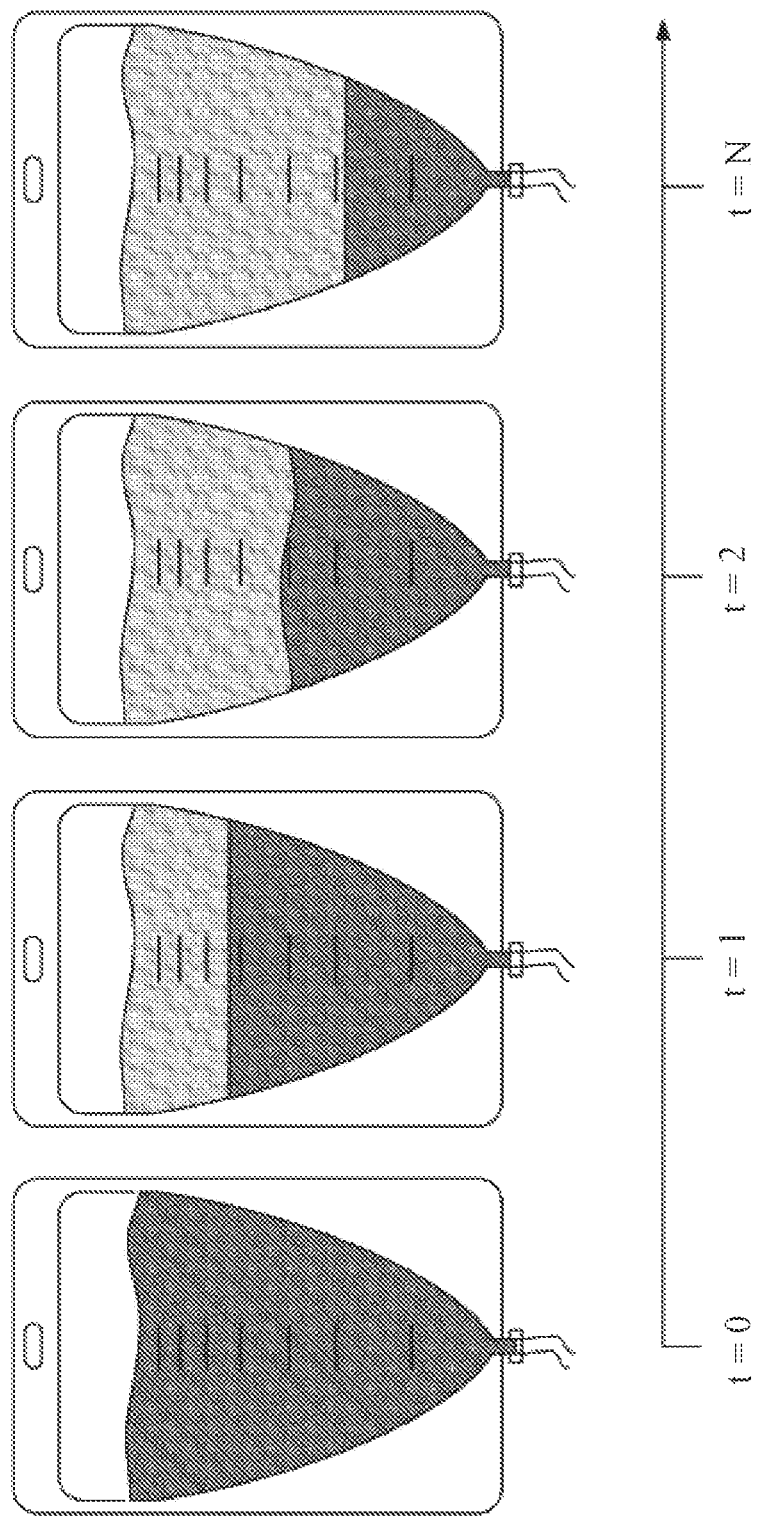

FIG. 11A shows a schematic diagram of an exemplary system for depleting red blood cells (RBCs) from a sample. FIG. 11B is a flow chart of an exemplary method for depleting RBCs using the exemplary system of FIG. 11A. FIG. 11C illustrates a funnel shaped sedimentation bag with a sample having undergone RBC Rouleau. As illustrated, the RBCs concentrate into an increasingly dense sediment as time progresses.

Figures 12A, 12B:
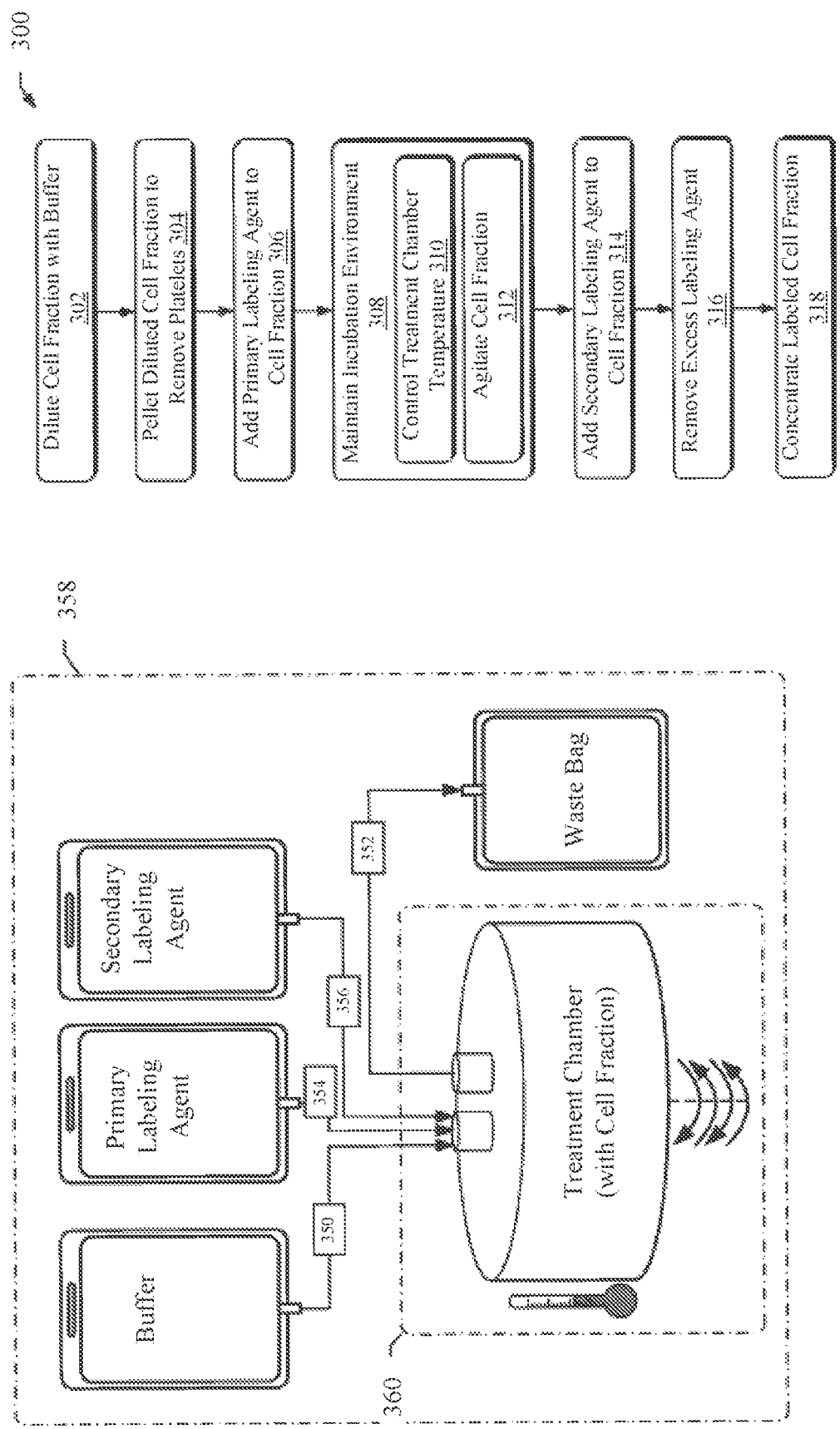

FIG. 12A shows a schematic diagram of an exemplary system for preparing (e.g. labeling and/or maintaining the health of) target cells of a sample for later selection/isolation of the target cells. FIG. 12B is a flow chart of an exemplary method for preparing target cells using the exemplary system of FIG. 12A.

Figure 13B:
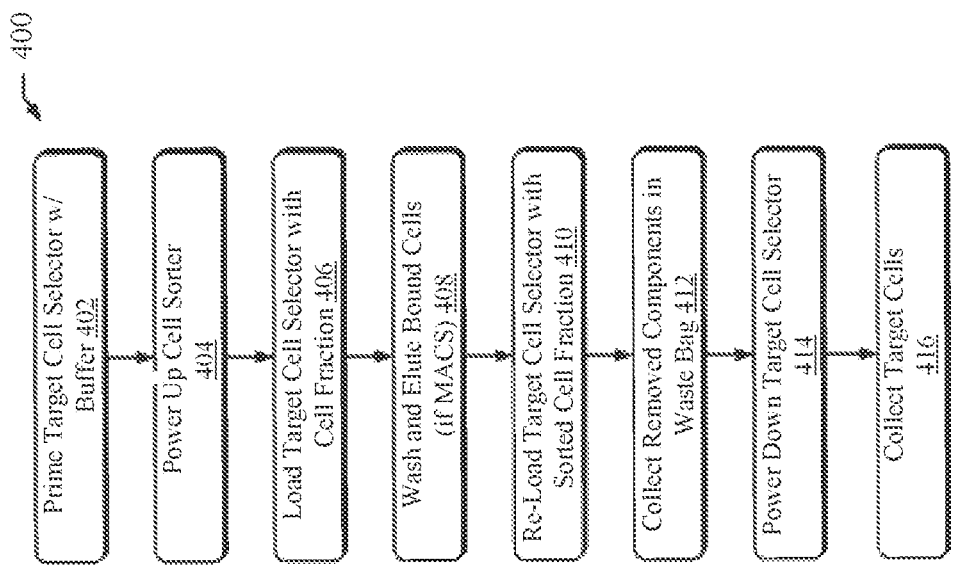
Figure 13A:
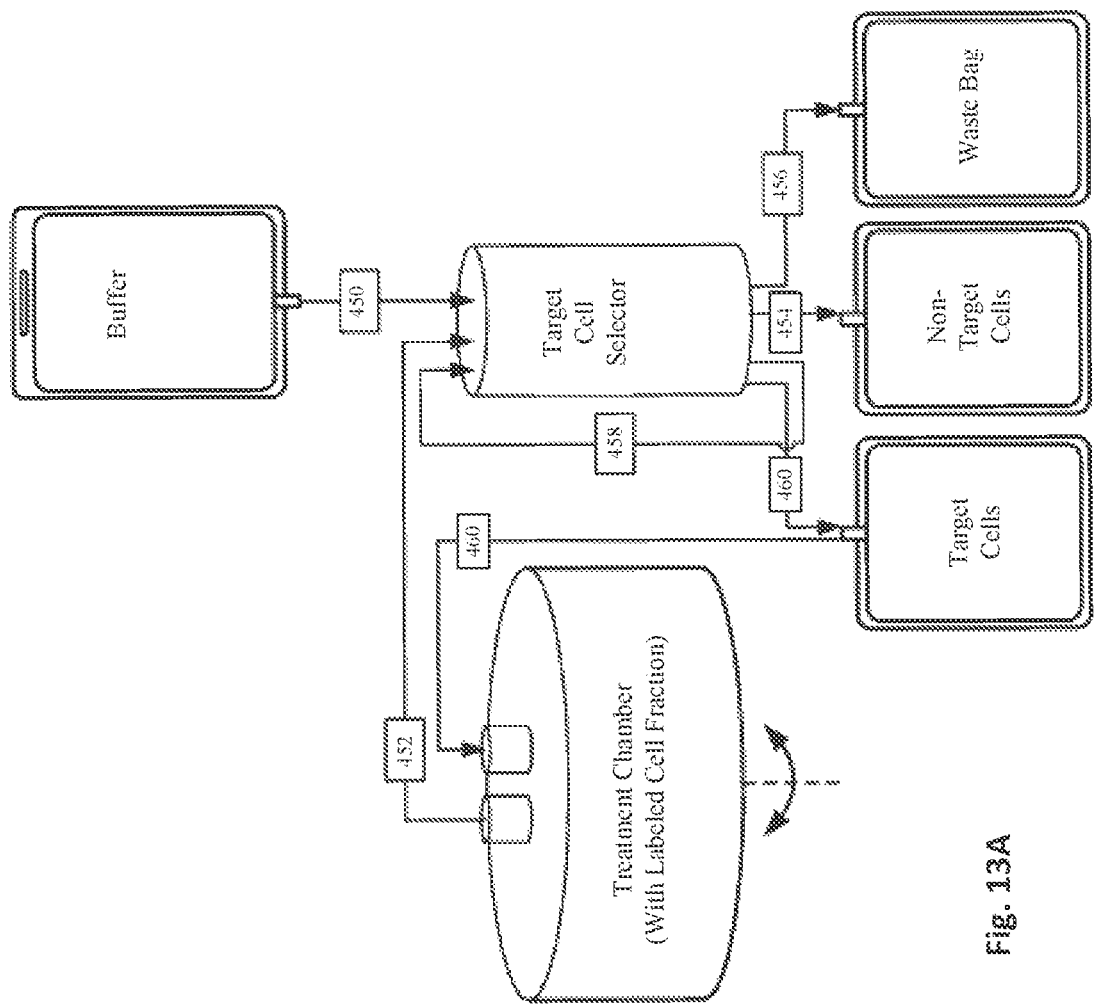

FIG. 13A shows a schematic diagram of an exemplary system for selection/isolation of target cells. FIG. 13B is a flow chart of an exemplary method for selecting/isolating target cells using the exemplary system of FIG. 13A.

Figure 14B:
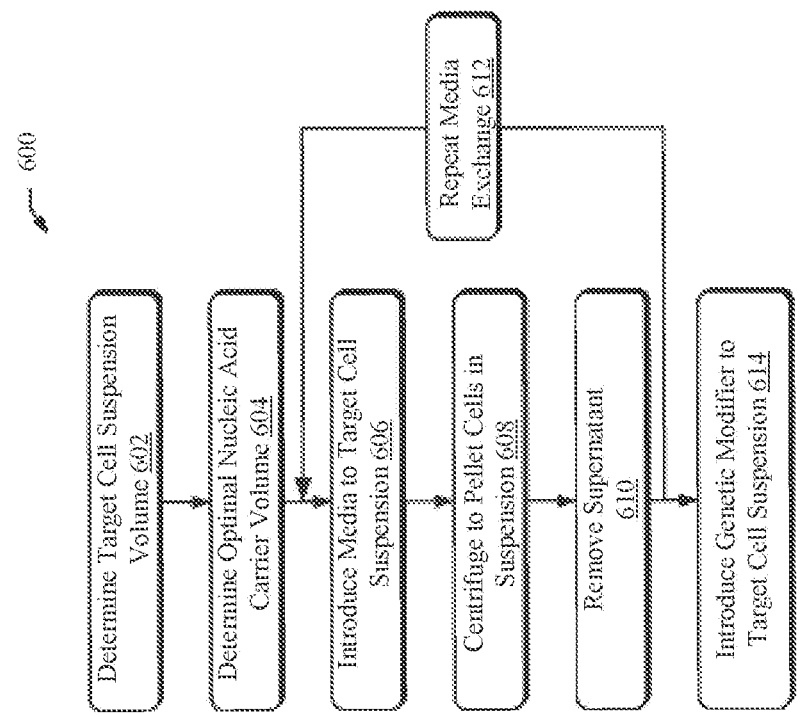
Figure 14A:
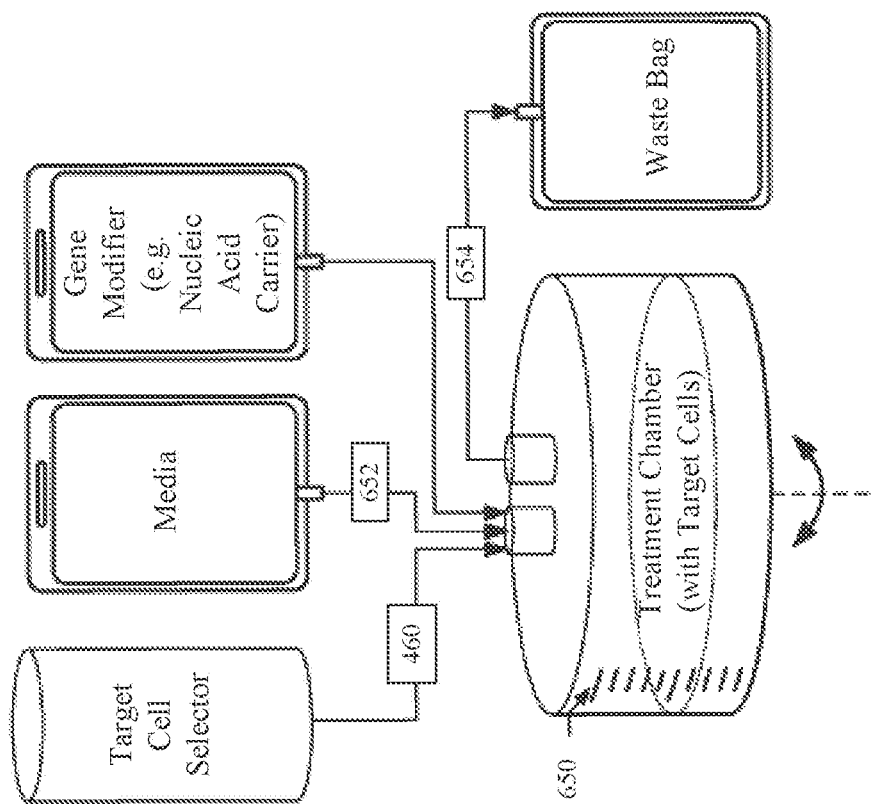

FIG. 14A shows a schematic diagram of an exemplary system for introducing genetic modifiers to target cells to facilitate gene-modification thereof. FIG. 14B is a flow chart of an exemplary method for introducing genetic modifications to the selected target cells using the exemplary system of FIG. 14A.

Figure 15B:
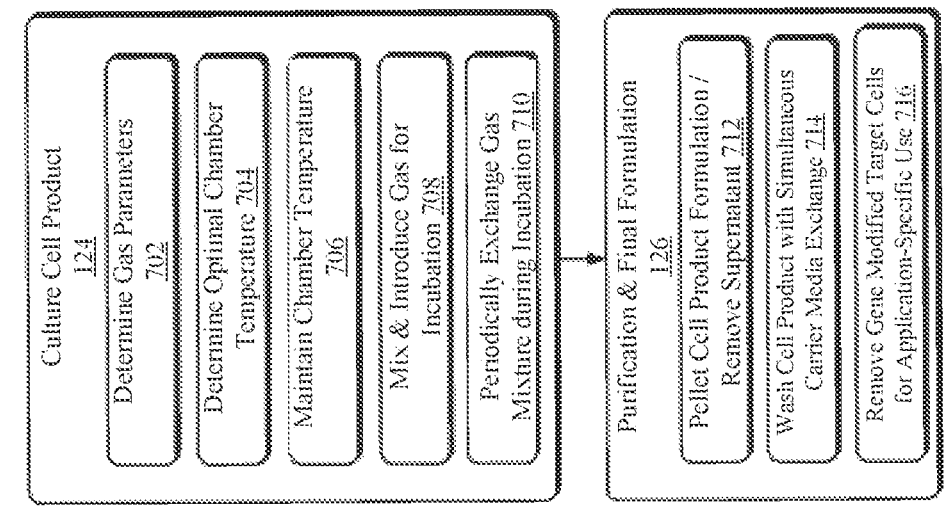
Figure 15A:
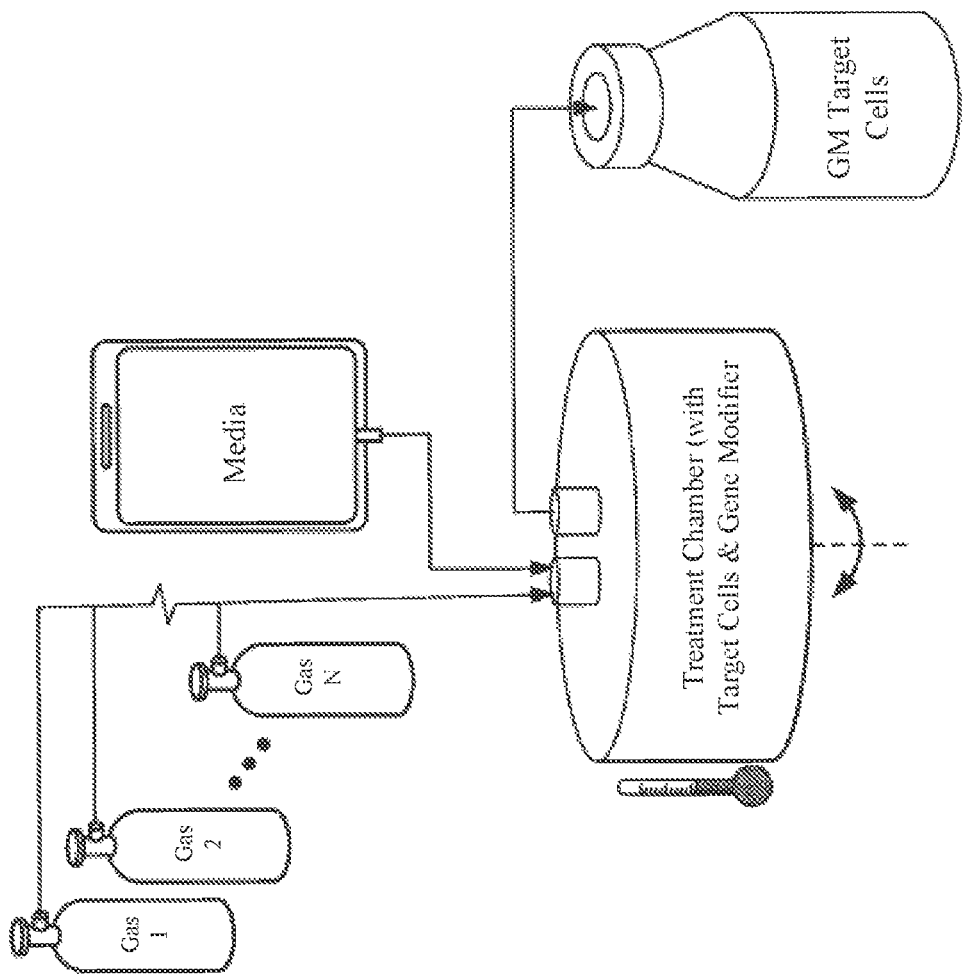

FIG. 15A shows a schematic diagram of an exemplary system for culturing, purifying, and formulating gene-modified cells for application-specific use, e.g. administering the gene-modified cells to a subject. FIG. 15B is a flow chart of an exemplary method for culturing, purifying, and formulating the gene-modified cells using the exemplary system of FIG. 15A.

FIG. 16 shows an example computer system for practicing embodiments of the invention.

DETAILED DESCRIPTION

In general, cell modification according to one or more embodiments of the invention involves cell culturing conditions where cells are kept physiologically active over a period of time. This is usually accomplished at temperatures of 25-45° C. and with a supply of nutrients like glucose and gases like $O_2$ and $CO_2$. During the culturing process, the conditions can be maintained stable or are subject to changes such as hyper/hypoxia conditions, increased/decreased pressure, different gravitational forces, increased/decreased supply of nutrients or growth factors, increased/decreased temperature, high or low cell density, increased/decreased medium osmolarity, or gradients of nutrients, chemokines/cytokines/growth factors or stimulatory/deactivating antibodies.

Cell Media

In a method according to an embodiment of the invention, various cell culturing liquid (media) known in the art of cell culturing can be used as stimulus for cells, including one or more of the following media DMEM, HBSS, DPBS, RPMI, Iscove's medium, X-VIVO™, each optionally supplemented e.g. with fetal calf serum, human serum or serum substitutes or other nutrients or cell stimuli like Cytokines. The media can be standard cell media like the above mentioned media or special media for e.g. primary human cell culture (e.g. for endothelia cells, hepatocytes or keratinocytes) or stem cells (e.g. dendritic cell maturation, hematopoietic expansion, keratinocytes, mesenchymal stem cells or T cell expansion). The media may have supplements or reagents well known in the art, e.g. albumins and transport proteins, amino acids and vitamins, antibiotics, attachments factors, growth factors and cytokines, hormones or solubilising agents. Various media are commercially available e. g. from Life Technologies or Sigma-Aldrich.

Centrifugation Conditions

During cell modification in a device and method according to an embodiment of the invention, the cells to be modified are immobilized at the cell modifying surfaces by the gravitational forces due to the rotation of the centrifugation chamber.

An embodiment of the invention is preferably carried out at a rotational speed of the centrifugation chamber generating centrifugal forces of more than 1 g and up to 2000 g, preferable between 20 and 1000 g, more preferable between 20 and 500 g and especially preferable between 20 and 100 g.

The degree of cell modification can be adjusted by the speed of rotation of the centrifugation chamber, since the gravitational forces enacting on the cells depend on the speed of the centrifugation chamber, density of the culturing media, density of the cells and the distance of an individual cell to the rotational axis of the centrifligation chamber.

The magnitude of centrifugal forces F acting on a given cell depends on the mass m of the cell, its speed, i.e. its angular velocity $\omega$, and the radius r of curvature, i.e. the distance between the cell and the rotational axis of the chamber, according to the following formula:

$$F = m \, r \omega^2$$

The mass m of the cell is calculated from the cell volume ($V_{cell}$) and the cell density ($\delta_{cell}$). Cell density $\delta_{cell}$ of eukaryotic cells is between 1.04 and 1.09 g/cm$^3$. Taking into account the buoyant force relative to the media density ($\delta_{media}$), the centrifugal force F can be calculated as follows:

$$F = (\delta_{cell} - \delta_{media}) V_{cell} \, r \, \omega^2$$

The angular velocity can be expressed as rotations of the chamber per time (2 $\pi$T). If an individual cell is located at the inner wall of the chamber, r equals the inner radius of the chamber.

The degree of interaction between surface and cell may be modified changing the density of the medium. Typically, media density ($\delta_{media}$) is around 1.0 g/cm$^3$, but can be changed by appropriated additives. Accordingly, cells can be released during a process of an embodiment of the invention from the cell modifying surfaces by utilizing a cell medium with a higher density or enhancing the density of the cell medium by adding appropriated additives.

Cell modification according to an embodiment of the invention involves centrifugation conditions applied to the cells as long as necessary to induce the desired modification of the cells. The duration of the centrifugal forces depends on the desired modification of the cells and is not limited. Centrifugal forces may be applied to the cells during the process of an embodiment of the invention for as short as 10 s or as long as 10 days. Typically, centrifugal forces of more than 2 g, especially more than 5 g or more than 10 g are applied for at least 40, 120 or 360 minutes up to 720 minutes.

It is also possible to maintain centrifugation at the same speed during the entire process or to use a sequence of several (2-50) periods of centrifugal forces with same or different speed of rotation. The duration of the centralgal forces may vary, depending on the desired modification of the cells. For example, the speed of rotation may be higher if a process step for genetic and/or cellular modifications of cells is involved compared to rotational speed during steps for culturing and/or expanding the cells. The continuous flow of liquid through the centrifugation chamber and/or over the cell modifying surfaces can be achieved through variation of the centrifugal forces i.e. through a variation of speeds of rotation of the chamber.

Use of Particles

Modification of cells with the device and method according to an embodiment of the invention may further comprise the use of particles, especially particles having functionalized (i.e. biologically active) surfaces. The particles may be produced from organic material like polymers (poly dextrines, poly saccarides, poly styrene, poly lactides or poly vinyl alcohol, each chemically modified or unmodified) or inorganic material like silica, alumina or ferromagnetic metals or metal oxides. Particles made from inorganic material may be coated with the polymers mentioned. The size of the particles depends on their intended function and may vary between 20 nm and 500 µm.

Preferable, the particles are coated or at least doped with biologically active substances. The biologically active substances may be mixed with the bulk material of the particle and can be released during the process of an embodiment of the invention. In another variant, the biologically active substances are only present on the outer surface of the particles.

The particles may contain or be coated with all biologically active substances already disclosed in the present application for surface functionalization for cell layers, surface functionalization with cell binding systems, surface functionalization for cellular modification or surface functionalization for genetic modification.

Particles may be coated or immobilized by the centrifugal forces on the cell modifying surfaces before introducing the cells to be modified into the centrifugation chamber. In this case, the cells are immobilized by the centrifugal forces on the particles. In another variant or method according to an embodiment of the invention, first the cells to be modified are immobilized by the centrifugal forces on the cell modifying surfaces. Then, the particles are introduced into the centrifugation chamber, for example as suspension in the cell media. In this variant, the particles are immobilized by the centrifugal forces on the cells.

The particles and/or biologically active substances are brought into close contact with the cells to be modified with the aid of the centrifugal forces exerted on the cell membrane of the cells. Depending on the centrifugal forces exerted on the cell membrane of the cells, it is even possible that the particles and/or biologically active substances are introduced into the cells. Substances which transiently permeabilize the cell membrane can be added to assist this process.

Particles can be used in any process step of embodiments of the invention, alone or in addition to other disclosed biologically active substances or coatings.

Sequence of Processing Steps

In another embodiment, the cells are subjected to a sequence of at least two different gravitational forces i.e. rotational speeds of the centrifugation chamber. In this embodiment, at least two different process steps can be performed, each with a rotational speed adapted for the respective process step.

A sequence of same or different centrifugal forces applied on the cells (i.e. rotational speed of the centrifugation chamber) allows the control of the kind or the degree of cell modification. For example, the cells can be genetically modified by transducing with virus particles in a first processing step at a rotational speed generating centrifugal forces of 100 g to 1000 g and thereafter cultured/expanded in a second processing step at a rotational speed generating centrifugal forces of 2 g to 100 g.

A method according to an embodiment of the invention can comprise a sequence of processing steps consisting of at least two centrifugation steps with the same or different centrifugal forces applied which are optionally interrupted by for example the change or renewal of the cell modifying surfaces or culturing media, or the addition of stimulating substances or cells. The exchange or renewal of any material can be performed during a process according to an embodiment of the invention without opening the centrifugation chamber.

For example, a method according to an embodiment of the invention can comprise a sequence of processing steps, wherein cells are first introduced into the chamber and immobilized at the functionalized cultural surfaces by the rotation of the centrifugation chamber. After a first modification, like a proliferation step, the cells are rinsed at low rotational speed of the chamber from the cell modifying surfaces into a buffer container via the inlet/outlet port. Then, the centrifugation chamber may be stopped and a new (same or different) coating may be applied to the cell modifying surfaces. In an alternative variant according to an embodiment of the invention, the rotation of the chamber is not stopped, and the cell modifying surfaces are coated with the same (fresh) or a different functionalized coating under ongoing rotation of the chamber. An affinity binding system as disclosed above may be used for a recoating step.

After the cell modifying surfaces are replaced or recoated, the cells are reintroduced from the buffer container into the centrifugation chamber and the next modification step under centrifugation conditions can be performed.

In a further example for a sequence of processing steps during the process according to an embodiment of the invention, the cell modifying surface may first be coated e.g. with BD Primaria™ to enhance the proliferation of the cells and then with virus particles for one or more transduction steps. The cell modifying surface may be recoated with new (same or different) virus particles between two transduction processes. For functionalizing the cell modifying surface with virus particles, the cells are rinsed from the surfaces and stored in a buffer container. After the coating process, the cells are reintroduced into the centrifugation chamber and the second culturing step can be started.

Batch and Continuous Modification

A centrifugation chamber and method according to an embodiment of the invention permit both the batch-wise and the continuous modification of cells. In a batch-wise modification, the cells either stay during the whole process within the chamber or are completely removed and after an intermediate step reintroduced into the chamber. Batch processing involves usually an intermediate storage of cells in a buffer container.

Continuous modification means that the cells are continuously introduced into and removed from the chamber during the modification process. Continuous modification involves e.g. a conical shaped centrifugation chamber or cell modifying surfaces and/or a flow of media through the chamber which transports cells as required. For continuous modification, the centrifugation chamber comprises at least two inlet/outlet ports for liquids and gases and optionally an intermediate storage of cells in a buffer container.

Introducing the cells in the chamber, rinsing cells into a buffer container, washing and coating of the cell modifying surfaces and reintroducing the cells into the chamber can be performed with the aid of pumps and tubes and controlled e.g. by appropriate software.

Supply of Nutrients and Overall Conditions

Temperature and gas composition of the centrifugation chamber can be controlled and adjusted if appropriate for the cell types or the modification steps to be performed. For this purpose, a heating and/or cooling means can be attached to the device in an embodiment of the invention.

In a method according to an embodiment of the invention, it is preferred to cover the cells to be modified with a layer of liquid (media) as thin as possible to supply the cells with gases such as $O_2$, $N_2$ and $CO_2$ by diffusion. The thinner the film, the easier diffusion of gases and the better cells can be supplied. Therefore in another variant in accordance with an embodiment of the invention, the cell culturing liquid is moved over or relative to the cells e.g. by changes of the rotational speed or by adding additional media through the ports. Preferable, the liquid media is moved over the cells during rotation of the chamber in form of a liquid film with a thickness of less than 50 µm, less than 100 µm, less than 200 µm, less than 500 µm, less than 1000 µm or less than 2000 µm. Films of cell culturing liquids having such thickness are sufficient to cover and supply the cells with the necessary nutrients and gases. The cells may be supplied with cell culturing liquids by constant movement of the liquid relative to the cells.

In another variant in accordance with an embodiment of the invention, the cell culturing liquids are exchanged or renewed during the modification process in a constant flow. For this variant, a device according to an embodiment of the invention has at least two ports for inlet/outlet of cell culturing liquid. The exchange of liquids can be performed without stopping the rotation of the centrifugation chamber.

The cell culturing liquid (media) supplied to the cells may have the same composition during the entire modification process. It is furthermore possible to change the composition of the media during the modification process, for example by withdrawing a first medium and supplying a second medium from/to the chamber or by a constant flow of medium with a constant change of composition.

Cells to be Modified

The eukaryotic cells modified in a device and/or method according to an embodiment of the invention may originate from any mammalian or human source, such as a tumor, blood, tissue, bone marrow or cell lines, for example one or more cell types selected from the group consisting of human cells, fibroblasts, embryonic stem cells, keratinocytes, melanocytes, mesenchymal stem cells, epithelial cells, T-cells, regulatory T-cells, B-cells, NK-cells, neuronal cells, dendritic cells, stem cells (adult, embryonic, hemapoietic), cells originating from epithelium, ectoderm, endoderm, endothelium, mesoderm, epithelial tissue, basal lamina, vasculature, connective tissue, fibrous tissues, muscle tissue, visceral or smooth muscle, skeletal muscle, cardiac muscle, nervous tissue, brain, spinal cord, cranial nerves, spinal nerves or motor neurons.

A method and device in accordance with an embodiment of the invention are especially suitable for modification of eukaryotic cells, preferable for modification of one or more cell types selected from the group of human blood and immune system cells consisting of Megakaryocyte (platelet precursor), Monocyte, Connective tissue macrophage (various types), Epidermal Langerhans cell, Osteoclast (in bone), Dendritic cell; lymphoid tissues), Microglial cell (in central nervous system), Neutrophil granulocyte, Eosinophil granulocyte, Basophil granulocyte, Mast cell, Helper T cell, Suppressor T cell, Cytotoxic T cell, Natural Killer T cell, B cell, Natural killer cell, Reticulocyte, Stem cells and committed progenitors for the blood and immune system (various types), and tissue or tumor stem cells.

According to a method of an embodiment of the invention at least two different cell types or cells of at least two different phenotypes can be modified.

The cells exhibit a different phenotype after modification. It is a further object of an embodiment of the invention to provide a cell composition modified by a method according to an embodiment of the invention. Yet another object of an embodiment of the invention is to provide a cell composition with at least two layers, the layers comprising modified cells of different cell types or cells of a different phenotype.

Modification Techniques

It is an advantage of a cell culturing device and method according to an embodiment of the invention that the cells are pressed against the cell modifying surfaces by the centrifugal forces, thereby enlarging the cell surface adjacent to the functionalized cell modifying surfaces. Enlarging the cell surface enhances the chances of contact between for example a target cell to be modified and a feeder cell or a retrovirus.

Furthermore, the centrifugal forces bring the functionalized cultural surfaces in close contact with the membrane of the cells to be modified. The close contact causes the cell to act for example by signal transduction or uptake of the extracellular material into the cell. Modification techniques during a method according to an embodiment of the invention may comprise genetic or cellular modification of the cells or the preparation of cellular layers.

Genetic Modification

The term "genetic modification of cells" refers to all processes manipulating the genetic program of a cell on the level of DNA, RNA or translation of RNA into proteins by introduction of oligo- and/or polynucleotides into the genetic material of the cell. The transfected material may be only transiently expressed, e.g. in form of plasmids within the cell, or the transfected material may be stably expressed by integration of the genetic material into the genome of the cell. Genetic modification during a method according to an embodiment of the invention comprises all techniques of molecular cloning and transformation to alter the structure and characteristics of the genes of a cell to be modified. This may include using recombinant nucleic acid (DNA or RNA) techniques to form new combinations of heritable genetic material followed by the incorporation of such material into the cell.

A process according to an embodiment of the invention may comprise various methods of introducing foreign nucleic acids into a eukaryotic cell, which are known to the skilled artisan.

Such methods include applying physical treatment, like, for example, applying nanoparticles or magnetofection, using chemical materials like cyclodextrin or cationic polymers such as DEAE-dextran or polyethylenirnine or using biological particles (viruses) that are used as carriers.

Genetic modification of cells within a method according to an embodiment of the invention comprises furthermore the use of genetic modifying agents resulting in a genetic modification of the cell. Such genetic modifying agents are nucleic acids, e.g. DNA or RNA. The nucleic acid may be naked or in complexes with carrier molecules such as polymers, liposomes, or microparticles. The DNA may be in linear form (oligonucleotides, polynucleotides) or in circularized form (e.g. DNA-plasmids). The RNA may be any kind of RNA known to exist in the cell (e.g. mRNA, miRNA, siRNA, shRNA). The nucleic acid (DNA or RNA) may be derivatives of the naturally occurring nucleic acids or may be chemically modified. For example, modified nucleotides may include: linked nuclear acid (LNA), 2-0-Me nucleotides. 2'-O-methoxyethyl, and T fluoro. Backbone modifications include, for example, phosphorothioate and phosphate.

Another genetic modifying agent is a viral-based gene delivery system which involves genetically engineered recombinant viruses, like, for example, Adenovirus, Adeno-Associated Virus, Retrovirus, Vaccinia virus and Lentivirus, which carry the gene of interest in their capsid.

A genetic modifying agent may also comprise chemical mutagens such as base analogues (e.g. 5-bromouracil (5-BU)) which are incorporated into DNA, agents modifying purines and pyridines or agents labilizing bases (e.g. nitrous oxide, hydroxylamine and alkylating agents) and agents producing distortions in DNA (e.g. flourescent acridine dyes such as proflavine and acridine orange.

Genetic modification of cells within a method according to an embodiment of the invention comprises for example introducing the nucleic acids, e.g. DNA or RNA, into the cell by using the already disclosed particles. The nucleic acid to be introduced into the cell may be covalently or non-covalently attached to the surface of the particles resulting in nucleic acid particle complexes. The nucleic acid particle complex may be immobilized on the cell modifying surface of the centrifugation chamber or the nucleic acid particle complexes may be given into the liquid/media within the centrifugation chamber. Then application of gravitational forces by rotation of the centrifugation chamber of the present invention drives the nucleic acid particle complexes towards and into the target cells, where the cargo is released.

Genetic modification of cells within a method according to an embodiment of the invention comprises for example introducing the nucleic acids, e.g. DNA or RNA, into the cell using chemical-based transfection agents such as e.g. cyclodextrin, polymers, liposomes. The complexes of nucleic acid, e.g. DNA (linear or in circular form, e.g. plasmid) or RNA, and the chemical transfection agents, e.g. Lipofectamin® may be immobilized on the cell modifying surface of the centrifugation chamber. Then application of gravitational forces by rotation of the centrifitgation chamber of the present invention drives the complexes of nucleic acid, e.g. DNA or RNA, and the chemical transfection agents towards and into the target cells. Alternatively, the complexes of nucleic acid, e.g. DNA or RNA, and the chemical transfection agents, e.g. Lipofectamin® may be given into the liquid/media within the centrifugation chamber resulting in transfection of the cell during the centrifugation of the centrifugation chamber.

Genetic modification of cells within a method according to an embodiment of the invention comprises for example introducing the nucleic acids, e.g. DNA or RNA, into the cell using viral-based gene delivery systems (e.g. adenovirus, adeno-associated virus, retrovirus, and lentivirus). The virus or virus particles to be introduced into the cell may be covalently or non-covalently attached to the surface of the cell modifying surface of the centrifugation chamber or the virus or virus particles may be given into the liquid/media of the centrifugation chamber. Then application of gravitational forces by rotation of the centrifugation chamber of the present invention drives the virus or virus particles towards and into the target cells.

In some embodiments of the invention, cell modifying surfaces are optionally coated with affinity binding systems i.e. peptides enhancing retroviral transduction like for example, RetroNectin® (Takara, Japan). The multivalent nature of such affinity binding systems allows the simultaneous binding of cells and viruses, bringing the two into close physical proximity. The co-localization of viruses and cells facilitates infection, resulting in higher frequencies of stable gene transfer. Affinity binding systems may furthermore be coated on particles, which results in a co-localization of viruses and cells on the particles. The particles itself may be coated on the cell modification surface or may be utilized in suspension and immobilized on the cells by centrifugation.

In other embodiments of the invention the cell modifying surfaces are functionalized with modified, e.g. pseudotyped, viruses as vectors such as disclosed in WO2008/037458. Vectors derived from the gamma-retroviruses, for example, the murine leukemia virus (MLV), have become a standard tool for gene transfer technology and have been frequently used in clinical gene therapy trials (Ross et al., Hum. Gen Ther. 7:1781-1790, 1996). Pseudotyping of retroviral vectors, including HIV vectors or MLV vectors, refers to the incorporation of envelope proteins from heterologous viruses into the retroviral envelope membrane. Such pseudotyped retroviral vectors then exhibit a receptor phenotype similar to the virus from which the envelope protein was derived. Depending on the host range of said virus, the pseudotyped retroviral vectors will then have a broadened or a narrowed host range as compared to vector particles having the incorporated homologous retroviral envelope proteins. Useful pseudotyped vectors include MLV vectors pseudotyped with the HIV Env protein, the Ebola virus glycoprotein, or the baculovirus glycoprotein.

The measles virus (MeV), a prototype morbillivirus of the genus Paramyxoviridae, utilizes two envelope glycoproteins (the fusion protein (F) and the hemagglutinin protein (H)) to gain entry into the target cell. WO2008/037458 discloses the pseudotyping of retroviral vectors with heterologous envelope proteins derived from the Paramyxoviridae family, genus Morbillivirus. The incorporation of morbilli virus F and H proteins having truncated cytoplasmic tails into lenti viral vector particles allows an effective transduction of cells. In addition, these pseudotyped vector particles allow the targeted gene transfer into a given cell type of interest by modifying a mutated and truncated H protein with a single-chain antibody or ligand directed against a cell surface marker of the target cell, e.g. the stem cell marker CD133.

Cellular Modification

The term “modification of cells” refers to all processes which result in a morphological, functional, or molecular modification of the cells (e.g. activation, proliferation, reprogramming, dedifferentiation, differentiation or maturation). An embodiment of the invention comprises techniques like cell activation or stimulation for example by agonistic or antagonistic antibodies or cytokines or the in vitro modulation of cells like the in vitro expansion and/or genetic modification of lymphocytes. For example, T-lymphocytes can be cultured with antibodies against cell surface molecules like CD3 either bound to a macroscopic matrix like the cell modifying surfaces according to an embodiment of the invention or in soluble form in the presence of antigen presenting cells, e.g. using peripheral blood mononuclear cells (PBMC) or fractions thereof as feeder cells and polyclonal stimuli. Instead of CD3 antibodies, specific antigens can be used for the stimulation and expansion of antigen-specific T-cell. In these types of cultures viral transductions of the T cells or any other type of genetic modification as described above can also be performed as already described, to achieve cellular modifications.

The cellular modification of cells within a method in accordance with an embodiment of the invention comprises for example the use of feeder cells or modifying cells that secrete certain metabolites, growth or differentiating factors into the medium or that directly deliver signals to the cells to be modified.

Feeder cultures, which secrete growth factors, can be prepared from splenocytes, macrophages, thymocytes, or fibroblasts. E.g. mouse embryonic fibroblasts (MEFs) are often used as feeder cells in human embryonic stem cell research. Genetically modified cells, such as K562 cells, stably transfected with stimulatory molecules, e.g. MHC class I or MI-IC class II, ligands for costimulatory molecules CD2R, ICOS, Notch, CD137, CD40 or cytokines, e.g. IL-2 or IL-15 or facilitating molecules, e.g. Fc-gamma receptor (for labelling with Fc-bearing stimulatory molecules, e.g. antibodies or Fc-fusion proteins) can also be used.

Cellular modification with a method according to an embodiment of the invention may further comprise the delivery of transcription factors (TFs) into cells promoting differentiation, transdifferentiation or dedifferentiation/reprogramming of the target cells. In such an embodiment of the invention, the method comprises altering the state of a cell, for example an adult somatic cell, embryonic or adult stem cell, or a mesenchymal stem cell (MSC) by introducing one or more transcription factors or substances, which alter the expression or activity of said transcription factors, into the cells. The cells then alter the expression level of at least one polypeptide (e.g. Oct3/4 for an induced pluripotent stem cell) and/or epigenetic programming of the cell is changed.

Introducing the transcription factor into the target cells can be achieved by contacting a cell with a transcription factor, a polypeptide or fragment thereof fused to a protein transduction domain which allows entry of the protein into the cell or by any other means to transport active substances as defined above into cells and thereby altering the expression profile and/or epigenetic status, e.g. leading to reprogramming the cells. For example, Xie et al (2004, Cell: 117:663-676) disclose a method for the forced expression of a single TF to trigger a specialized B cell to transdifferentiate into a macrophage.

Cellular modification of cells during methods according to embodiments of the invention can be further achieved with a cocktail of extrinsic signaling molecules to enhance differentiation and widen the spectrum of MSC plasticity. A suitable method to deliver TFs into MSCs is disclosed by Brazilay et al (2009), Stem Cells, 27:2509-2515.

A method according to an embodiment of the invention is especially suited for the modification and expansion of T cells, either polyclonal or antigen-specific. The interaction of T-cells with a stimulatory agent like a stimulatory antibody or specific MHC/peptide complex on the surface of an antigen presenting cells (APC) can be increased by the increased gravitational force during centrifugation. For this purpose, the cultural surfaces can be coated with T cell stimulatory molecules like stimulatory antibodies against CD3, CD28 or CD137. It is advantageously to activate the T-cells to be modified with stimulatory antibodies in a soluble form or with particles coated with stimulatory antibodies during a process in accordance with an embodiment of the invention. Furthermore, T-cells can be co-cultured with APC, like T-cell depleted PBMC or artificial APC (e.g. K562 cells, transfected with Fc-gamma receptor and/or MHC molecules and/or costimulatary molecules, like CD137 ligand, or CD28 ligands), in various ratios (e.g.: 10:1 to 1:1000 T cells/APC).

Instead of stimulatory antibodies, T-cells can be co-cultured with specific antigens, e.g. defined an peptides, purified defined proteins or protein mixtures or lysates of defined pathogens. This type of culture could be useful for activation or expansion of antigen-specific T-cells. Furthermore, any kind of T cell stimulatory agent can be used within a method according to an embodiment of the invention, e.g. PMA, ionomycin, superantigens like SEB, lectins, like ConA or PHA.

A method according to an embodiment of the invention allows the regulation of the interaction of T-cells with stimulating substances or cells via the centrifitgation time and/or rotational speed. The interaction between the cells to be modified, the cultural surfaces and the substances or cells (like APC) applied to the centrifugation Chamber can repeated as required to restimulate the cells or initiate their expansion. Furthermore, fresh media, cytokines other substances relevant for the cell modification/culture can be added in an automated fashion, without the necessity to interrupt the interaction between cells and coated surface or APC.

The above mentioned substances, ligands, factors, agents, particles or cells may be applied, coated or adhered to the cultural surfaces or introduced into the centrifugation chamber with the culturing liquids.

Cellular Layers

A layered cell composition according to an embodiment of the invention comprises at least two layers of cells with the same or different cell type or phenotype. Preferably, the layered cell composition comprises 2 to 10, especially 2 to 5 layers of cells with different cell type or phenotype. Each of these layers may comprise one or more (like 10 to 50) layers of the same cell type. Layered compositions of embodiments of the invention may consist of complex cellular tissue, like stem cells on top of feeder cells, skin tissue or organs and may comprise same or different types of cells for example stem cells, fibroblasts, keratinocytes, melanocytes, epithelial cells, endothelial cells, antigen-presenting cells (B cells, dendritic cells, macrophages).

In such an embodiment of the invention, for example cells of a first type are cultured on the cell modifying surface of the centrifugation chamber. On this first layer, cells of a second type are placed or immobilized by the centrifugal forces, which furthermore enhances the contact and interaction between the cells of the first and second type. Further layers or cell types can be placed on the existing cell layers resulting in a multilayer cell structure. In addition, matrices can be used for culturing the cells in three-dimensional structures. Such matrices are for example three-dimensional lattices e.g. proteoglycans, collagen or artificial matrices useful for culturing cells in three dimensions.

With methods and devices in accordance with embodiments of the invention, it is possible to generate layered cell composition resembling human skin. Such layered cell compositions may be used, for example, as artificial skin.

Devices According to Embodiments of the Invention

Figure 1:
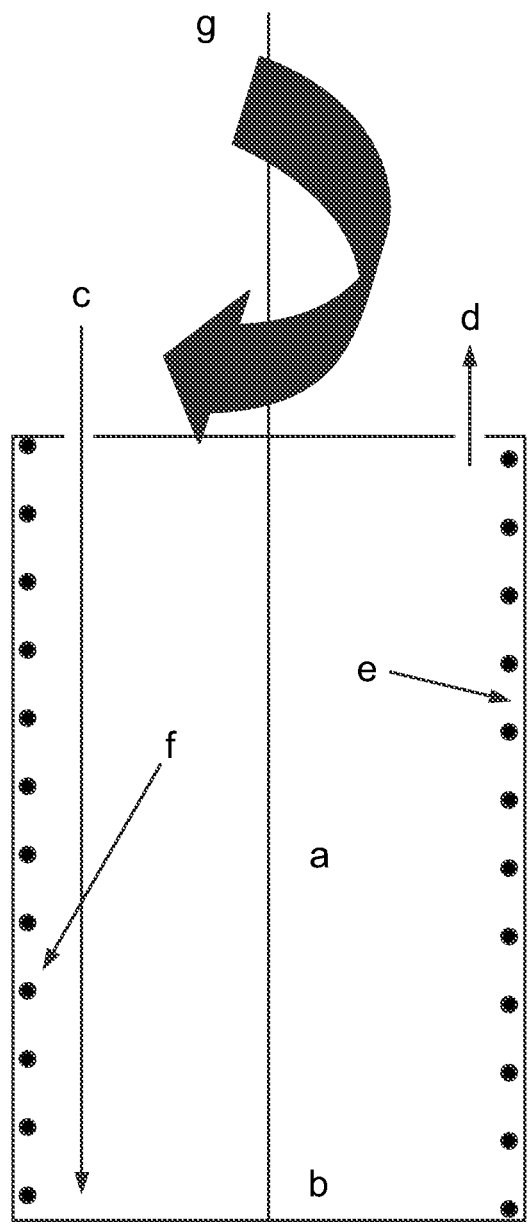
FIG. 1 is a schematic view of a cell modification device used in embodiments of the invention.

A schematic view of a cell modification device according to an embodiment of the invention is shown in FIG. 1 with centrifugation chamber (a), rotational axis (g) and culturing surfaces (e). The culturing surfaces can be positioned parallel to the rotational axis (g), i.e. the normal vector of the culturing surfaces shares an angle of 90° with the rotational axis (g). By rotation of the chamber by axis (g), cells (f) are immobilized at the culturing surfaces (e) and can be supplied with cell culturing medium via at least one inlet/outlet port, like the shown inlet (c) and outlet port (d).

Devices according to one or more embodiments of the invention may be equipped with one port which is used for both the introduction and removal of cells, media or gases into or out of the chamber. In another variant, at least two ports, for example one inlet and one outlet port for liquids and one or more ports for gas exchange are used. The ports are preferably integrated into the rotational axis of the centrifugation chamber and may in the case of one inlet and one outlet port be attached from the same or from different sides of the centrifugation chamber.

Figure 2:
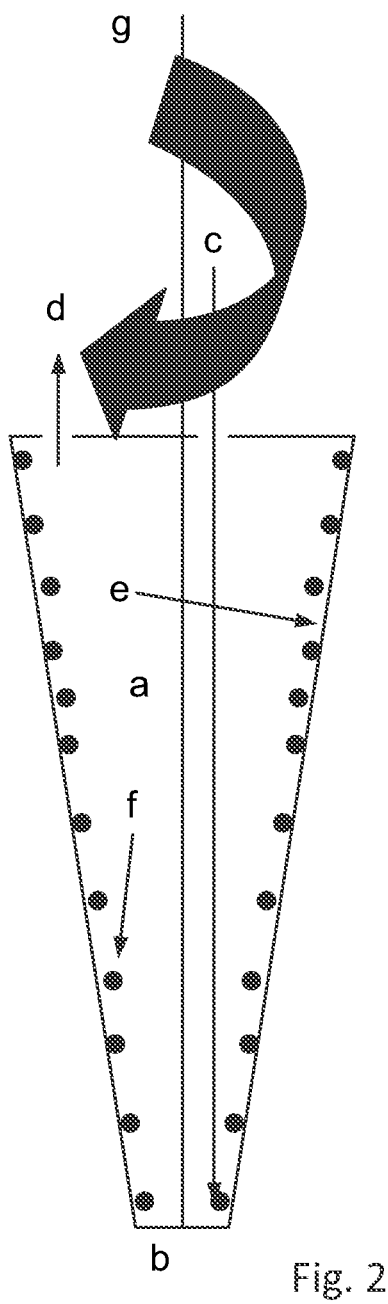
FIG. 2 shows an embodiment of the invention with a conical shaped chamber having culturing surfaces with a normal vector sharing an angle different than 90° (for example 105°) with the rotational axis (g).

A conical shaped chamber having culturing surfaces with a normal vector sharing an angle different than 90° (for example 105°) with the rotational axis (g) is shown in FIG. 2. In this embodiment, the cells and the media can move over the cell modifying surface depending on the rotational speed towards the side of the chamber having the wider diameter (in FIG. 2: upward). This can be advantageously used for genetic modification of the cells, for example with a cell modifying surface coated with virus particles for retroviral transduction. By movement of the cells over the surface, the contact area of the cells to the surface is enhanced, thereby enhancing the chance for cell modification like retroviral transduction. Furthermore, the cells are supplied by the movement of media over the cells in form of a thin film.

If a method according to an embodiment of the invention comprises a processing step wherein the cells are moving (or forced) over the cell modifying surface during rotation of the chamber, it is preferable to employ at least two different rotational speeds of the centrifugation chamber. For example in a first processing step, a higher rotational speed resulting in centrifugal forces of 100 g to 1000 g moves the cells towards the side of the chamber having the wider diameter and in a second processing step at lower rotational speed or even stopped chamber the cells slide down the cell modifying surfaces towards the base plate b). The processing steps of at least two different rotational speeds may be repeated as often as needed to achieve the desired level of cell modification.

Figure 3:
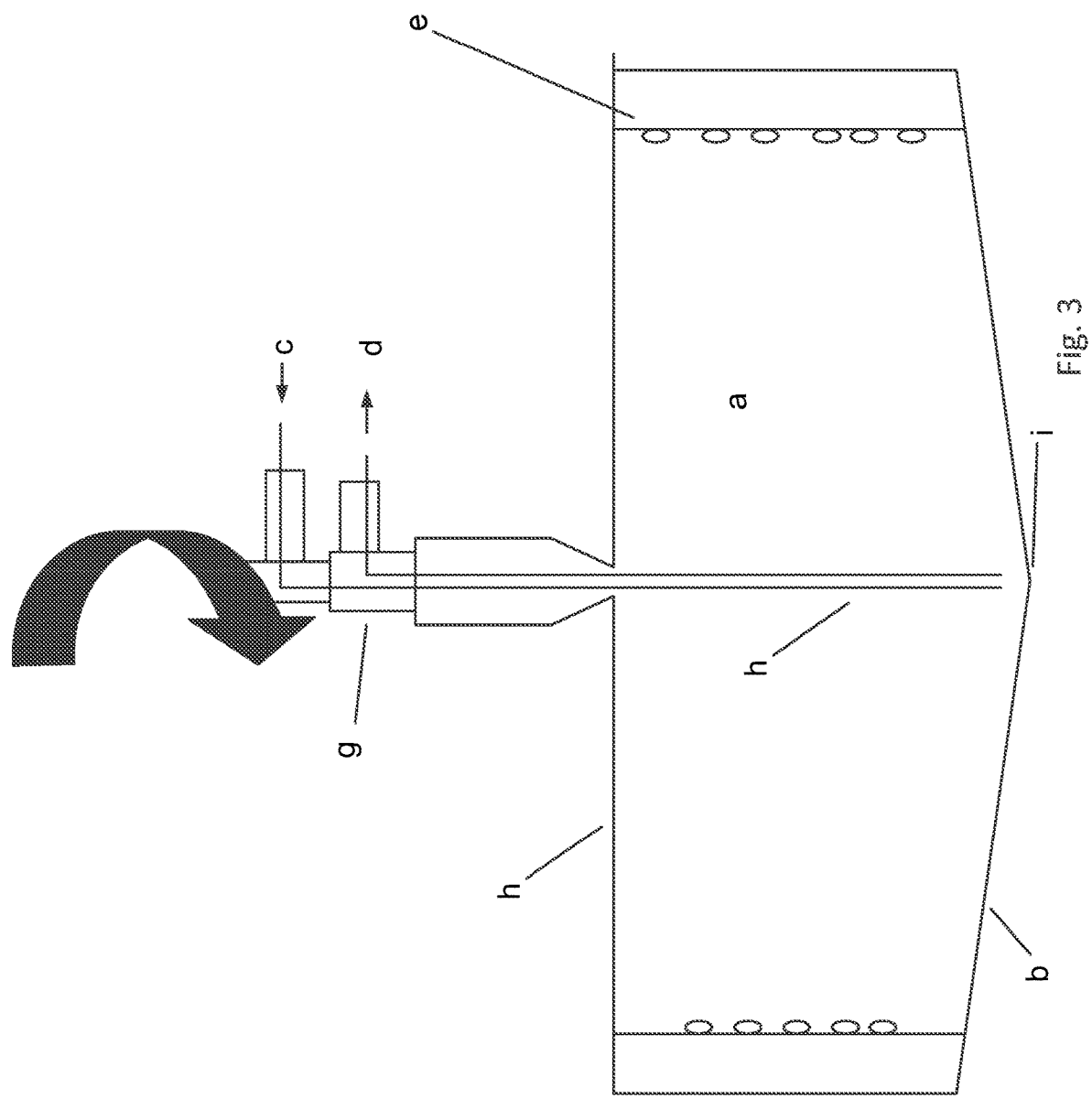
FIG. 3 shows another embodiment of the device of the invention, wherein the chamber and/or the element have a conical bottom or base plate (b) and at least one aperture or tube (h) reaching to the bottom of the chamber and/or the element.

FIG. 3 shows another embodiment of a device according to an embodiment of the invention, wherein the chamber and/or the element have a conical bottom or base plate (b) and at least one aperture or tube (h) reaching to the bottom of the chamber and/or the element. During rotation, the cells (f) are immobilized at the cultural surfaces (e). If the rotation of the chamber is too slow or even stopped, the cells will accumulate at the lowest point (i) of the conical bottom or base plate (b) and can be removed by the internal tube (h) and outlet port (d).

The centrifugation chamber comprises at least one cell modifying surface at which the cells are immobilized by the rotation of the centrifugation chamber. The cell modifying surface is located in the centrifugation chamber or on the inner surface of the centrifugation chamber and may have any three dimensional shape like a wall or barrier as thin as mechanically possible with a height according to the sample size or the cell population to be modified.

The cell modifying surface may be located on the inner surface of the centrifugation chamber, a spiral-shaped element or on at least one cylindrical element. In an embodiment, the centrifugation chamber may have a base and cylindrical walls rotating about a rotational axis, with at least one cell modifying surface with a cell modifying substance disposed on the cylindrical walls, the cylindrical walls having a normal vector having an angle of 135–45° to the rotational axis. The centrifugation chamber may include at least one input/output port and the cells to be modified are immobilized at the cell modifying surfaces by the rotation of the centrifugation chamber at 2 to 2000 g. The input/output port may be integrated into the rotational axis of the centrifugation chamber. The cell modifying substance may be selected from the group of substances that enhance proliferation of cells, that induce genetic modification and that induce cellular modification of cells. The cell modifying substance may modify the behaviour, structure or function of cells.

The cell modifying surface may be located on at least one cylindrical element or structure like a wall or a layer. The number of cylindrical elements depends on the volume of the centrifugation chamber and/or the number of cells to be modified/cultured. In an alternative, the cell modifying surface may be in the shape of a spiral with or without an opening to the outside of the spiral to avoid the loss of medium due to centrifugal forces.

In another embodiment of the invention, the cell modifying surfaces are located on or are a part of an element insertable into the centrifugation chamber. Preferably, the cell modifying surfaces and/or the cylindrical element and the structures therein may comprise apertures or segments to facilitate the flow of medium to any part of the cell modifying surfaces in order to supply all cells immobilized on the cell modifying surface in sufficient manner. The cell modifying surfaces, the cylindrical element or the internal structures may furthermore comprise an appropriate number of spacer elements to ensure the mechanical stability of the cell modifying surfaces during centrifugation and to ensure the free flowing of cell culture liquid and gases through the chamber.

Cell modifying surfaces in the form of a spiral can be obtained by winding up a film or foil to form a coil. Cell modifying surfaces located on a coiled film can be used without apertures or segments, since the liquid is forced through the chamber by the centrifugal forces. In another variant, the film comprises spacer elements to ease the flow of liquids between the film layers. The coil of film can be inserted in the chamber or into an appropriate concentric element to form a spiral. By using a film as substrate for the cell modifying surfaces, high surface areas for high cell densities or cell numbers can be provided.

Figure 4:
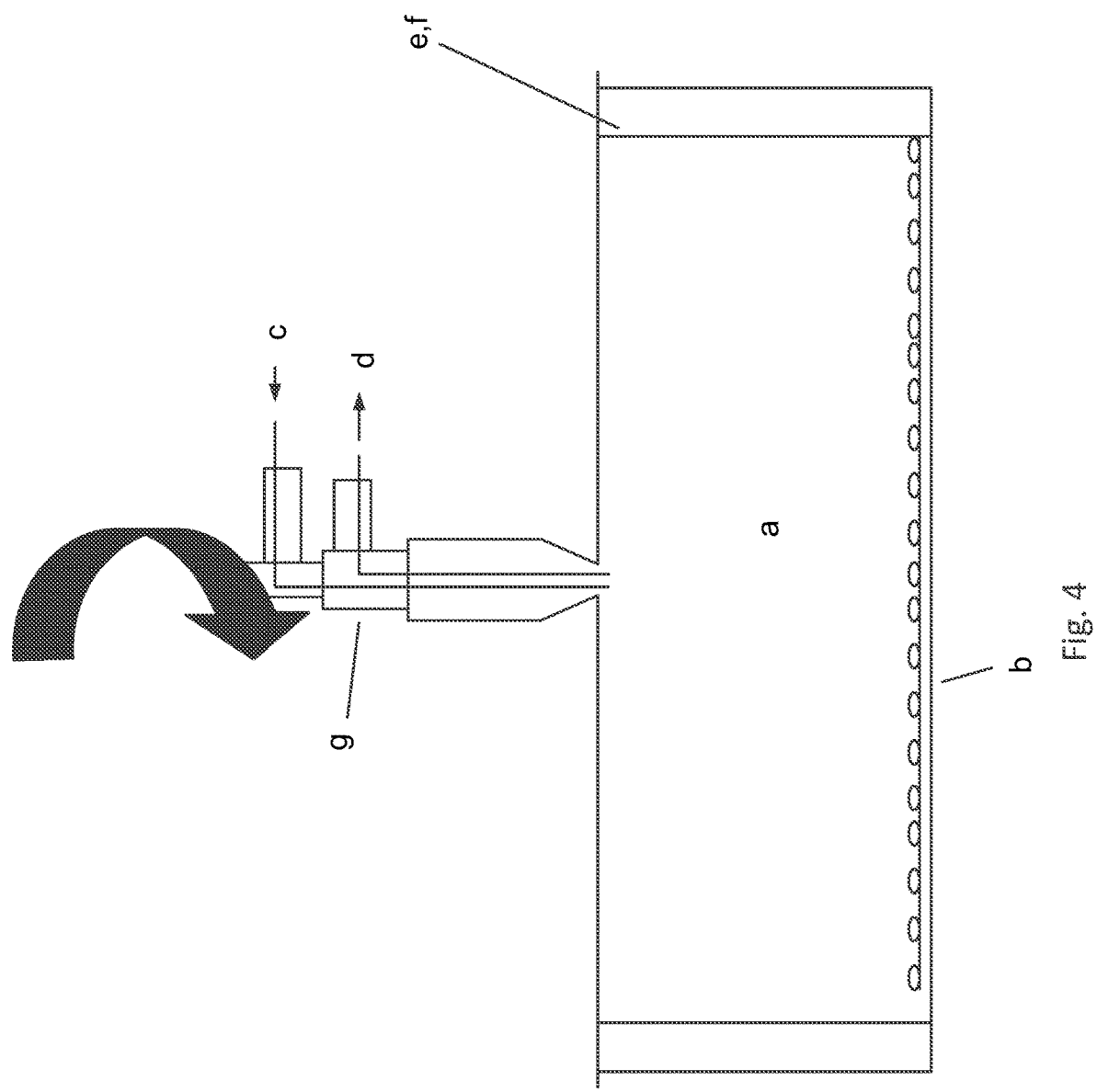
FIG. 4 shows several embodiments of centrifugation chambers with a plurality of internal structures or concentric elements in top view.

FIG. 4 shows several embodiments of centrifugation Chambers with a plurality of internal structures or concentric elements in top view, Label (193) denominates the rotational axis and (194) the outer wall of the chamber. The cell modifying surfaces are labelled with (191) and (192) and may be concentric or spiral-shaped elements. The cell modifying surfaces can comprise spacer elements (195) generating sufficient space between the cell modifying surfaces for free flowing of cell culture liquid and gases.

It is furthermore possible that the centrifugation chamber comprises at least two cell modifying surfaces which are functionalized with the same or different at least one substance enhancing proliferation of cells, and/or inducing genetic modification and/or inducing cellular modification of cells. The cell modifying surfaces may have different functionality or different coated surfaces. In this embodiment, the device may comprise at least a first cell modifying surface with a normal vector having an angle of 135–45° to the rotational axis of the centrifugation Chamber and at least a second cell modifying surface with a normal vector having an angle of (–45)–45° to the rotational axis of the centrifugation chamber.

Figure 5:
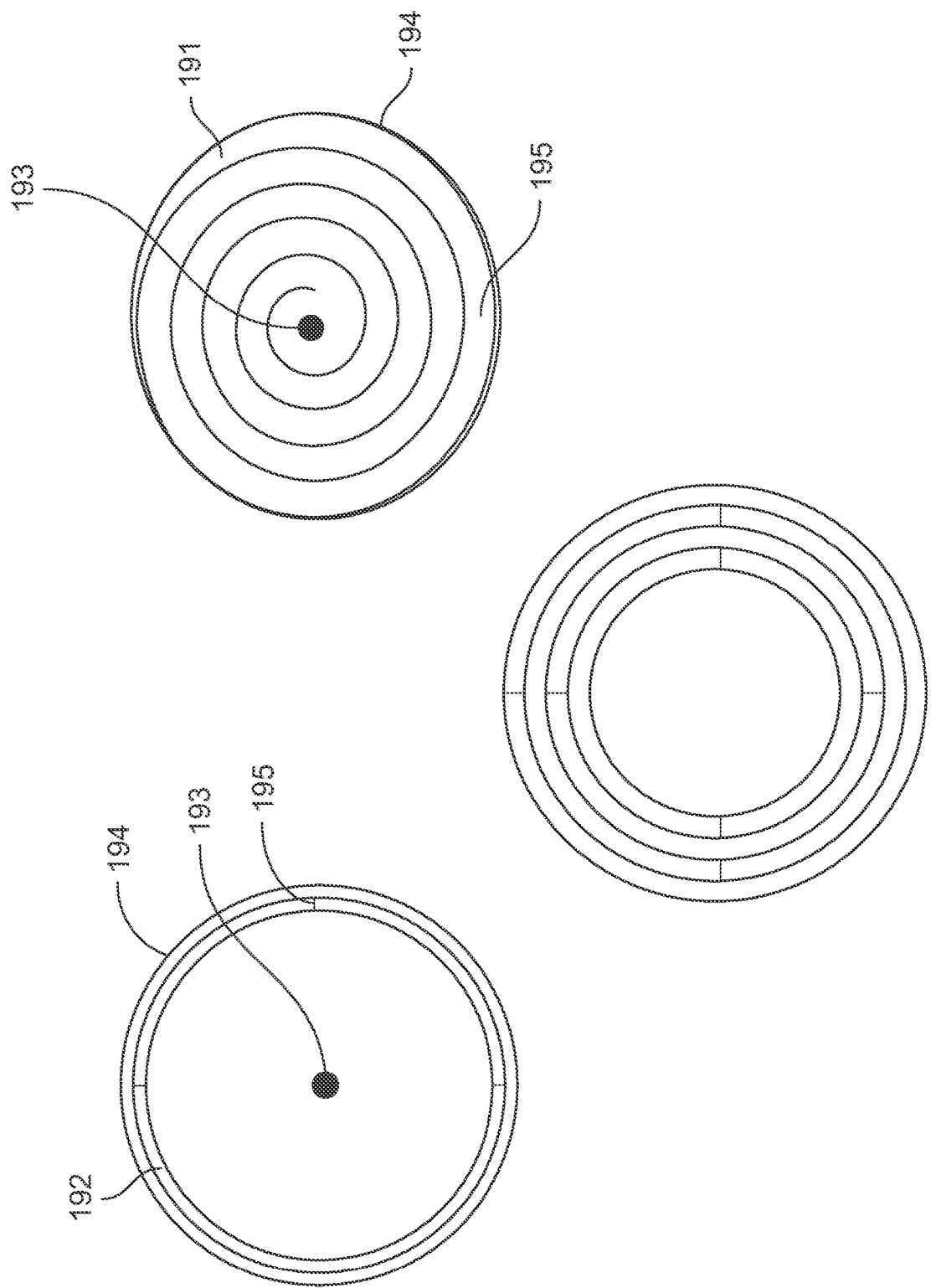
FIG. 5 shows an embodiment with two cell modifying surfaces; the first cell modifying surface (b) having a normal vector of about 90° to the rotational axis of the centrifugation chamber and the second cell modifying surface (e) having a normal vector of about 0° to the rotational axis of the centrifugation chamber.

For example, the cell modifying surfaces with a normal vector having an angle of 135–45° to the rotational axis of the centrifugation chamber can be functionalized for genetic modification of the cells, whereas the cell modifying surfaces with a normal vector having an angle of (–45)–45° to the rotational axis of the centrifugation chamber can be functionalized for proliferation of the cells. FIG. 5 shows this embodiment, with the first cell modifying surface (b) having a normal vector of about 90° to the rotational axis of the centrifugation chamber and the second cell modifying surface (e) having a normal vector of about 0° to the rotational axis of the centrifugation chamber. This embodiment of the invention allows at least two different modification steps at two different cell modifying surfaces in one chamber without the need to change the cell modifying surfaces during the process.

Figure 6:
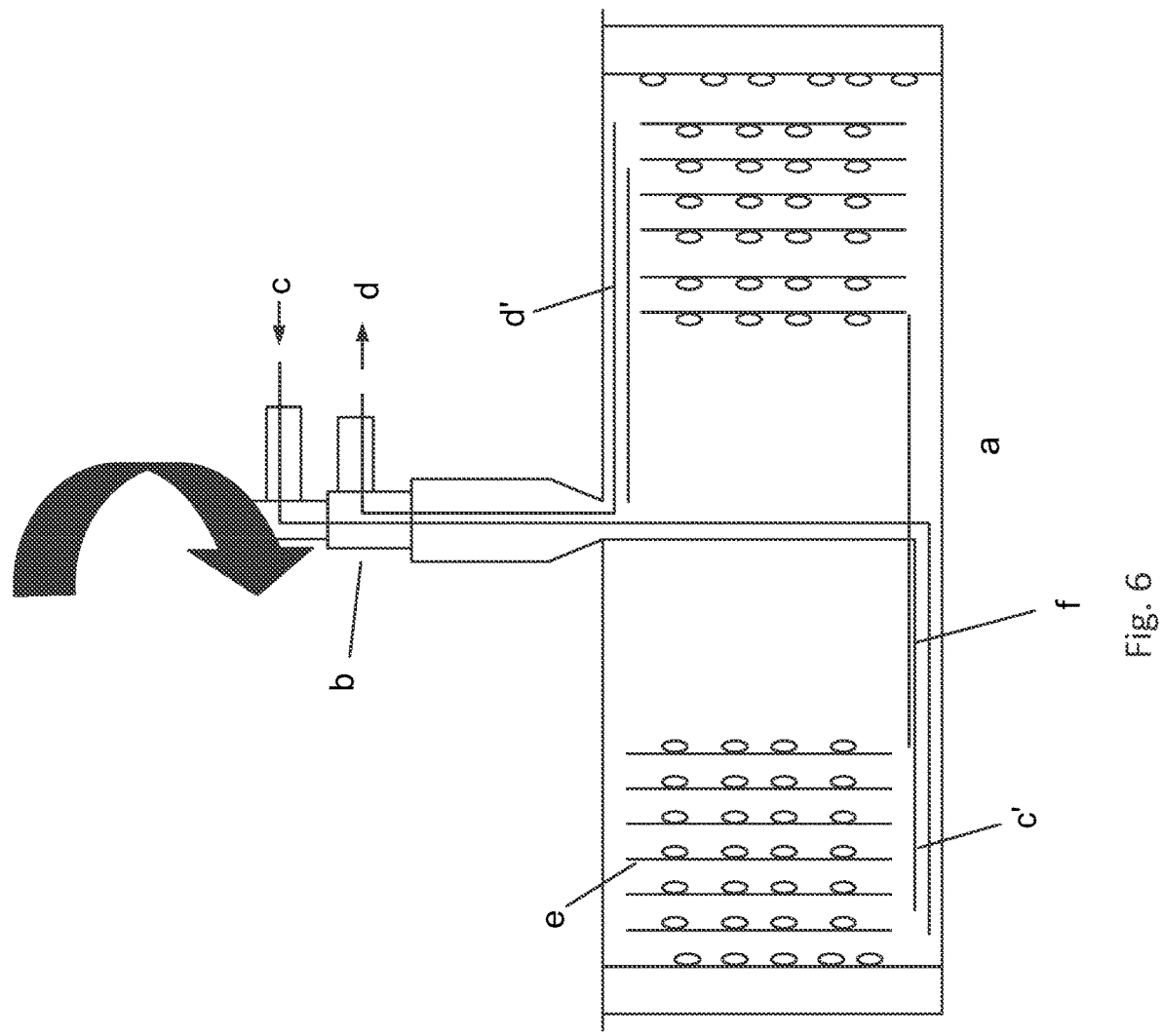
FIGS. 6 and 7 show a variant with concentric or spiral-shaped cell modifying surfaces (e) with a normal vector having an angle of 135–45° (shown 90°) to the rotational axis of the centrifugation chamber and a second cell modifying surface (f) with a normal vector having an angle of (−45)–45° (shown with an angle of 0°) to the rotational axis of the centrifugation chamber.
Figure 7:
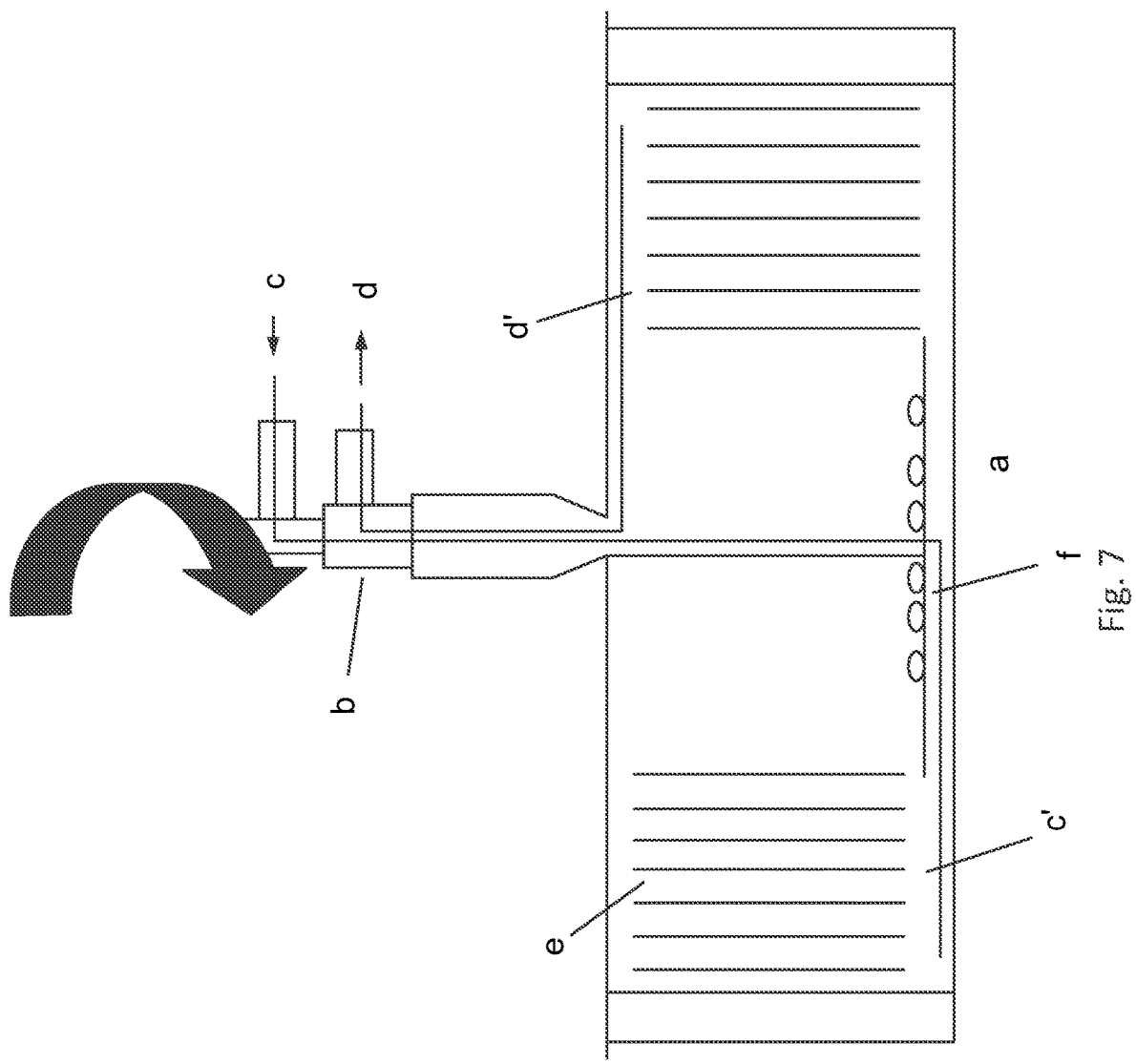

FIGS. 6 and 7 show another variant of this embodiment by way of example with concentric or spiral-shaped cell modifying surfaces (e) with a normal vector having an angle of 135–45° (shown 90°) to the rotational axis of the centrifugation chamber and a second cell modifying surface (f) with a normal vector having an angle of (–45)–45° (shown with an angle of 0°) to the rotational axis of the centrifugation chamber. The centrifugation chamber shown in FIG. 6 is in a centrifugation state, where all cells are immobilized at the cell modifying surfaces (e) by the centrifugal forces, FIG. 7 shows the device after stopping the rotation of the chamber around axis b, the cells are rinsed from the cell modifying surfaces (e) and can be further cultured on the cell modifying surface (f) as shown in FIG. 7.

The cell culturing liquid may be supplied in a constant flow or is moved by variations of the speed of rotation over the cells. For example, in FIG. 8, the cell modifying surfaces (e) are not or not throughout connected to the second cell modifying surface (f) and the top cover of the chamber, thereby allowing a flow of cell culturing liquid and gases via tubing or channels c' and d'. Optionally tubing or channel d' comprises apertures for distribution of the cell culturing liquid and gases over the cell modifying surfaces (e).

The chamber may comprise at least one aperture allowing a flow of cell culturing liquid and/or gases into and out of the chamber. The aperture is preferable located in the axis (g) of the centrifugal chamber or concentric element as shown in FIG. 8. The cell culturing liquid and/or gases are supplied via inlet and outlet port c/d located in the rotational axis (g) and are then forced by the centrifugal movement over the cultural surfaces. The cell culturing liquids can be either withdrawn from the system via tubing or channel d' or directed back into the moulded element or the centrifugal chamber via bypass (c').

FIG. 9 shows another embodiment of the invention, in which concentric or spiral-shaped cell modifying surfaces (f) with a normal vector having an angle of 135–45° (shown 90°) to the rotational axis of the centrifugation chamber and second cell modifying surface (h) with a normal vector having an angle of (–45)–45° (shown 0°) to the rotational axis of the centrifugation chamber are combined. In this embodiment, the second cell modifying surfaces are attached to the first cultural surface (f) in a way that cells may be easily be transferred from the first to the second cultural surface and vice versa by change of rotational speed of the chamber. In this embodiment, the first and second cultural surfaces have a different functionalized coating thereby providing different modification to the cells.

The concentric elements as supporting structures for the cultural surfaces, the cultural surfaces itself and/or the centrifugation chamber may be made of various materials, preferably from plastics like, for example, polystyrene (PS), polyvinylchloride (PVC), polycarbonate, glass, poly acrylate, poly acrylamide, polymethylmethacrylate (PMMA), polyethylene terephthalate (PET), poly tetrafluorethylene (PTFE), thermoplastic polyurethane (TPU), silicone, poly ethylene (PE) poly propylene (PP), polyvinyl alcohol (PVA) or compositions comprising one or more of the above mentioned materials. In a preferred embodiment, the cell modifying surfaces may be coated with a biodegradable material, for example, collagen, chitin, alginate, and/or hyaluronic acid derivatives, poly lactic acid (PLA) polyglycolic acid (PGA) and their copolymers.

The size of the centrifugation chamber depends on the number of cells to be modified and may have the size of 2 cm to 50 cm in diameter and a height of 5 mm to 50 cm.

A centrifugation chamber of a device according to an embodiment of the invention may be a single component with the cultural surfaces and/or supporting structures like concentric elements for the cultural surfaces. In another embodiment of the invention, the centrifugation chamber consists of an outer chamber (for example made from stainless steel) in which one or more concentric elements made from the above mentioned materials can be inserted. The cell modifying surfaces are then located on or are a part of the concentric elements.

The concentric elements may be disposable (i.e. single use) or may be designed and manufactured for re-use after washing and sterilization.

Furthermore, the cell modifying surfaces can be rough-textured, grooved and/or may comprise pockets or recesses to enhance the adherence of the cells to be cultured.

A process according to an embodiment of the invention can be automated for example in a sample processing system as known from EP 0869838131 and WO 2009/072003. The methods described here allow for automation in a closed cell modification device eliminating the risk of contamination of the cell culture compared to a standard non-closed transduction process, especially when the transduction process is repeated several-fold. In addition, safety of the operator is increased due to reduction of direct contact with biological hazardous material like retroviruses.

Systems According to Embodiments of the Invention

Yet another object of one or more embodiments of the invention relates to systems for cell modification. One of skill in the art will recognize that such a system may comprise a standalone device, or a plurality of devices configured to operate in conjunction with each other in an embodiment, such a cell modification system comprises:
a) a centrifugation chamber with at least one cell modifying surface with a normal vector having an angle of 135–45° to the rotational axis of the centrifugation chamber and at least one input/output port
b) a device to rotate the centrifugation chamber so as to apply a centrifugal force to cells.

The systems may furthermore comprise:
c) at least one container containing the cells to be modified
d) at least one container for the cells to be modified
e) at least one container containing cell media
f) a tubing set connecting centrifugation chamber and container
g) at least one pump and
h) a plurality of valves.

In one or more embodiments, the systems for cell modification can be operated by controlling the device to rotate the centrifugation chamber, the pump and the valves to introduce the cells to be modified and cell media into the centrifugation chamber, rotate the centrifugation chamber and remove modified cells from the centrifugation chamber.

The system of the present invention can include various mechanical, electromechanical, and magnetic components. A system according to an embodiment of the invention is shown in FIG. 10, wherein the centrifugation chamber 128 having input/output port 130 can be connected to pump 108 and a plurality of valves 110. Container for the cells to be modified, the modified target cells and cell media are not shown but can be placed on hooks 114.

As shown in FIG. 10, the system has a portable size that can be placed at a point/center-of-care for on-site cell modification.

The system can optionally include a magnetic separation unit 106 with housing for positioning a separation column like a magnetic separation column.

The system 100 further includes a pump 108 and a plurality of fluid flow control means or valves, as illustrated by one or more valves 110. The components of the system 100 (e.g., centrifugation chamber, valves, pump, separation unit, etc.) can be coupled or connected by one or more flow paths so as to form a series of fluid pathways or fluid circuits. The system further includes a computer control system or unit 112 providing monitoring and/or control of one or more aspects of the system 100. The computer system 112, as described above, can include one or more input and/or output devices, graphical displays, user interfaces and may allow for manual and/or automated control of system 100 operation and functions. The computer control system 112 can include a module or system to process information (e.g., flow information, etc.) within the system 100 and can include a wide variety of proprietary and/or commercially available computers, components or electronics having one or more processing structures and the like, with such systems often comprising data processing hardware and/or software configured to implement any one or a combination of method steps as described herein. Software will typically comprise machine readable code of programming instructions embodied in a tangible media such as a memory, digital or optical recording media, optical, electrical, or wireless telemetry signals, or the like, and one or more of these structures may also be used to output or transmit data, signals, or information between components of the system in any of a wide variety of signal processing architectures.

The system can further include various supports, sensors, housings, etc. for various components that can be coupled with the present system to perform methods as described herein.

The system 100 further includes one or more support structures 114 configured to hold and/or support various fluids, reagents, samples fluid reservoirs, filters, and the like that can be utilized with the system 100 according to the present invention. Support structures can include various hook or hanger, or holder (e.g., filter holder or housing) configurations and are not limited to any particular design. Fluids, buffers, reagents, etc. positioned on a support 114 can be coupled to a fluid path or tubing, that can in turn be connected to more or more components of the system 100. The system 100 can include sensors for monitoring and/or further controlling fluid flow through the system. Sensors can include, for example, liquid sensors, which can include bubble detectors (ultrasonic detector), pressure sensors, and the like. Bubble detector 116 and pressure sensors 118 are shown. A support 120 is shown, which can be configured to hold a filter or volume reduction unit. Collection area 122 can support collection containers, reagents, etc.

Processing unit 104 can include a housing or cover 124, that can be movable (e.g., removable) about one or more hinge. The cover 124 at least partially defines a processing area 126 that can be temperature controlled and coupled to temperature monitoring and control components that may be housed within the housing 105 of the system 100. The processing unit 104 includes a centrifugation chamber 128 configured for holding and processing (e.g., centrifugation, culturing, sample component separation, etc.) of a sample. The centrifugation chamber 128 shown is a rotating chamber held in position about an axis that can include an anti-rotation lock 130. The processing unit 104 can include one or more detection systems, such as an optical detector 132 positioned within the cover 124 and configured to detect or monitor processing of a sample in the chamber 128. One or more fluid input/output lines can be coupled to the chamber 128 and may be held in position by a holder 134.

Point/Center-of-care and/or Portable Device

Each manipulation or addition of reagents to the cell preparation described herein (e.g., washes, stimulation, transduction, feeding, sampling) creates a risk for error and for contamination that can lead to a failed production run. A reliable solution includes implementing closed culture systems, where the cell manufacturing takes place in bags with closed tubing pathways and connections, maintaining a sterile environment. Such a method is described by Tumaini B, Lee D W, Lin T, Cashello L, Stroncek D F, Mackall C et al., "Simplified process for the production of anti-CD19-CAR-engineered T cells," *Cytotherapy* 2013, who implemented a simplified, semi-closed system for the cGMP preparation of anti-CD19 CAR-modified T cells. Several distributors of GMP quality culture bags, tubing accessories and connectors, as well as sterile tubing welders (e.g., Terumo tubing welder, Terumo BCT, Lakewood, Colo., USA) make it simpler to convert research protocols to functionally closed manufacturing processes where 'open' process steps are reduced and therefore risks for cross contamination are minimized.

As described herein, patient-derived cells that are used for generation of gene-modified T cells can be highly variable as source material. Bellone G, Turietti A, Artusio E, Mareschi K, Carbone A, Tibaudi D et al. "Tumor-associated transforming growth factor-beta and interleukin-10 contribute to a systemic Th2 immune phenotype in pancreatic carcinoma patients," *Am J Pathol* 1999; 155: 537-547; 11. Decker T, Fischer G, Bucke \V, Bucke P, Stotz Gruneberger A et al. "Increased number of regulatory T cells (T-reps) in the peripheral blood of patients with Her-2/neu-positive early breast cancer," *J Cancer Res Clin Oncol* 2012; 138: 1945-1950; Karp J E, Ricklis R M, Balakrishnan K, Briel J, Greer J, Gore S D et al. "A phase 1 clinical-laboratory study of clofarabine followed by cyclophosphamide for adults with refractory acute leukemias," *Blood* 2007; 110: 1762-1769. T cells destined to be genetically modified often originate from heavily drug pre-treated patients whose PBMCs may contain abnormal levels of inhibitory factors, inhibitory cells or populations of T cells that poorly respond to stimulation. This clearly challenges the ability to define the reproducibility of the manufacturing process. Separating T cells from these inhibitory elements can greatly improve the outcome of the T-cell culture. Goldstein M J, Kohrt H E, Houot R, Varghese B, Lin J T, Swanson E et al. "Adoptive cell therapy for lymphoma with CD4 T cells depleted of CD137-expressing regulatory T cells," *Cancer Res* 2012; 72: 1239-1247; Gomez-Eerland R, Nuijen B, Heemskerk B, van Rooij N, van den Berg J H, Beijnen J H et al. "Manufacture of Gene-Modified Human T Cells with a Memory Stem/Central Memory Phenotype," *Human Gene Ther Methods* 2014; 25: 277-287. The use of large magnetic beads coated with anti-CD3 and anti-CD28 (i.e., the CTS Dynabeads CD3/CD28) in combination with a large magnet adapted for bags is an elegant approach as they allow for simultaneous isolation and stimulation of T cells from the PBMC product which enables a more robust process.

Instead of using the entire T-cell population, in an embodiment, specific subsets of T cells are used for gene modification. For example, in such embodiments, antigen-specific T cells already present in memory populations in the patient are optimally primed against viral pathogens. Endogenous antigen-reactive memory T cells against Cytomegalovirus or Epstein-Barr virus have thus been used as a source of T cells for gene-engineering. van Loenen M M, de Boer R, van Liempt E, P, Jedema I, Falkenburg J H et al. "A good manufacturing practice procedure to engineer donor virus-specific T cells into potent anti-leukemic effector cells," *Haematologica* 2014; 99: 759-768, Such double-specific T cells present several advantages including the maintenance of CAR specificity on long-lived memory I cells and anti-viral effector activity that prevents viral reactivation following lymphodepletion and ACT. Louis C U, Savoldo B, Dotti. G, Pule M, Yvon E, Myers G D et al. "Antitumor activity and long-term fate of chimeric antigen receptor-positive T cells in patients with neuroblastoma," *Blood* 2011; 118: 6050-6056; Pule M A, Savoldo B, Myers G D, Rossig C, Russell H V, Dotti G et al. "Virus-specific T cells engineered to coexpress tumor-specific receptors: persistence and antitumor activity in individuals with neuroblastoma," *Nat Med* 2008; 14: 1264-1270. Engagement of their native receptor in vivo by cells infected with these persistent viruses in the host could support T-cell expansion, maintenance and effector function. Initially Epstein-Barr virus-specific T cells generated by conventional in vitro stimulation and expansion protocols have been used. However, these procedures are time-consuming and require extended culture of cells in vitro, which might affect their functionality.

In an additional embodiment, defined T-cell subsets (i.e., naive, central memory or memory stem cells) have important functional advantages and are considered a better source of starting material. Berger C, Jensen M C, Lansdorp P M, Gough M, Elliott C, Riddell S R, "Adoptive transfer of effector CD8+ T cells derived from central memory cells establishes persistent T cell memory in primates," *J Clin. Investig* 2008; 118: 294-305; Gattinoni L, Lugli E, Ji Y, Pos Z, Paulos C M, Quigley M F et al., "A human memory T cell subset with stem cell-like properties," *Nat Med* 2011; 17: 1290-1297; Hinrichs C S, Borman Z A, Gattinoni L, Yu Z, Burns W R, Huang J et al., "Human effector CD8+ T cells derived from naive rather than memory subsets possess superior traits for adoptive immunotherapy," *Blood* 2011; 117: 808-814; Klebanoff C A, Gattinoni L, Restitb N P, "Sorting through subsets: which T-cell populations mediate highly effective adoptive immunotherapy?" *Immunother* 2012; 35: 651-660; Xu. Y, Zhang M, Ramos C A, Durett A, Liu E. Dakhova O et al., "Closely related T-memory stem cells correlate with in vivo expansion of CAR.CD19-T cells and are preserved by IL-7 and IL-15," *Blood* 2014; 123: 3750-3759. Large-scale clinical magnetic enrichment of T cells, as well as naive and central memory subsets can be performed in a closed and sterile system using the methods, devices, and systems described herein. The enriched T cells can then be activated by an alternative clinical reagent that is a biodegradable polymeric nanomatrix agonist for CD3 and CD28. Casati A, Varghaei-Nahvi A, Feldman S A, Assenmacher M, Rosenberg S A, Dudley M E et al., "Clinical-scale selection and viral transduction of human naive and central memory CD8+ T cells for adoptive cell therapy of cancer patients," *Cancer Immunol Immunother* 2013; 62: 1563-1573; Terakura S, Yamamoto T N, Gardner R A, Turtle C J, Jensen M C, Riddell S R., "Generation of CD19-chimeric antigen receptor modified CD8+ T cells derived from virus-specific central memory T cells," *Blood* 2012; 119: 72-82. This reagent is compatible with efficient T-cell transduction and is highly suitable for use in aseptic cell manufacturing as it can be sterile filtered.

As described above, the complex processes described herein involve many different reagents, for example, separation reagents, activation reagents, viral vectors, media, cytokines, different buffers and so on. These reagents need to efficiently and stably work together as an integrated reagent system. All raw materials in such an integrated system have to meet the requirements according to the recommendations of USP <1043> on ancillary materials. Notably, the cell culture media that will be used for commercial scale must be serum free to reduce the risk of contamination with TSE/BSE or viruses. Whenever possible, reagents should be chemically defined. Substances from natural sources, for example, especially serum should be excluded owing to their high variability, limited availability and critical risk profiles. Brindley D A, Davie N L, Culme-Seymour R I, Mason C, Smith D W, Rowley J A., "Peak serum: implications of serum supply for cell therapy manufacturing," *Regen Med* 2012; 7: 7-13.

The system may generate a standard operating protocol, which verifies and validates the entire process. Such a process should be straightforward to implement, optimize for efficiency and eliminate all unnecessary or redundant steps. For example, lentiviral vectors may be preferred over gamma retroviral vectors and non-viral methods as they can be simply and directly added to the cell culture vessel (in closed systems) and demonstrate very high transduction efficiency. Dropulic B. Lentiviral, "vectors: their molecular design, safety, and use in laboratory and preclinical research," *Human Gene Ther* 2011; 22: 649-657. Lentiviral vectors have the added advantage that they efficiently transduce non-dividing, as well as dividing cells, and they have low genotoxic potential, in contrast to gamma. retroviral vectors. Biffi A, Bartolomae C C, Cesana D, Cartier N, Aubourg P, Ranzani M et al., "Lentiviral vector common integration sites in preclinical models and a clinical trial reflect a benign integration bias and not oncogenic selection," *Blood* 2011; 117: 5332-5339; Wang G P, Levine B L, Binder G K, Berry C C, Malani. N, McGarrity G et al., "Analysis of lentiviral vector integration in HIV+ study subjects receiving autologous infusions of gene modified CD4+ T cells," *Mol Ther* 2009; 17: 844-850.

Ideally, the process should become sufficiently robust to yield equivalent product quality independently of the patient-derived cell source material and possibly the I-cell receptor or CAR used to modify the cells, assuming the transgene does not drastically impact the physiology of the expanding T-cell population.

There are currently on the market a large number of devices that can be used to perform parts of the process. For example, the COBE cell processor (Terumo BCT) can be used for cell processing and washing while maintaining the cells in a closed system. A number of devices have been designed to simplify and even automate the expansion of the stimulated and gene-modified T cells. For example, GE Healthcare (Pittsburgh, Pa., USA) has successfully developed their Xuri cell expansion system which allows the expansion of T cells to large numbers (up to 1011 depending on the model) using bags lying on a rocking platform capable of maintaining the desired temperature. Somerville R P, Devillier L, Parkhurst M R, Rosenberg S A, Dudley M E, "Clinical scale rapid expansion of lymphocytes for adoptive cell transfer therapy in the WAVE® bioreactor," *J. Transl. Med.* 2012; 10: 69. The bag is connected to a gas control unit capable of running in continuous cultivation mode with cell retention by a filtration device. The system behaves as an independent expansion unit. Another tool that simplifies T-cell expansion is the G-Rex Technology (Wilson Wolf, New Brighton, Minn., USA). The G-Rex device takes advantage of the properties of gas-permeable membranes to culture cells at high cell density in a flask that can be simply placed into an incubator. An advantage of such a device is the possibility to start from low cell densities (less critical-seeding dose required) and expand cells to high cell numbers with reduced feeding needs compared with the Xuri. Jin J, Sabatino M, Somerville R, Wilson J R, Dudley M E, Stroncek D F et al., "Simplified method of the growth of human tumor infiltrating lymphocytes in gas-permeable flasks to numbers needed for patient treatment," *J Immunother* 2012; 35: 283-292; Bajgain P, Mucharla R. Wilson J, Welch D, Anurathapan U, Liang B et al., "Optimizing the production of suspension cells using the G-Rex 'M' series," *Mol Ther* 2014; 1. A pump allows cell feedings without having to 'open' the closed tubing set. This system requires an incubator to maintain proper gas and temperature control. Nevertheless, open steps are part of this process, such as during inoculation of the flask. The current conventional process of manufacturing gene-modified T cells requires several devices: one to isolate and enrich cells, one to wash and concentrate, one to incubate and/or expand the T cells, implementation of transduction procedures, a microscope to view the cells and so on, depending upon the specific procedure. The use of multiple devices requires significant operator interaction and support. Each device must work seamlessly with the others without interference, personnel must be trained, installation and servicing must be scheduled, operational and performance qualification must be in place before cGMP gene-modified T-cell products can be manufactured.

As described herein, a device for performing one or more methods described throughout this disclosure is, according to an embodiment, capable of performing automatically any and/or all of these steps: from cell preparation, enrichment, activation, transduction, expansion to final formulation and sampling in a closed sterile, single use tubing set. Apel M, Brüning M, Granzin M, Essl M, Stuth J, Blaschke J et al., "Integrated clinical scale manufacturing system for cellular products derived by magnetic cell separation, centrifugation and cell culture," *Chemie Ingenieur Technik* 2013; 85: 103-110. In an embodiment, the device may be used in a clinic for the enrichment of stem cells and the preparation of virus-reactive T cells. It is a platform for integrated and functionally closed manufacturing of engineered T cells with minimal user interaction. This approach simplifies and improves the robustness of the manufacturing process and frees available resources for other tasks.

Another challenge for reproducible production of effector T-cell populations which could benefit from further improvement are in-process control and quality control steps. These are essential in any manufacturing process and should be simplified. Automation can again be of help here, provided the existence of a reliable and safe sampling method. For example, flow cytometric analysis of cultured cell populations would benefit from automated (no-wash) staining, acquisition and analysis processes, as is possible with the MAQSQuant® Express Mode. Clustering programs, that is automated analysis of flow cytometric data, have become powerful and may be preferred over standard user based analysis where harmonization is harder to reach as demonstrated by the results of proficiency panel studies. Aghaeepour N, Finak G, Hoos H, Mosmann T R et al, FlowCAP Consortium, DREAM Consortium, "Critical assessment of automated flow cytometry data analysis techniques," *Nat Methods* 2013; 10: 228-238; McNeil L K, Price L, Britten C M, Jaimes M, Maecker H, Odunsi K et al., "A harmonized approach to intracellular cytokine staining gating: Results from an international multiconsortia proficiency panel conducted by the Cancer Immunotherapy Consortium (CIC/CRI)," *Cytometry A* 2013; 83: 728-738. Automated acquisition and analysis of flow data also presents the possibility to rapidly generate standardized documentation by using LIMS (Laboratory Information and Management System) and significantly reduce workload. Therefore, automated batch recording may be implemented, in an embodiment whenever possible, and can probably most easily be delivered by a one system/device solution with material tracking, ideally in close connection to corresponding in-process control and quality control systems. In an embodiment, this may be imbedded into a full tracking system for the logistic supply chain from sampling of the starting material to the very end of the process, infusion into a patient, for example, in a hospital, institutional setting, or treatment center.

Keeping track of documentation during the manufacturing process is an obligatory and time-consuming task. The implementation of bar code readers permits rapid in-process batch recording of raw materials used during production and can allow a highly standardized protocol to be automatically generated at the end of each run.

Organizing the production of a few dozen cellular products a year can be arranged in a straightforward manner, with limited infrastructure and personnel using the above mentioned methods that are currently in place in a number of centers. However, when implementing manufacturing processes for phase II/III clinical trials with the goal of FDA approval, new sets of challenges arise to produce the hundreds or even thousands of cell therapeutic doses per year that are required. The obligation to entirely avoid any cross contamination between patient products requires working in closed systems (e.g., bags and tubing sets), strict physical separation, decontamination of hoods, incubators and so on for each individual cell product, and the controlled and standardized compounding of reagents (controlling supply, storage of perishables, such as cytokines, large volumes of media and so on) and materials (e.g., plastics). To be successful, gene-modified I-cell therapy must meet these demands and therefore the manufacturing method used must be standardized and scalable.

A solution that can be adapted from other automated industries is the production line, where a specific product moves from one station to the next. Using the devices, systems, and methods described herein, such manufacturing methods can be applied to the production of gene-modified T cells. For example, in an embodiment, the patient's cells would enter the 'processing station' where a skilled operator would have the task to document and prepare (e.g., perform washes, density gradient separation, subset isolation) enriched T cells, as well as activate them (i.e., addition of stimulatory reagent). The cells would then move into a (physically) separated space to be transduced (i.e., addition of viral vector). Line clearance protocols would be followed between the handling of different patients' cell products. In an embodiment, cells would then be placed in an adjacent suite organized to accommodate the expansion of the cells either using individual stations or modular spaces to accommodate the chosen expansion method.

In an additional embodiment using the devices, systems, and methods described herein, one device is dedicated to the production of one patient product at a time. This unit-based production would preferentially be organized in more open areas where an operator could oversee several units at the same time. Such organization assumes that the devices must operate independently, with minimal user interaction and have adequate error handling capacity. In such embodiments, warning indicators for unplanned events (i.e., low temperature detection, or recovery after electrical failure) and/or a redundancy of back up procedures are implemented. Cross-contamination is prevented by physical delimitation of each working unit. Validated barcode systems ensure identification and control of the material involved in a given manufacturing unit and during QC sampling.

Such device-based manufacturing directly relies on the performance and robustness of the chosen device(s), but it has the advantage of being highly adaptable, for example, one functional area of 4-5 devices could rapidly be changed between two protocols by simply using a different program on the device, whereas maintaining the structural organization in place. Typically, in production lines, defects in one position of the chain can affect the rest of the production line as it is a linear process. In a device-based manufacturing, dysfunction of a unit does not impact other products and it can be rapidly exchanged by another device where the process can be resumed.

GMP facilities with many separated class A/B room suites may be limited towards commercial efficiency, for example, in a 2000 m2 facility with, for example, 20 such clean rooms, about 500 cellular products per year can be generated (assuming 25 products manufactured by a 10 day process per room per year). In contrast, 200 automated devices could be placed in the same facility and could process about 5000 corresponding cellular products with fewer personal and lower clean room requirements and thereby costs.

One of the major challenges of bringing personalized cellular products into standard therapy is that the production process is patient specific. Regulatory agencies are very familiar with drug manufacturing, but cellular products have special requirements. Although regulatory authorities are working to define optimal guidelines that can be harmonized, the requirements for clinical manufacturing of ATMP (advanced therapy medicinal products) are becoming clearer. The requirements of ATMP are summarized in the European regulation 1394/2007 where gene therapy medicinal product are now defined (§ 2) (REGULATION (EC) No 1394/2007 on advanced therapy medicinal products). In the USA, the requirements can be found in a 1998 FDA document entitled 'Guidance for Human Somatic Cell Therapy and Gene Therapy'.

If one patient dose equals one product, this also means each patient's product represents an entire manufacturing batch. Therefore, according to an embodiment, an enormous number of QC-samples must be processed in comparison with conventional medicinal approaches. This increased QC sampling could impact the time necessary to release the product and freezing the cells may become necessary in certain circumstances. To prevent contamination and cross contamination of other cell products, a commercial manufacturing process using closed systems is an option to reduce manufacturing costs by working in clean rooms, class 10 000/ISO 7.

Materials used during ex vivo manipulation procedures; for example, as described above, antibodies, cytokines, serum, other chemicals, or solid supports such as beads and especially the virus-based gene vectors can affect the safety, purity and potency of the final therapeutic product. These components should be clearly identified and a qualification program with set specifications should be established for each component to determine its acceptability for use during the manufacturing process.

QC tests and release testing are an essential component of the manufacturing of ATMPs. Because of high complexity, cellular products and their testing have demanding requirements for appropriate in-process and quality control. This is dramatically increased for individualized compared with universal cell products. Individualized cell products are more restricted in the amount of material available for testing and time for which the cell product is available for testing. Furthermore, actual testing must be performed in a timely manner as these products have a limited shelf-life prior to infusion or cryopreservation. Complexity of certain assays, particularly cellular functional assays, can increase the risk of mistakes and generate unreliable data.

One should clearly distinguish the release criteria, which are essential for clearing the cellular product for patient use, from tests 'for information only' which are more research driven and do not relate to patient safety. It is clear, however, that harmonization of quality control assays and criteria for release will help to define and advance cellular therapy. Indeed, the possibility of comparing QC data across different manufacturing sites and different processes worldwide will mean improved and more reliable understanding of the cellular product. Here again automated platforms that adhere to established guidelines will be of great help.

There is a benefit for generating 'universal' cellular products. The manufacturing of such products would be similar to other biologics, such as vaccines and monoclonal antibodies, taking place in single industrial scale manufacturing sites, despite the increased complexity of storage of these products and delivery to the patients.

Instead of one product being manufactured at large scale, and then stored and shipped in individual vials, many similar products would be efficiently produced at small scale, many in parallel with non-synchronous overlapping production slots. The method chosen to produce patient-specific ATMPs, that is, production line or device based, will guide the model of commercial manufacturing. When relying on a multitude of devices and operators to run the process, a critical size infrastructure is important in finding the best balance between costs and production, as well as center location and area coverage for logistics. Appropriate logistics for delivery of the patient-derived starting material to the production facility and back to the patient must cover the harvesting of the starting material at the patient's center-of-care and/or point-of-care, transport, modification and expansion, then storage and transport back to the patient in a totally transparent and traceable manner. Although shipping companies can provide complete solutions for this task including validated cell-shipping and chain-of-custody procedures, it is important to note that the manufacturer is ultimately responsible and has to address this task carefully to ensure maximum product safety.

An alternative to centralized manufacturing models are localized manufacturing options using the devices, systems, and methods described herein, at the patients' point-of-care.

Achieving a high level of product quality with a decentralized manufacturing model requires highly standardized, robust and transparent manufacturing processes and platforms. Transfer of production know-how for the setup of new production facilities is best achieved with highly automated processes for production and IPC/QC as the device and programs that control the runs are identical. However, for an easy transfer and robust operation across several production sites it is important to ensure availability of the same components and reagents to all sites.

Platforms such as the devices, systems, and methods described herein that enable the automated manufacturing of gene-modified T cells from the initial harvest from the patient to the final formulated product are highly exportable. This device-centric approach relies less on infrastructure for the cell processing than production lines and therefore, smaller, more regional facilities can be envisaged. Such regional facilities may now become less difficult to build (smaller, less expensive and with lower needs in terms of cleanroom environment) and could facilitate improved patient scheduling and availability (for sourcing of patient cells and infusion of final product) with local care providers.

In an embodiment, the decentralized manufacturing model applies only for the final steps in the manufacturing process—gene modification of the patients' cells. The manufacture of all non-patient specific components, such as ancillary reagents, viral vectors and so on, will mostly remain centralized as it is closer to a pharmaceutical manufacturing model where one batch is used for many cell product applications.

Using the devices, systems, and methods described herein, gene-modified T cells are manufactured at the point-of-care in a facility in close proximity to, associated with, or at a hospital, institution or treatment center. This may depend on the robustness of patient-specific automated T-cell manufacturing and how the regulatory authorities will ultimately regulate the manufacturing and use of gene-modified T cells. Nevertheless, such a decentralized mode for delivering cell-based drug products to patients will certainly decrease the risks to the product and costs, particularly the to-and-fro transportation costs that are associated with centralized manufacturing facilities. In addition to the increased risk to product integrity and cost, transportation may also compromise the quality of the cell product by necessitating, for example, its freezing for shipping. This would not be the case with local decentralized facilities. Decentralized facilities located in hospitals, institutions, and/or treatment centers, would reduce these risks and also incentivize hospitals to adopt such long-lasting cellular therapies as they would then become a significant part of the value chain. Using the devices, systems, and methods described herein near the point-of-care, where the manufacturing and QC methods are safe and reliable to operate, would be the preferred option for bringing personalized cell therapy to patients with high medical need.

All publications and patent applications and/or patents referred to herein are hereby incorporated by reference in their entirety.

EXEMPLARY EMBODIMENTS

The Examples described below exemplify the apparatus, methods, and systems of embodiments of the invention and are not intended to limit the disclosure of the invention as described herein. This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Viral Transduction of T Cells with Disease-Specific T Cell Receptor Genes

A use according to an embodiment of the invention is the introduction of genes coding for a disease-specific T cell receptor into a polyclonal population of T cells, which may then be used for therapeutic injection into patients. The T cells are directed towards the target antigen, e.g. tumor cell or infected cells.

A centrifugation chamber providing cell modifying surfaces coated with RetroNectin® is supplied with a recombinant virus containing supernatant, wherein the virus encodes the target antigen, and rotated at surfaces by the gravitational forces generated by the rotation. Following this coating step, the chamber is rotated at low rotation speed and the T cells to be modified are introduced into the high rotational speed (e.g. 2000×g) for 2 hours. For improved viral transduction, the T cells are previously activated, e.g. by cultivation in the presence of antibodies against CD3 and CD28, either in the same centrifugation chamber or in a separate device. By centrifugation (e.g. 1000×g for 15 min) the T cells in the chamber come into intimate contact with the virus coated surface, allowing viral transduction. The centrifugation speed is adjusted to optimize the transduction. Transient lowering of the centrifugation speed allows detachment of the cells and subsequent centrifugation at high speed reattaches the cells at another point of the coated surface. This process can be repeated several times, e.g. to achieve multiple interactions of the cells with virus coated surfaces. Following this transduction process the rotation speed is stopped or reduced to a minimum, i.e. sufficient to keep the cells at the cultivation surface. During the process optimal cell culture media, containing appropriate amounts of nutrients and growth factors is added continuously to the chamber via the inlet port of the rotary chamber system. The centrifugation fixes the cells at a certain location, and therefore media can be added and removed without changing the location of the cell, i.e. without interfering with the modification process. The constant exchange of the medium without affecting the cell position, i.e. modification process, also allows to use a minimal medium volume at a given time, i.e. the distance of the cell attached to the culture surface to the gas reservoir/medium surface can be <5 mm. In this way optimal gas supply is guaranteed without the need for a steady state large medium volume, usually used as a reservoir of nutrients.

During the transduction process of high speed and/or lower speed, a steady flow of stimulation media over the cells or cell culture via the inlet and outlet port of the chamber is maintained. This removes transduction inhibitors and improves the target cell viability.

Each transduction process is adjusted to the optimal interaction of the cells with the virus particles (depending on cell and virus type) coated to the surface of the centrifugation chamber or moulded element by adaptation of the centrifugation speed (increasing or reducing the g number) leading efficient, fast, easy and safe handling of the transduction process.

For those embodiments disclosed herein which perform viral transduction of T cells with disease-specific T cell receptor genes, computer-executable instructions stored on one or more memories may be executed to cause one or more hardware components of a device as described herein to perform one or more operations described above.

Example 2

Activation and Expansion of Antigen-Specific T Cells

T cells can be activated and expanded by antigens loaded in or on antigen-presenting cells (APC). T cell activation requires intimate contact between the T cells and APC.

To improve T cell activation a system described herein is used to spin down APC and T cells in an appropriate ratio, e.g. 1:100 to 100:1. Either physiological cell mixtures such as PBMC, containing T cell and APC or defined cell preparations, e.g. purified T cells and APC, e.g. dendritic cells, B cells, macrophages, cell lines transfected with distinct MI-IC molecules, etc., mixed at an appropriate ratio are used. In addition antigens, proteins, peptides, cell lysates, and growth factors and/or co-stimulatoty antibodies, e.g. anti CD28, antiCD137, may be added. The contact between the cells is rapidly induced and maintained at an appropriate level by centrifugation.

APC and T cells can be deposited in distinct layers, e.g. T cell on top of a layer of APC, enabling optimal contact of T cells to APC. In conventional culturing devices, cells slowly sediment in an uncontrolled fashion providing asynchronous and only suboptimal contact between APC and T cells. During cultivation centrifugation fixes the cells at a distinct position and therefore media, growth factors, co stimulatory molecules or antigens can be added in a controlled fashion without disturbing the cellular interaction. By changing the centrifugational speed the interaction between the cells is modulated at different phases of the culturing process, e.g. inducing firm contact at an early phase and reduced contact at later phases. This results in an accelerated and synchronous and more pronounced activation of T cells and in addition allows optimal control of the cellular microenvironment in terms of cellular composition, supply with nutrients, growth factors etc. Under these conditions the rapid and controlled activation of antigen-specific T cells is achieved.

The activated T cells are further purified, e.g. based on the expression of activation markers, such as cytokines, CD154 or CD137 by magnetic cell separation. Such cells can be generated against various antigens, e.g. pathogens, tumors or, in case of regulatory T cells against auto antigens. These cells can be used for cellular therapies.

A particular advantage of such embodiments of the invention is that the whole cell cultivation process including all described manipulations required to achieve optimal results can be performed in a closed system, i.e. with minimal risk of contaminations.

For those embodiments disclosed herein which perform activation and expansion of antigen-specific I cells, computer-executable instructions stored on one or more memories may be executed to cause one or more hardware components of a device as described herein to perform one or more operations described above.

Example 3

Polyclonal Activation and Expansion of T Cells

Systems according to an embodiment of the invention provide an optimized platform for polyclonal activation and expansion of T cells, comprising conventional T cells or regulatory T cells.

This example is similar to Example 2 except that instead of defined antigen, polyclonal stimuli are used, comprising antibodies against CD3 and co-stimulatory molecules, such as CD28 and/or CD137. These antibodies are added either in soluble form, requiring the addition of accessory cells bearing Fc-receptors, e.g. conventional antigen-presenting cells or cell lines transfected with Fc-receptors. Alternatively the added antibodies are immobilised on a macroscopic surface, e.g. a particle or bead ranging from about 30 nm to 100 μm. These immobilised antibodies are directly cultured with purified T cells, e.g. at ratios 1:4 to 4:1. As described above, in an embodiment, the system used allows regulated contact of T cells and stimulating agent and controlled addition of additional environmental factors, e.g. nutrients, cytokines, etc.

The polyclonal populations of T cells generated can be used in cellular therapies, e.g. polyclonal regulatory T cells for treatment of autoimmune or graft versus host disease or the prevention of organ transplantation.

For those embodiments disclosed herein which perform polyclonal activation and expansion of T cells, computer-executable instructions stored on one or more memories may be executed to cause one or more hardware components of a device as described herein to perform one or more operations described above.

Example 4

RBC Depletion Method and Computer-Executable Instructions Therefor

Referring now to FIGS. 11A and 11B, another exemplary RBC depletion method 200 may include mixing the sample with a hetastarch in saline (HES) solution within a treatment chamber at block 202 and as indicated by arrow 252 which corresponds to a sample input and 254 which corresponds to a media input. Block 202 may also include adding a buffer solution to the treatment chamber as indicated by arrow 256 which corresponds to a buffer input. Specific amounts of HES and/or buffer to add at block 202 may be determined based on the initial volume of the sample and/or a maximum volume of the treatment chamber. For example, in particular embodiments if the sample has a hematocrit level above 25% it may be diluted with 20% volume HES and buffer (e.g. PBS/EDTA) up to a maximum volume of the treatment chamber, e.g. 300 ml.

At block 204, rouleau of the RBCs can be initiated. In particular embodiments, rouleau is initiated by performing slow centrifugation (e.g., 35-45×g or 40×g) within the treatment chamber. It should be appreciated that the intended g force, e.g. 35-45 g, can be calculated based on the rotational speed of the centrifuge (rpm) and the radius of rotation. At block 206, sedimentation of the RBCs is initiated by transferring the sample from the treatment chamber to a sedimentation bag as indicated by arrow 258. In particular embodiments, a determination is made at decision block 208 as to whether a sufficient amount of sedimentation has occurred. Such a determination may be made by receiving a user input from a user whom has visually examined the sedimentation bag and contents thereof. In particular embodiments, if sufficient sedimentation has not yet occurred then the method proceeds along the arrow labeled "No" and later returns to block 208. In contrast, if sufficient sedimentation has occurred the method may proceed to block 210 at which the RBC-rich fraction of the blood sample, e.g. that fraction which has formed as sediment within the sedimentation bag, is removed from the sedimentation bag as indicated by arrow 260. In particular embodiments, the RBC-fraction removal is performed in a stepwise fashion by user defined volumes until the desired RBC pellet size is reached. For example, with particular reference to FIG. 11C, a sample may be transferred to a funnel shaped sedimentation bag in which Rouleau and sedimentation is to occur. As time progresses from t=0 to t=N the RBC-fraction forms an increasingly concentrated sediment/pellet. In particular embodiments, a funnel shaped sedimentation bag which includes volume demarcations (as illustrated in FIG. 11C) may be visually inspected once an appropriate amount of sedimentation has occurred and the user may enter a user defined volume corresponding to the RBC pellet which is then transferred from the sedimentation bag while the target cell fraction remains in the sedimentation bag. It should be appreciated that the target cell fraction may include platelets or other blood components. In particular embodiments, the instructions 270 may include default amounts of time for sedimentation and default volumes to be removed at specific times, e.g. the instructions may be programed to remove a 50 ml_ or 75 ml_ or 100 ml_ 30 minutes after the sample is transferred to the sedimentation bag.

At block 212, the sample (e.g. the RBC depleted fraction) is transferred back into the first treatment chamber as indicated by arrow 262 for supernatant washing. While the depicted use of the treatment chamber is preferred, in particular embodiments the device may include one or more supplemental treatment Chambers, for example, supernatant washing. Supernatant washing may remove any unwanted component of the sample such as, for example, residual HES from block 202. For example, buffer may be again added to the sample in the treatment chamber wherein centrifugation is performed to wash out residual HES. At block 214, the RBC depleted fraction of the sample may be concentrated to a desired volume for subsequent processing. For example, the RBC depleted fraction may undergo centrifugation to remove buffer while leaving the target cells in the treatment chamber. Block 214 may also optionally include aspiration.

For those particular embodiments disclosed herein which perform red blood cell (RBC) depletion, computer-executable instructions stored on one or more memories may be executed to cause one or more hardware components of a device as described herein to perform one or more steps described in relation to FIGS. 11A and 11B. Exemplary description of computer-executable instructions are denoted herein as SW1 and are described in the following table 1.

TABLE 1

Exemplary description of computer-executable RBC depletion instructions.

SW1 Description 1. RBC depletion of bone marrow or peripheral blood
SW1 Description 2. RBC depletion of bone marrow or peripheral blood. Starting sample at <25% HCT is mixed with HES and buffer depending on initial product volume. Each stage has

TABLE 1-continued

Exemplary description of computer-executable RBC depletion instructions.

a maximum volume and includes rouleau induction, followed by transfer of product to a sedimentation bag. Following sedimentation, RBC-rich fraction removal is initiated until a selected RBC pellet size is reached. Following completion of RBC removal, supernatant washing is initiated to remove residual HES. The RBC depleted fraction remains in the device chamber for labeling.

SW1 Description 3. RBC depletion of bone marrow or peripheral blood. Starting bone sample at <25% HCT is mixed with 20% volume HES and PBS/EDTA buffer depending on initial product volume. Each stage has a maximum volume of 300 ml_ and includes a slow centrifugation step to initiate rouleau, followed by slow transfer of product to a sedimentation bag. Following a desired sedimentation time, the user is prompted to initiate RBC-rich fraction removal until the desired RBC pellet size is reached. Once the user confirms completion of RBC removal, the program automatically initiates supernatant washing to remove residual HES. Once washing is complete, the RBC depleted fraction is concentrated and remains in the device chamber.

SW1 Description 4. This program is suitable for RBC depletion of bone marrow or peripheral blood of initial volume >10 ml_. Starting bone sample at <25% HCT is mixed with 20% volume HES and Buffer (e.g. PBS/EDTA) in stages depending on initial product volume. Each stage has a maximum volume of 300 mL and includes a slow centrifugation step to initiate rouleau, followed by slow transfer of product to funneled sedimentation bag provided by the user. Minimum sedimentation wait is 30 minutes and can be prematurely terminated or extended infinitely by the user through a touchscreen interface. Following a desired sedimentation time, the user can be prompted to initiate RBC-rich fraction removal in a stepwise fashion by user-defined volumes until the desired RBC pellet size is reached. Once the user confirms completion of RBC removal, the program automatically initiates supernatant washing in Buffer (e.g. PBS/EDTA) to remove residual HES. Once washing is complete, the RBC depleted fraction is concentrated to the desired volume for bead labeling (90 ml_) through a centrifugation and aspiration step and remains in the device chamber.

Example 5

Cell Labeling Method and Computer-Readable Instructions Therefor

Referring now to FIGS. 12A and 12B, an exemplary platelet removal and target cell selection method 300 may include diluting a cell fraction with a buffer as indicated by arrow 350. The buffer that is combined with the cell fraction at block 302 may or may not be the same buffer product(s) included in FIGS. 11A and 11B. In particular embodiments, the cell fraction is diluted in a buffer (e.g. PBS/EDTA) prior to being pelleted at block 304 to remove platelets and/or any other samples which may interfere with subsequent selection/isolation. It should be appreciated from FIG. 12A that the pelleting of the cell fraction at block 304 may include centrifuging the cell fraction (e.g. the remaining portion of the original sample such as the RBC-rich fraction if RBC depletion has been performed) within the treatment chamber and, once pelleted, transferring the blood platelets from the treatment chamber to a waste receptacle, e.g. a waste bag, as indicated by arrow 352. In particular embodiments wherein the sample is an apheresis product, platelet removal may be preferably performed prior to target cell selection, concurrently with target cell selection, after target cell selection, or any combination thereof.

At block 306 a primary labeling agent may be added to the cell fraction as indicated by arrow 356. It should be appreciated from the foregoing disclosure that the primary labeling agent may include directly-conjugated immunomagnetic beads. It should be appreciated that the primary labeling agent and/or secondary labeling agent (if applicable) which may optionally be introduced at block 314 each may be added directly to the treatment chamber. Accordingly, in particular embodiments the same treatment chamber which may be used for RBC and/or platelet removal may be used for labeling the remaining target cells. In this way, the method achieves a highly sensitive and complex objective with minimal equipment and/or opportunities for contamination. In particular, as should be appreciated based on the disclosure herein, the entire method may be performed within a closed circuit in preferred embodiments.

At block 308, an incubation environment may be maintained within the treatment chamber to facilitate binding of the primary labeling agent with the target cells. In particular embodiments, at least part of the incubation environment is maintained for each component of the system of FIG. 12A (and FIGS. 11A, 13A, and 14A for that matter). For example, the incubation environment may be maintained within a boundary 358 which encapsulates some or all of the components of the system. For example, boundary 358 may include a glass hood which covers the system components including the treatment chamber and/or any other components such as a closed sample circuit (e.g. tubing corresponding to arrows 350, 352, 354, and 356) and containers of various products used in particular embodiments, e.g. a buffer bag or labeling agent bag. In particular embodiments, the treatment chamber is enclosed within a boundary 360 which does not enclose all other system components. Furthermore, particular embodiments include each of boundary 358 and boundary 360.

In particular embodiments, maintaining the incubation environment at block 308 includes controlling a temperature of the treatment chamber at block 310 as indicated by the thermometer symbol of FIG. 12A. For example, one or more heating or cooling units may be enclosed within the boundary 360. Furthermore, in particular embodiments, fluids and/or gases entering the treatment chamber may be passed through a heat exchange unit to quickly obtain a desired temperature. For example, in particular embodiments, the cell fraction within the treatment chamber may be maintained at 2-25 degrees Celsius during the incubation period in which the labeling agent(s) are reacting with the target cells.

In particular embodiments, maintaining the incubation environment at block 308 includes agitating the cell fraction at block 312. For example, in embodiments wherein the treatment chamber is configured to perform centrifugation the treatment chamber may spin at a slow speed to agitate or mix up the contents thereof. In particular embodiments, agitating the cell fraction at block 312 may be performed continuously. For example, the treatment chamber may continuously switch between spinning clock-wise and counter-clockwise as indicated by the alternating arrows about the vertical axis of FIG. 12A. In particular embodiments, the agitating the cell fraction may be performed on a predetermined period, e.g. 10 seconds of continuous agitation every 30 seconds such that each agitation cycle is followed by 20 seconds of non-agitation. Any other appropriate time intervals may also be used.

In particular embodiments, one or more secondary labeling agents may be added at block 314. For example, various embodiments may target more than one discrete type of cell and, therefore, may require more than one type of labeling agent to select the target cells. It should be appreciated that the addition of one or more secondary labeling agents may occur simultaneously with the addition of the primary labeling agent at block 306 and/or the maintaining of the incubation environment at block 308. Alternatively, the addition of one or more secondary labeling agents at block 314 may occur subsequent to the addition of the primary labeling agent at block 306. It should further be appreciated that in various embodiments the operation at block 314 is omitted, e.g. only a primary labeling agent is added.

At block 316, excess labeling agent may be separated from the cell fraction by removing the excess labeling agent from the treatment chamber without removing the cell fraction from the treatment chamber. For example, the contents of the treatment chamber including both the labeled cell fraction as well as the excess labeling agent may be centrifuged to separate these components into discrete layers and the layer corresponding to the excess labeling agent may be removed.

In particular embodiments, the labeled cell fraction may be concentrated at block 318 to a predetermined and/or user specified cell density appropriate for separating the target cells from the remaining non-target cells within the labeled cell fraction using the preferred separation method. Concentrating the cell fraction may be desirable when a target cell separator is likely to function with greater efficiency if the labeled cell fraction is passed through the target cell separator at a lower speed. For example, in an implementation wherein the target cell separator is a magnetic-activated cell sorter which uses a magnetic field to restrict magnetically labeled target cells from flowing through a magnetic separation column the slower the labeled cells pass through the sorter the more likely they may be to be retained within the target cell separator. Thus, reducing the volume of the cell fraction without removing labeled cells, i.e. concentrating the cell fraction, may improve subsequent target cell separation. Furthermore, in particular embodiments, a cell concentration which is too high may prevent instrumentation from operating properly, e.g. magnetic activated cell sorting (MACS) columns or fluorescence activated cell sorting (FACS) machines may clog-up. Moreover, if FACS-based sorting of labeled cells is desired, high cell densities can cause inclusion of non-labeled cells during separation.

It should be appreciated that labeling the target cells may be performed using a labeling agent which selectively binds with target cell(s) and/or non-target cell, e.g. selecting a negative fraction. In particular embodiments, selectively binds means that a bead, antibody, or other binding moiety binds to a marker on a cell (e.g., CD3, CD4, CD8, CD13, CD14, CD15, CD16, CD19, CD20, CD34, CD45, CD45RA, CD45RO, CD49f, CD50, CD56, CD71, CD90, CD133) with a dissociation constant (1(D)) of $10^{-5}$ M or less, in particular embodiments of from $10^{-5}$ M to $10^{-13}$ M, or particular embodiments of from $10^{-5}$ M to $10^{-10}$ M. In particular embodiments, selectively binds means that a bead or antibody binds to a marker on a cell with a dissociation constant (1(D)) of $10^{-7}$ M or less, or in particular embodiments of from $10^{-7}$ M to $10^{-12}$ M, or in particular embodiments of from $10^{-7}$ M to $10^{-15}$ M. However, it should further be appreciated that labeling the target cells may also be performed without a labeling agent. For example, a target cell may be considered "labeled" based on an ability to distinguish and/or sort the target cells based on any identifying characteristic. In particular embodiments, one or more characteristics may be determined with regard to target cells and non-target cells as they pass between a light source and a light detector, e.g. as configured on a fluorescence-activated cell sorter, and an electrical charge (positive or negative) may be induced onto the target cells and/or non-target cells. Thus, in particular embodiments, target cells which have had a charge induced thereon may be considered labeled.

It should further be appreciated that computer-executable instructions stored on one or more memories may be executed to cause one or more hardware components of a point-of-care and/or portable target cell gene therapy device such as embodiments described herein to perform one or more steps described in relations to FIGS. 12A and 12B. Exemplary description of computer-executable instructions for cell labeling (target or non-target for positive or negative selection) are denoted herein as one or both of SW1 and/or SW2 and are described in the following table 2.

TABLE 2

Exemplary description of computer-executable cell labeling instructions.

SW2 Description 1. Labeling of any desired cell fraction
SW2 Description 2. Labeling of any desired cell fraction with a directly-conjugated immunomagnetic bead.
SW2 Description 3. This program is suitable for labeling of any desired cell fraction with a directly-conjugated immunomagnetic bead or fluorophore-conjugated antibody(ies). The program initiates with the assumption that the cell product to be labeled is in the device chamber. The cell fraction to be labeled is first diluted in buffer and then is pelleted. Immunomagnetic beads or fluorophore-conjugated antibodies with or without blocking agent are then added and the chamber is cooled and gently shaken for an incubation period. Following incubation non-bound excess beads/antibodies are removed. Once washing is complete, labeled cell fraction remains in device chamber.
SW2 Description 4. This program is suitable for labeling of any desired cell fraction with a directly-conjugated immunomagnetic bead or fluorophore-conjugated antibody(ies). The program initiates with the assumption that the cell product to be labeled is in the device chamber. The cell fraction to be labeled is first diluted in buffer and then is pelleted. Immunomagnetic beads (up to 15 mL) or fluorophore-conjugated antibody (up to 10 mL) with TABLE 2-continued Exemplary description of computer-executable cell labeling instructions.

or without blocking agent are then added and the chamber is covered to restrict light exposure, cooled to 2-25° C. and gently shaken for a total incubation period of 30 minutes. Following incubation the labeled cell fraction is centrifuged and washed to remove non-bound excess beads or antibodies. Once washing is complete, labeled cell fraction is concentrated to desired volume and remains in device chamber.
SW3 Description 1. This program is suitable for two-step labeling of any desired cell fraction with a primary antibody/labeling agent followed by a secondary-antibody/agent magnetic bead. The program initiates with the assumption that the cell product to be labeled is in the device chamber.
SW3 Description 2. This program is suitable for two-step labeling of any desired cell fraction with a primary antibody/labeling agent followed by a secondary-antibody/agent or magnetic bead. The program initiates with the assumption that the cell product to be labeled is in the device chamber. The volume to be labeled is set to allow adjustment of cell, antibody and/or bead concentrations to desired values. The cell fraction to be labeled is diluted in Buffer and then is pelleted. Supernatant is removed to bring the labeling volume to the desired value. The primary antibody/agent with or without blocking agent is then added for an incubation period. The secondary antibody/agent magnetic beads are then added for a second incubation period. Following incubation the labeled cell fraction is washed to remove non-bound excess antibody/agent/beads.
SW3 Description 3. This program is suitable for two-step labeling of any desired cell fraction with a primary antibody/labeling agent followed by a secondary-antibody/agent magnetic bead. The program initiates with the assumption that the cell product to be labeled is in the device chamber. The volume to be labeled is set by the user to allow adjustment of cell, antibody and bead concentrations to desired values. The cell fraction to be labeled is first diluted in Buffer (e.g. PBS/EDTA) and then is pelleted. Supernatant is removed to bring the labeling volume to the desired value. The primary antibody/agent with or without blocking agent is then added and the chamber is gently shaken for a total incubation period. The secondary antibody/agent magnetic beads are then added, and the chamber is gently shaken for a second incubation period. Following incubation the labeled cell fraction is centrifuged and washed to remove non-bound excess antibody/agent/beads. Once washing is complete, labeled cell fraction is concentrated to desired volume for enrichment and remains in device chamber.
SW3 Description 4. This program is suitable for two-step labeling of any desired cell fraction with a primary antibody/labeling agent followed by a secondary-antibody/agent magnetic bead. The program initiates with the assumption that the cell product to be labeled is in the device chamber. The volume to be labeled is set by the user to allow adjustment of cell, antibody and bead concentrations to desired values. The cell fraction to be labeled is first diluted in Buffer (e.g. PBS/EDTA) and then is pelleted in a step-wise fashion. Supernatant is removed to bring the labeling volume to the desired value input by the user. The primary antibody/agent with or without blocking agent is then added and the chamber is cooled to 2-25° C. and gently shaken every 30 seconds for a total incubation period of 30 minutes. The secondary antibody/agent magnetic beads are then added, chamber temperature is maintained at 2-25° C. and the chamber is gently shaken every 30 seconds for a second incubation period of 30 minutes. Following incubation the labeled cell fraction is centrifuged and washed to remove non-bound excess antibody/agent/beads. Once washing is complete, labeled cell fraction is concentrated to desired volume for enrichment and remains in device chamber.

Example 6

Target Cell Selection Method and Computer-Executable Instructions Therefor

Referring now to FIGS. 13A and 13B, an exemplary target cell selection method 400 may include priming a target cell selector such as a MACS based cell selector with a buffer as indicated by arrow 450. For example, a magnetic column and pre-column of MACS based target cell selector have a buffer (e.g. PBS/EDTA) pumped through it prior to being powered on, e.g. caused to generate a magnetic field, at block 404 and/or loaded with the labeled cell fraction at block 406. In particular embodiments, the priming at block 402 occurs following the powering up of the cell sorter at block 404 or does not occur at all, e.g. the cell sorter is not primed.

At block 406, the target cell selector is loaded with the prepared (e.g., labeled) cell fraction as indicated by arrow 452. For example, the contents of the treatment chamber including the target cells, which in particular embodiments have been labeled, are passed through the target cell selector. In particular embodiments using MACS sorting technology wherein target cells have been magnetically labeled with immunomagnetic beads the target cells may become magnetically bound to a portion of the target cell selector. Alternatively, non-target cells may be labeled such that target cells are isolated causing non-target cells to bind to the target cell selector while allowing target cells to pass through. Non-target cells and other "pass-through" components of the labelled cell fraction may be collected in one or both of a non-target cell receptacle as indicated by arrow 454 and/or a waste receptacle as indicated by arrow 456.

In embodiments using MACS-based cell selection, the bound cells may be washed and/or eluted at block 408. As described elsewhere herein, it should be appreciated that target cell selection at block may utilize non-MACS based technology, e.g. flow cytometry. Accordingly, in particular embodiments target cells would not be "bound," e.g. there would be no immunomagnetic beads used to label the target cells.

At block 410, the sorted cells may be reloaded onto the cell separator as indicated by arrow 458. Reloading the cell separator with the already sorted cell fraction may increase the selection/isolation (e.g., purity) of the final sorted cell fraction. In particular embodiments, the reloading the sorted cell fraction at block 410 occurs at a slower transfer rate than the initial loading at block 406.

At block 412, components which are removed during the washing and/or eluting at block 406 (if applicable) may be collected in a waste receptacle or bag as indicated by arrow 456.

In particular embodiments, the target cell selector may be powered down at block 414. For example, in embodiments using MACS sorting technology powering down the target cell selector at block 414 may terminate generation of a magnetic field to released selected/isolated target cells which are bound to the target cell separator. At block 416, target cells may be collected by transferring them to one or more of a target cell receptacle (e.g. the bag labeled "Target Cells" of FIG. 4A) and then from the target cell receptacle into the treatment chamber as indicated by arrows 460. Exemplary description of computer-executable instructions that may be performed by a device as described herein are denoted herein as SW4 and are described in the following table 3.

treatment chamber), and expansion has taken place if applicable, a desired nucleic acid can be introduced to target cells as indicated by arrow 460.

At block 602, an optimal or desired target cell suspension volume may be determined. For example, the volume of the cell suspension which was transferred to the treatment chamber at arrow 460 may be determined. In particular embodiments, the determination at block 602 is received via a user input. For example, a user may examine the target cell suspension that is in the treatment chamber and estimate its volume. In particular embodiments, the treatment chamber may include a visual aid 650 to assist the user in determining the volume at block 602. For example and with particular reference to FIG. 14A, the visual aid 650 may enable the user to compare the height of the cell suspension (as indicated by the dashed line) with the visual aid 650. Although the visual aid 650 is illustrated in the form of

TABLE 3

Exemplary description of computer-executable selection/isolation instructions.

SW4 Description 1. This program is suitable for selection of any labeled cell fraction.
SW4 Description 2. This program is suitable for magnetic column based selection of any labeled cell fraction. The program initiates with the assumption that the labeled cell fraction to be selected is in the device chamber. If magnetic bead-based selection, a magnetic column and pre-column on the device are primed with buffer. The cell fraction to be selected is passed through the pre-column and over the magnetic column with the magnet turned on. Cells bound to the column are released and collected. If FACS-based sorting, the sorter is primed with buffer. Cells are passed through the sorter and labeled cells are included/excluded in the sorted population based on positive or negative selection.
SW4 Description 3. This program is suitable for magnetic column based selection of any labeled cell fraction. The program initiates with the assumption that the labeled cell fraction to be selected is in the device chamber. A magnetic column and pre-column on the device are primed with buffer. The cell fraction to be selected is passed through the pre-column and over the magnetic column with the magnet turned on. Any component of the labeled fraction which does not bind to either the pre-column or the magnetic column (termed "flow-through") is collected. Following column loading, bound cells are washed, eluted and re-loaded onto the column to increase purity of the enriched fraction. Cells bound to the column are released and collected.
SW4 Description 4. This program is suitable for magnetic column based selection of any labeled cell fraction. The program initiates with the assumption that the labeled cell fraction to be selected is in the device chamber. A magnetic column and pre-column on the device are primed with Buffer (e.g. PBS/EDTA). The cell fraction to be selected is passed through the pre-column and over the magnetic column with the magnet turned on. Any component of the labeled fraction which does not bind to either the pre-column or the magnetic column (termed "flow-through") is collected in a bag included in the pre-fabricated tubing set. Following column loading, bound cells are washed, eluted and re-loaded onto the column at slow speed to increase purity of the enriched fraction. Any component of the labeled fraction which is removed during the wash steps is collected in the waste bag included in the pre-fabricated tubing set. Finally, the magnet is turned off and cells bound to the column are released and collected into a bag included in the pre-fabricated tubing set. The final elution volume is 45 mL.
SW4 Description 5. This program is suitable for magnetic column based selection of any labeled cell fraction. The program initiates with the assumption that the labeled cell fraction to be selected is in the device chamber. A magnetic column and pre-column on the device are primed with Buffer (e.g. PBS/EDTA). The cell fraction to be selected is passed through the pre-column and over the magnetic column with the magnet turned on. Any component of the labeled fraction which does not bind to either the pre-column or the magnetic column (termed "flow-through") is collected in a bag labeled "Negative Fraction Bag" included in the pre-fabricated tubing set. Following column loading, bound cells are washed, eluted and re-loaded onto the column at slow speed to increase purity of the enriched fraction. Any component of the labeled fraction which is removed during the wash steps is collected in the Waste Bag included in the pre-fabricated tubing set. Finally, the magnet is turned off and cells bound to the column are released and collected into the bag labeled "Target Cell Bag" included in the pre-fabricated tubing set. The final elution volume may be 45 mL.

Example 7

Nucleic Acid Introduction and Computer-Executable Instructions Therefor

Referring now to FIGS. 14A and 14B, once the target cells are transferred back into a treatment chamber (e.g., the first tick-marks, it should be appreciated that the visual aid may take other forms. In particular embodiments, the determination may be made automatically without user input. For example, in embodiments wherein the treatment chamber is configured to perform centrifugation and is equipped with a camera to identify layers formed during centrifugation then the determination at block 602 may be made by centrifuging the cell suspension and identifying a boundary formed between the cell suspension and a gaseous volume of the treatment chamber.

In particular embodiments, the desired target cell suspension volume is independent of the initial volume of the target cell suspension transferred to the treatment chamber at block 460. For example, in particular embodiments a user may specify a desired target cell suspension volume at block 602.

At block 604, an optimal nucleic acid carrier volume may be determined. The optimal nucleic acid carrier volume may be determined based on a target ratio of nucleic acid molecules to target cells. For example, if a target ratio is 20 nucleic acid molecules per target cell then a known or estimated concentration of nucleic acid molecules per unit volume of suspension may be used in conjunction with the volume determination made at block 602 and a known or estimated concentration of target cells per unit volume of target cell suspension to determine the optimal nucleic acid molecule carrier volume at block 604. Ideally, the total volume of carrier should not exceed 30% of the culture volume to avoid cellular toxicity. The user can define the target culture volume to achieve optimal cell concentrations. For CD34÷ HSPC, acceptable cell concentrations are 1-2 million cells per nil of culture media and vector volume.

In particular embodiments, the determination of block 602 and/or 604 may occur prior to, simultaneous with, or after the target cell suspension is transferred into the treatment chamber.

At blocks 606 through 610 a media exchange is performed during which one or more volumes of a specified media are introduced to the target cell suspension within the treatment chamber. In particular, at block 606 a first volume of a specified media may be introduced to the target cell suspension as indicated by arrow 652. In particular embodiments, introducing media to the target cell suspension at block 606 may include agitation of the target cell suspension within the media. For example, an agitation action similar to that of block 312 may occur to facilitate sufficient contact between the target cells and the specified media. At block 608, the contents of the treatment chamber including both the target cells and media may be centrifuged to pellet the cells within the suspension. In particular embodiments, the centrifugation at block 608 is performed in a step-wise fashion. At block 608, the formed supernatant may be removed from the treatment chamber. For example, in embodiments wherein the supernatant is substantially includes the specified media, the media may be removed at block 610. In particular embodiments, the removed media is transferred to a waste receptacle to be subsequently discarded as indicated by arrow 654.

At block 612, the media exchange of blocks 606 through 610 may be repeated. In particular embodiments, the media exchange may be performed a plurality of times (e.g., 2, 3, 4, 5, 6, 7, 8, 9, or more than 10 times), e.g. repeated at block 612 twice, prior to introducing any genetic modifiers to the target cell suspension. In particular embodiments, a user-defined final cell suspension volume is obtained. For example, a user may determine and/or define an optimal nucleic acid carrier volume at block 604 which is then obtained during the final performance of block 610.

At block 614, a genetic modifier may be introduced to the target cell suspension. In particular embodiments, the nucleic acid carrier may be introduced directly into the treatment chamber.

Numerous techniques for the introduction of one or more genetic modifiers genetic modifications into cells can be used, provided that the necessary developmental and physiological functions of the recipient cells are not disrupted. See e.g., Loeffler and Behr, 1993, *Meth. Enzymol.* 217:599-618; Cohen, et al., 1993, *Meth. Enzymol.* 217:618-644; Cline, 1985, *Pharmac. Ther.* 29:69-92). In particular embodiments, the technique should provide for the stable transfer of nucleic acid to the cell, so that the nucleic acid is expressible by the cell and preferably heritable and expressible by its cell progeny.

Exemplary methods include transfection, electroporation (as described previously), microinjection, liposomes/lipofection (Tarahovsky and Ivanitsky, 1998, *Biochemistry* (Mow) 63:607-618), ribozymes (Branch and Klotman, 1998, *Exp. Nephrol.* 6:78-83), calcium phosphate mediated transfection, infection with a viral or bacteriophage vector containing the gene sequences, cell fusion, chromosome-mediated gene transfer, microcell-mediated gene transfer, sheroplast fusion, administration of naked DNA, DNA complexes and/or triplex DNA (Chan and Glazer, 1997, *J. Mol. Med.* 75:267-282), transposons/transposases, etc.

Within the treatment chamber, genetic modifications can be induced with a genetic modifier. In the case of naked DNA, DNA complexes and/or triplex DNA, for example, the carrier can be a liquid. As is understood by one of ordinary skill in the art, carriers also include liposomes, vectors, etc. It should be appreciated that, in additional to other genetic modifiers disclosed throughout the disclosure, a genetic modifier may also include one or more of naked DNA, naked mRNA, an adenoviral vector, or an adeno-associated vector, guide RNA (for example, for CRISPR applications), zinc fingers, meganucleases, TALENs, meganuclease-TALEN fusions (megaTALs), and/or genes flanked by regions of homology. Regions of homology may be any suitable length such as, for example, 100 bp to 30,000 bp (e.g., at least 500 bp, at least 1,000 bp, at least 2,000 bp, at least 5,000 bp, at least 10,000 bp, or at least 20,000 bp). Any length suitable to drive integration into the genome of the target cell and resulting genetic modification may be used.

A "vector" is a nucleic acid molecule that is capable of transporting another nucleic acid. Vectors may be, e.g., viruses, phage, a DNA vector, a RNA vector, a viral vector, a bacterial vector, a plasmid vector, a cosmid vector, and an artificial chromosome vector. An "expression vector" is any type of vector that is capable of directing the expression of a protein encoded by one or more genes carried by the vector when it is present in the appropriate environment.

Viral vectors are usually non-replicating or replication-impaired vectors, which means that the viral vector cannot replicate to any significant extent in normal cells (e.g., normal human cells), as measured by conventional means (e.g. via measuring DNA synthesis and/or viral titer). Non-replicating or replication-impaired vectors may have become so naturally (i.e., they have been isolated as such from nature) or artificially (e.g., by breeding in vitro or by genetic manipulation). There will generally be at least one cell-type in which the replication-impaired viral vector can be grown-for example, modified vaccinia Ankara (MVA) can be grown in CEF cells. Typically, viral vectors are incapable of causing a significant infection in a subject, typically in a mammalian subject.

"Retroviruses" are viruses having an RNA genome. In particular embodiments, a retroviral vector contains all of the cis-acting sequences necessary for the packaging and integration of the viral genome, i.e., (a) a long terminal repeat (LTR), or portions thereof, at each end of the vector; (b) primer binding sites for negative and positive strand DNA synthesis; and (c) a packaging signal, necessary for the incorporation of genomic RNA into virions. More detail regarding retroviral vectors can be found in Boesen, et al., 1994, *Biotherapy* 6:291-302; Clowes, et al., 1994, *J. Clin. Invest.* 93:644-651; Kiem, et al., 1994, *Blood* 83: 1467-1473; Salmons and Gunzberg, 1993, *Human Gene Therapy* 4: 129-141; Miller, et al., 1993, *Meth. Enzymol.* 217:581-599; and Grossman and Wilson, 1993, *Curr. Opin. in Genetics and Devel.* 3: 1 10-1 14.

"Gammaretroviruses" refers to a genus of the retroviridae family. Exemplary gammaretroviruses include mouse stem cell virus, marine leukemia virus, feline leukemia virus, feline sarcoma virus, and avian reticuloendotheliosis viruses.

Widely used retroviral vectors include those based upon murine leukemia virus (MuLV), gibbon ape leukemia virus (GaLV), simian immunodeficiency virus (Sly), human immunodeficiency virus (HIV), and combinations thereof (see, e.g., Buchscher et al., *J. Virol.* 66:2731-2739, 1992; Johann et al. *J. Virol.* 66: 1635-1640, 1992; Sommerfelt et al., *Virol.* 176:58-59, 1990; Wilson et al., *J. Virol.* 63:2374-2378, 1989; Miller et al. *J. Virol.* 65:2220-2224, 1991; and PCT/US94/05700).

Particularly suitable are lentiviral vectors. "Lentivirus" refers to a genus of retroviruses that are capable of infecting dividing and non-dividing cells and typically produce high viral titers. Lentiviral vectors have been employed in gene therapy for a number of diseases. For example, hematopoietic gene therapies using lentiviral vectors or gamma retroviral vectors have been used for x-linked adrenoleukodystrophy and beta thalassaemia. See, e.g., Kohn et al., *Clin. Immunol.* 135:247-54, 2010; Cartier et al., *Methods Enzymol.* 507: 187-198, 2012; and Cavazzana-Calvo et al. *Nature* 467:318-322, 2010. Several examples of lentiviruses include HIV (human immunodeficiency virus: including HIV type 1 and HIV type 2); equine infectious anemia virus; feline immunodeficiency virus (FIV); bovine immune deficiency virus (BIV); and simian immunodeficiency virus (SIV).

In particular embodiments, other retroviral vectors can be used in the practice of methods in accordance with embodiments of the invention. These include, e.g., vectors based on human foamy virus (HFV) or other viruses in the Spumavirus genera.

Foamy viruses (FVes) are the largest retroviruses known today and are widespread among different mammals, including all non-human primate species, however are absent in humans. This complete apathogenicity qualifies FV vectors as ideal gene transfer vehicles for genetic therapies in humans and clearly distinguishes FV vectors as gene delivery system from HIV-derived and also gammaretrovirus-derived vectors.

FV vectors are suitable for gene therapy applications because they can (1) accommodate large transgenes (>9 kb), (2) transduce slowly dividing cells efficiently, and (3) integrate as a provirus into the genome of target cells, thus enabling stable long term expression of the transgene(s). FV vectors do need cell division for the pre-integration complex to enter the nucleus, however the complex is stable for at least 30 days and still infective. The intracellular half-life of the FV pre-integration complex is comparable to the one of lentiviruses and significantly higher than for gammaretroviruses, therefore EV are also—similar to LV vectors—able to transduce rarely dividing cells. FV vectors are natural self-inactivating vectors and characterized by the fact that they seem to have hardly any potential to activate neighboring genes. In addition, FV vectors can enter any cells known (although the receptor is not identified yet) and infectious vector particles can be concentrated 100-fold without loss of infectivity due to a stable envelope protein.

FV vectors achieve high transduction efficiency in pluripotent hematopoietic stem cells and have been used in animal models to correct monogenetic diseases such as leukocyte adhesion deficiency (LAD) in dogs and Fanconi anemia in mice. FV vectors are also used in preclinical studies of β-thalassemia.

Additional examples of viral vectors include those derived from adenoviruses (e.g., adenovirus 5 (Ad5), adenovirus 35 (Ad35), adenovirus 11 (Ad11). adenovirus 26 (Ad26), adenovirus 48 (Ad48) or adenovirus 50 (Ad50)), adeno-associated virus (AAV; see, e.g., U.S. Pat. No. 5,604,090; Kay et al., *Nat. Genet.* 24:257 (2000); Nakai et al., *Blood* 91:4600 (1998)), alphaviruses, cytomegaloviruses (CMV), flaviviruses, herpes viruses (e.g., herpes simplex), influenza viruses, papilloma viruses (e.g., human and bovine papilloma virus; see, e.g., U.S. Pat. No. 5,719,054), poxviruses, vaccinia viruses, etc. See Kozarsky and Wilson, 1993, *Current Opinion in Genetics and Development* 3:499-503, Rosenfeld, et al., 1991, *Science* 252:431-434; Rosenfeld, et al., 1992, *Cell* 68:143-155, Mastrangeli, et al., 1993, *J. Clin. Invest.* 91:225-234; Walsh, et al., 1993, *Proc. Soc. Exp. Biol. Med.* 204:289-300; and Lundstrom, 1999, *J. Recept. Signal Transduce. Res.* 19: 673-686. Examples include modified vaccinia Ankara (MVA) and NYVAC, or strains derived therefrom. Other examples include avipox vectors, such as a fowlpox vectors (e.g., FP9) or canarypox vectors (e.g., ALVAC and strains derived therefrom).

Other methods of gene delivery include use of artificial chromosome vectors such as mammalian artificial chromosomes (Vos, 1998, *Curr. Op. Genet. Dev.* 8:351-359) and yeast artificial chromosomes (YAC). YAC are typically used when the inserted nucleic acids are too large for more conventional vectors (e.g., greater than 12 kb).

Vectors and other methods to deliver nucleic acids can include regulatory sequences to control the expression of the nucleic acid molecules. These regulatory sequences can be eukaryotic or prokaryotic in nature. In particular embodiments, the regulatory sequence can be a tissue specific promoter such that the expression of the one or more therapeutic proteins will be substantially greater in the target tissue type compared to other types of tissue. In particular embodiments, the regulatory sequence can result in the constitutive expression of the one or more therapeutic proteins upon entry of the vector into the cell. Alternatively, the regulatory sequences can include inducible sequences. Inducible regulatory sequences are well known to those skilled in the art and are those sequences that require the presence of an additional inducing factor to result in expression of the one or more therapeutic proteins. Examples of suitable regulatory sequences include binding sites corresponding to tissue-specific transcription factors based on endogenous nuclear proteins, sequences that direct expression in a specific cell type, the lac operator, the tetracycline operator and the steroid hormone operator. Any inducible regulatory sequence known to those of skill in the art may be used.

In particular embodiments, the nucleic acid is stably integrated into the genome of a cell. In particular embodiments, the nucleic acid is stably maintained in a cell as a separate, episomal segment.

In particular embodiments, the efficiency of integration, the size of the DNA sequence that can be integrated, and the number of copies of a DNA sequence that can be integrated into a genome can be improved by using transposons. Transposons or transposable elements include a short nucleic acid sequence with terminal repeat sequences upstream and downstream. Active transposons can encode enzymes that facilitate the excision and insertion of nucleic acid into a target DNA sequence.

A number of transposable elements have been described in the art that facilitate insertion of nucleic acids into the genome of vertebrates, including humans. Examples include sleeping beauty (e.g., derived from the genome of salmonid fish); piggyback (e.g., derived from lepidopteran cells and/or the *Myotis lucifugus*); mariner (e.g., derived from *Drosophila*); frog prince (e.g., derived from *Rana pipiens*); Tol2 (e.g., derived from medaka fish); TcBuster (e.g., derived from the red flour beetle *Triboliurn castaneum*) and spinON. CRISPR-Cas systems may also be used. Exemplary description of computer-executable instructions that may be performed by a device as described herein are denoted herein as SW6 and are described in the following table 4.

of a second volume of nucleic acid carrier, a second volume of buffer, an additional media component not previously added, or a second volume of media, e.g. transduction media. In particular embodiments, the sequential addition may be performed within the treatment chamber. For example, a user may specify a volume corresponding to each additional liquid component to be added to the cell suspension and, based on the user input, tubing paths may be cleared, e.g. to prevent contamination, and/or the specified volume of each component may be added to the treatment chamber. In particular embodiments, the sequential addition may be performed outside the treatment chamber, e.g. within a combination cell separator and genetic modification introducer (CCS-GMI) or the cell separator and/or an electropo-

TABLE 4

Exemplary description of computer-executable nucleic acid introduction instructions.

SW 6. Description 1. This program is suitable for initiating viral vector transduction or media exchange and liquid component addition to any cell product.
SW 6. Description 2. This program is suitable for initiating viral vector transduction or media exchange and liquid component addition to any cell product. Once media exchange is completed, virus vector or additional liquid component is added to the cell suspension in the chamber.
SW 6. Description 3. This program is suitable for initiating viral vector transduction or media exchange and liquid component addition to any cell product. The program initiates with the assumption that the cell fraction to be transduced/media exchanged is in a Target Cell Bag included in the pre-fabricated tubing set. First the cell suspension is transferred from the Target Cell Bag to the device chamber. Media exchange is then performed dilution of the cell suspension with media for media exchange, then step-wise centrifugation to pellet cells in suspension, and finally removal of supernatant volume. Once media exchange is completed, virus vector or additional liquid component is added to the cell suspension.
SW 6. Description 4. This program is suitable for initiating viral vector transduction or media exchange and liquid component addition to any cell product. The program initiates with the assumption that the cell fraction to be transduced/media exchanged is in a Target Cell Bag included in the pre-fabricated tubing set. First the cell suspension is transferred from the Target Cell Bag to the device chamber. Media exchange is then performed by three cycles of the following: dilution of the cell suspension to the maximum chamber volume with media specified for media exchange, then step-wise centrifugation to pellet cells in suspension, and finally removal of maximum supernatant volume. During the final supernatant removal, the final cell suspension volume is obtained. Once media exchange is completed, virus vector or additional liquid component is added to the cell suspension in the chamber.
SW6 Description 5. This program is suitable for initiating viral vector transduction or media exchange and liquid component addition to any cell product. The program initiates with the assumption that the cell fraction to be transduced/media exchanged is in the Target Cell Bag included in the pre-fabricated tubing set. The user specifies the volume of the final desired cell suspension and the volume of virus vector or other liquid component to be added to the cell suspension. First the cell suspension is transferred from the Target Cell Bag to the device chamber and the Target Cell Bag is rinsed with media specified for media exchange. Bag rinse is also transferred to the chamber. Media exchange is then performed by three cycles of the following: dilution of the cell suspension to the maximum chamber volume with media specified for media exchange, then step-wise centrifugation to pellet cells in suspension, and finally removal of maximum supernatant volume. During the final supernatant removal, the user-defined final cell suspension volume is obtained. Once media exchange is completed, virus vector or additional liquid component is added to the cell suspension in the chamber.

Example 8

Liquid Addition Method and Computer-Executable Instructions Therefor

In an embodiment, a method further includes a sequential addition of one or more additional liquid components to the target cell suspension. In particular embodiments, the one or more additional liquid components may include at least one rator. For example, following the introduction of the nucleic acid carrier to the target cells in the CCS-GMI 800 at block 512, the target cells may be maintained within the CCS-GMI 800 while a sequential addition of a liquid component is added. Exemplary description of computer-executable instructions that may be performed by a device as described herein are denoted herein as SW7 and are described in the following table 5.

TABLE 5

Exemplary description of computer-executable liquid addition instructions.

SW7 Description 1. This program is suitable for addition of any two liquid components to a cell suspension.
SW7 Description 2. This program is suitable for addition of any two liquid components to a cell suspension. The program may initiate with the assumption that the cell suspension for

TABLE 5-continued

Exemplary description of computer-executable liquid addition instructions.

component addition is in the device chamber. The device then adds a volume of each component to the device chamber.
SW7 Description 3. This program is suitable for addition of any two liquid components to a cell suspension. The program may initiate with the assumption that the cell suspension for component addition is in the device chamber. The device then sequentially adds a specified volume of each component to the device chamber.
SW7 Description 4. This program is suitable for sequential addition of any two liquid components to a cell suspension. The program may initiate with the assumption that the cell suspension for component addition is in the device chamber. The user specifies the desired volume of each liquid component to add to the cell suspension. The device then sequentially adds the specified volume of each component to the device chamber.
SW7 Description 5. This program is suitable for sequential addition of any two liquid components to a cell suspension. One example of a two-component addition would be the addition of a second volume of virus vector and additional transduction media during a two-hit cell transduction method. The program may initiate with the assumption that the cell suspension for component addition is in the device chamber. The user specifies the desired volume of each liquid component to add to the cell suspension. The device first clears the tubing path from the components to the chamber to prevent unwanted contamination. The device then sequentially adds the specified volume of each component to the device chamber and gently mixes the contents.

Example 9

Cell Culture Method and Computer-Executable Instructions Therefor

At various stages during the described methods, it may be helpful or necessary to culture the targeted cells. For example, as the nucleic acid introduction process may be stressful, resulting gene-modified target cells may undergo cell culture procedures to allow them to re-gain health and/or begin proliferation before purification and formulations. Moreover, in particular embodiments, the target cells may undergo culturing prior to the nucleic acid introduction process, e.g. to bolster their health before the process. Accordingly, the methods herein may also include culturing of the target cell product.

In particular embodiments, culturing the cell product may include determining one or more gas parameters corresponding to at least one gas to expose to the cell product. For example, the system may include one or more gas cylinders connected to the treatment chamber and for which individual partial pressures may be independently regulated via one or more gas regulators (e.g. illustrated in FIG. 15A). Accordingly, in particular embodiments, the gas regulator(s) may selectively control a first partial pressure of a first gas up through an N-th partial pressure of an N-th gas. In particular embodiments, a partial pressure corresponding to each of nitrogen gas ($N_2$), carbon dioxide gas ($CO_2$), and oxygen gas ($O_2$) may be regulated during the culturing of the cell product. Moreover, in particular embodiments, culturing the cell product may include determining an optimal treatment chamber temperature at block 704. One of skill in the art will realize that both the optimal gas parameters and the optimal temperature for culturing will vary depending on the type of cell product and stage of the process. In particular embodiments, the treatment chamber may be maintained at the optimal temperature at block 706. Any suitable technique for maintaining the treatment temperature, whether now known or subsequently developed, may be used.

At block 708, one or more gases may be mixed according to the determining gas parameters at block 702. In particular embodiments, the gases may be mixed within the treatment chamber, e.g. each gas is individually introduced into the treatment chamber. In particular embodiments, the gases may be mixed external to the treatment chamber. It may be preferable to mix the gases external to the treatment chamber in a separate mixing device in order to more accurately obtain respective partial pressures for each gas. At block 710, the gas mixture may be periodically exchanged during the culturing of the cell product. For example, in particular embodiments the gas mixture is completely exchanged at regular intervals, e.g. 15 minutes, for one or more of a predetermined time period or until a user terminates the cell culturing. Exemplary description of computer-executable instructions that may be performed by a device as described herein are denoted herein as SW8 and are described in the following table 6.

TABLE 6

Exemplary description of computer-executable cell culture instructions.

SW8 Description 1. This program is suitable for culture of any cell product.
SW8 Description 2. This program is suitable for culture of any cell product in the device chamber. The program initiates with the assumption that the cells to be cultured are already formulated for culture and are present in the device chamber. The program can define the gas parameters of N2, CO2 and O2, as well as the chamber temperature or can define subsets of these parameters based on user input. The device maintains the chamber to the desired temperature and creates the appropriate gas formulation for the chamber.
SW8 Description 3. This program is suitable for culture of any cell product in the device chamber. The program initiates with the assumption that the cells to be cultured are already formulated for culture and are present in the device chamber. The program allows the user to define the gas parameters of N2, CO2 and O2, as well as the chamber temperature. The program also gives the user the option to have the cell suspension gently mixed during the incubation period. The device heats the chamber to the desired temperature and mixes the TABLE 6-continued Exemplary description of computer-executable cell culture instructions.

appropriate gas formulation for the chamber. The cultured cell suspension remains in the device chamber upon program termination.
SW8 Description 4. This program is suitable for culture of any cell product in the device chamber. The program can define or allows the user to define the gas parameters of N2, CO2 and O2, as well as the chamber temperature. The program also gives the user the option to have the cell suspension gently mixed during the incubation period. The device heats the chamber to the desired temperature and mixes the appropriate gas formulation for the chamber. The cultured cell suspension remains in the device chamber upon program termination.
SW8 Description 5. This program is suitable for culture of any cell product in the device chamber. The program initiates with the assumption that the cells to be cultured are already formulated for culture and are present in the device chamber. The program allows the user to define the gas parameters of N2, CO2 and O2, as well as the chamber temperature. The program also gives the user the option to have the cell suspension gently mixed once every 30 minutes during the incubation period. The device heats the chamber to the desired temperature and mixes the appropriate gas formulation for injection into the chamber. Once the appropriate gas formulation is achieved., the gas mix is injected into the chamber. The device continues the incubation at temperature with a complete gas exchange of the chamber every 15 minutes and mixing as specified until the user terminates the program. The cultured cell suspension remains in the device chamber upon program termination.

Example 10

Purification (e.g., Harvest) and Formulation Method and Computer-Exectuable Instructions Therefor FIG. 15A shows a schematic diagram of an exemplary system for culturing, purifying, and formulating gene-modified cells for application-specific use, e.g. administering the gene-modified cells to a subject. FIG. 15B is a flow chart of an exemplary method for culturing, purifying, and formulating the gene-modified cells using the exemplary system of FIG. 15A.

In particular embodiments, the purification and final formulation of the cell product may include removing unwanted media components from the final formulation. For example, cells and genetically-modified target cells can be purified and formulated for administration to a subject within the device. A formulation refers to a cell or modified cell prepared with a pharmaceutically acceptable carrier for administration to a subject. Exemplary carriers and modes of administration of cells are described at pages 14-15 of U.S. Patent Publication No. 2010/0183564. Additional pharmaceutical carriers are described in *Remington: The Science and Practice of Pharmacy*, 21st Edition, David B. Troy, ed., Lippicott Williams & Wilkins (2005).

In particular embodiments, purification and final formulation includes pelleting the cell product and removing the resulting supernatant. Removal of the resulting supernatant may be beneficial as it may remove any remaining nucleic acid carrier and/or nucleic acid carrier, e.g. viral vectors which could inadvertently be administered to a patient. It should be appreciated that an appropriate media for culturing purposes may be different than an appropriate media for administration purposes. Accordingly, in particular embodiments, genetically-modified cells can be purified from a culture medium, and washed and concentrated into a carrier in a therapeutically-effective amount at block 714. Exemplary carriers include saline, buffered saline, physiological saline, water, Hanks' solution, Ringer's solution, Nonnosol-R (Abbott Labs), Plasma-Lyte A® (Baxter Laboratories, Inc., Morton Grove, Ill.), glycerol, ethanol, and combinations thereof.

In particular embodiments, carriers can be supplemented with human serum albumin (HSA) or other human serum components or fetal bovine serum. In particular embodiments, a carrier for infusion includes buffered saline with 5% HSA or dextrose. Additional isotonic agents include polyhydric sugar alcohols including trihydric or higher sugar alcohols, such as glycerin, erythritol, arabitol, xylitol, sorbitol, or mannitol.

Carriers can include buffering agents, such as citrate buffers, succinate buffers, tartrate buffers, fumarate buffers, gluconate buffers, oxalate buffers, lactate buffers, acetate buffers, phosphate buffers, histidine buffers, and/or trimethylamine salts.

Stabilizers refer to a broad category of excipients which can range in function from a bulking agent to an additive which helps to prevent cell adherence to container walls. Typical stabilizers can include polyhydric sugar alcohols; amino acids, such as arginine, lysine, glycine, glutamine, asparagine, histidine, alanine, ornithine, 2-phenylalanine, glutamic acid, and threonine; organic sugars or sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as HSA, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran.

Where necessary or beneficial, formulations can include a local anesthetic such as lidocaine to ease pain at a site of injection.

Therapeutically effective amounts of cells within formulations can be greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$ cells.

In formulations disclosed herein, cells are generally in a volume of a liter or less, 500 mls or less, 250 mls or less or 100 mls or less. Hence the density of administered cells is typically greater than $10^4$ cells/ml, $10^7$ cells/ml or $10^8$ cells/ml.

The formulations disclosed herein can be prepared for administration by, for example, injection, infusion, perfusion, or lavage.

At block 716, the formulated gene modified product may be removed from the treatment chamber for application specific use. For example, the gene modified product may be transferred to a vial from which a syringe may be loaded for subject administration. The compositions and formulations disclosed herein can be prepared for administration by, for example, injection, infusion, perfusion, or lavage. Exemplary description of computer-executable instructions that may be performed by a device as described herein are denoted herein as SW9 and are described in the following table 7:

TABLE 7

Exemplary description of computer-executable purification
(e.g., harvest) and formulation instructions SW9 Description 1. This program is suitable for harvest and/or final formulation of any cell product in the chamber of the device.
SW9 Description 2. This program is suitable for harvest and final formulation of any cell product in the chamber of the device. The program initiates with the assumption that the cell suspension to be harvested and formulated is in the device chamber. The program removes unwanted media components from the final formulation. First, the cell suspension in the chamber is centrifuged in a step-wise manner to pellet cells. Once pelleted, supernatant is removed. After initial supernatant removal, washes with media exchange are accomplished. Following the final wash/media exchange, additional supernatant is removed. The formulated cell product is transferred from the device chamber for removal.
SW9 Description 3. This program is suitable for harvest and final formulation of any cell product in the chamber of the device. The program initiates with the assumption that the cell suspension to be harvested and formulated is in the device chamber. The volume of the initial cell suspension supernatant for transfer to sufficiently remove unwanted media components from the final formulation is identified. First, the cell suspension in the chamber is centrifuged in a step-wise manner to pellet cells. Once pelleted, the identified supernatant volume is removed. After initial supernatant removal, washes with media exchange are accomplished as follows: first, the pelleted cell suspension is diluted with final formulation media, then cell suspension is centrifuged in a step-wise manner to pellet cells. Once pelleted, a supernatant volume is removed. Following the final wash/media exchange, additional supernatant is removed to bring the final cell product formulation to a total volume. The formulated cell product is transferred from the device chamber to the Target Cell Bag attached to the device for removal and application-specific use.
SW9 Description 4. This program is suitable for harvest and final formulation of any cell product in the chamber of the device. The program initiates with the assumption that the cell suspension to be harvested and formulated is in the device chamber. The user specifies the volume of the initial cell suspension supernatant for transfer to sufficiently remove unwanted media components from the final formulation. First, the cell suspension in the chamber is centrifuged to pellet cells. Once pelleted, the specified supernatant volume is removed. After initial supernatant removal, washes with simultaneous media exchange are accomplished as follows: first, the pelleted cell suspension is diluted to a volume with final formulation media, then cell suspension is centrifuged in a step-wise manner to pellet cells. Once pelleted, a preset supernatant volume is removed. Following the final wash/media exchange, additional supernatant is removed to bring the final cell product formulation to a total volume. The formulated cell product is transferred from the device chamber to the Target Cell Bag attached to the device for removal and application-specific use.
SW9 Description 5. This program is suitable for harvest and final formulation of any cell product in the chamber of the device. The program initiates with the assumption that the cell suspension to be harvested and formulated is in the device chamber. The user specifies the volume of the initial cell suspension supernatant for transfer to sufficiently remove unwanted media components from the final formulation. First, the cell suspension in the chamber is centrifuged in a stepwise manner to pellet cells. Once pelleted, the specified supernatant volume is removed. After initial supernatant removal, three washes with simultaneous media exchange are accomplished as follows: first, the pelleted cell suspension is diluted to the maximum chamber volume with final formulation media, then cell suspension is centrifuged in a step-wise manner to pellet cells. Once pelleted, a preset supernatant volume is removed. Following the final wash/media exchange, additional supernatant is removed to bring the final cell product formulation to a total volume of 45 mL. The formulated cell product is transferred from the device chamber to the Target Cell Bag attached to the device for removal and application-specific use.

Referring back now to FIG. 11A, it should be appreciated that any of the exemplary systems and/or devices disclosed herein may be in communication with a platform controller 264 which may control any of the operations of methods 200, 300, 400, 500, 600, and/or 700, or any subset thereof. The platform controller 264 may include one or more processors) 266 and/or one or more computer readable media 268. The computer readable media 268 may include volatile storage (e.g., random-access memory) and/or non-volatile memory (e.g., a hard disk or another type of non-volatile memory). The computer readable media 268 may be used to store software instructions 270, such as device drivers, an operating system, and/or software applications that are executable by the processors 266 to perform various functions.

In particular embodiments, the computer readable media 268 may include a valve controller 272 to selectively toggle one or more valves (denoted by valve symbol x) for opening and/or closing one or more fluid paths. In particular embodiments, the computer readable media 268 may include a pump controller 274 to selectively operate one or more pumps (denoted by pump symbol ⊖ ) fix forcibly perusing a sample or portion thereof through one or more fluid paths. Although the valve symbols and pump symbols are shown on but a few of the many flow paths illustrated in the figures, it should be appreciated that it is within the scope of the present disclosure that a valve and/or pump be included on any one of the flow paths and/or sections of tubing used to create the flow paths. More detail regarding appropriate types of valves and pumps used in particular embodiments may be found in U.S. Patents: U.S. Pat. Nos. 5,691,208; 6,468,432; and 8,727,132.

In particular embodiments, the computer readable media 268 may include a treatment chamber controller 276 to control one or more functionalities of the treatment chamber. For example, in particular embodiments wherein the treatment chamber is configured to perform centrifugation, the treatment chamber controller 276 may be configured to control one or more of centrifugation speed (e.g. RPMs), an agitation schedule (e.g. duration and intensity of agitation), and/or one or more internal valves for removing supernatant. In particular embodiments, the treatment chamber controller 276 may be configured to control one or more heating and/or cooling elements used to maintain one or more incubation environments within the treatment chamber.

In particular embodiments, the computer readable media 268 may include a target cell selector and/or combination cell selector and nucleic acid introducer (TCS/CCS-NAI) controller 278. The TCS/CCS-NAI controller 278 may be configured to control performance of one more functionalities disclosed herein with relation to the target cell selector of FIG. 13A (e.g. a MACS or FACS based cell selector) and/or the CCS-NAI 800 and/or the cell separator and/or electroporator 1100. For example, the ICS/CCS-NAI controller 278 may be configured to control the CCS-NAI 800 during sequential performance of a MACS protocol followed by an electroporation protocol of selected cells maintained within the CCS-NAI 800.

Methods disclosed herein include producing cells for and/or treating subjects (humans, veterinary animals (dogs, cats, reptiles, birds, etc.), livestock (horses, cattle, goats, pigs, chickens, etc.), and research animals (monkeys, rats, mice, fish, etc.) with genetically-modified cells disclosed herein. Treating subjects includes delivering therapeutically effective amounts. Therapeutically effective amounts include those that provide effective amounts, prophylactic treatments, and/or therapeutic treatments.

An "effective amount" is the number of cells necessary to result in a desired physiological change in a subject. Effective amounts are often administered for research purposes.

A "prophylactic treatment" includes a treatment administered to a subject who does not display signs or symptoms of a condition to be treated or displays only early signs or symptoms of the condition to be treated such that treatment is administered for the purpose of diminishing, preventing, or decreasing the risk of developing the condition. Thus, a prophylactic treatment functions as a preventative treatment against a condition.

A "therapeutic treatment" includes a treatment administered to a subject who displays symptoms or signs of a condition and is administered to the subject for the purpose of reducing the severity or progression of the condition. The actual dose amount administered to a particular subject can be determined by a physician, veterinarian, or researcher taking into account parameters such as physical and physiological factors including target; body weight; type of condition; severity of condition; upcoming relevant events, when known; previous or concurrent therapeutic interventions; idiopathy of the subject; and route of administration, for example. In addition, in vitro and in vivo assays can optionally be employed to help identify optimal dosage ranges.

Exemplary Embodiments of the Disclosed Processing Modules and/or Software

As explained above, the system described herein includes a computer control system or unit 112 providing monitoring and/or control of one or more aspects of the system. The computer control system 112 can include one or more modules or systems to process information (e.g., flow information, etc.) within the system 100 and can include a wide variety of proprietary and/or commercially available computers, components or electronics having one or more processing structures and the like, with such systems often comprising data processing hardware and/or software configured to implement any one or a combination of method steps as described herein.

The following table, Table 8 lists various embodiments of control software that may be used by the device. Such software may be, for example, stored in a memory of the device as computer-executable instructions. Table 8 has three columns. The first column identifies a given software process, the second column identifies the function performed by the device in accordance with that software process, and the third column identifies the operations executed by the device to perform the corresponding function. The below table refers to a device. According to various embodiments, such a device may be, for example a device from the CliniMACS Prodigy line of products from Miltenyi Biotec, Inc. executing software such as the associated CliniMACS Process Software, including those products as equipped with additional modifications, as needed. In an embodiment, such a device may be as described in the following U.S. patent applications and publications: U.S. Pat. No. 8,727,132 ("Sample Processing System and Methods"); U.S. Pat. No. 8,747,290 ("Centrifuge for Separating a Sample into At Least Two Components"; U.S. Patent Publ. No. 2015/0017714 ("Centrifugation Chamber with Gas Permeable Membrane Layers for Cell Cultivation"); and U.S. Patent Publ. No. 2016/0264919 ("Centrifugation Chamber with Gas Permeable Membrane Layers for Cell Cultivation"), each of which is incorporated by reference herein in its entirety.

Such a device may include, among other components, a sample processing unit, a sample separation unit, a processor, and a memory. The sample processing unit may include an input port, an output port, and a centrifuge chamber. In an embodiment, the centrifuge chamber comprises a circular bottom, a circular top, and a wall passing therebetween, thus forming an internal compartment that is configured to contain and process a biological sample comprising cells. The sample processing unit may be configured to rotate the centrifuge chamber about an axis that passes through the circular bottom and the circular top so as to apply a centrifugal force to a sample deposited in the chamber and thereby to separate at least a first component and a second component of the deposited sample. The input port and the output port may be configured and positioned to deliver a sample to and from the internal compartment while the centrifuge chamber is rotating. In an embodiment, the centrifuge chamber comprises a detection window that extends radially in the bottom or top of the chamber from a position adjacent to the rotation axis to a position near the perimeter of the chamber. The sample processing unit may further comprise a detector that is constructed and aligned to receive light passing through a sample in the detection window of the centrifuge chamber so as to assess a characteristic of the deposited sample radially through and along the detection window, thereby monitoring separation of the first component from the second component in the chamber.

The sample separation unit may be coupled to the output port of the sample processing unit. In an embodiment, the sample separation unit comprises a separation column holder, a pump, a plurality of valves configured to at least partially control fluid flow through a fluid circuitry, and a separation column positioned in the holder, wherein the separation column is configured to separate labeled and unlabeled components of a sample flowed through the column.

In an embodiment, the processor is coupled to each of the sample processing unit and the sample separation unit, and controls the operation of the sample processing unit and the sample separation unit. The memory may be coupled to the processor and have instructions stored thereon that, when executed by the processor, cause the device to perform operations as described below in Table 8.

Each control software module described in Table 8, when executed by a processor of the device, causes the device to perform the described functions. Further, while the table below describes various distinct embodiments, it is contemplated that the various embodiments can be used alone or in any number of variations, combinations, and/or permutations.

TABLE 8

Exemplary embodiments of the disclosed processing modules and/or control software

| Program Abbreviated Name | Program Goal | Detailed Program Description |
|---|---|---|
| CD8CD4 Sequential | >95% purity for CD4 and CD8 populations delivered to 2 separate bags. | Sequential isolation of CD8 cells and CD4 cells from a single non-mobilized apheresis product. CD8 selected first, using depletion-based column loading speed to ensure efficient depletion from the nontarget fraction. After CD8 enrichment the nontarget fraction is returned to chamber for CD4 labeling. Uses titrated reagent volumes and labeling in <70 ml volume with both labeling volumes based on target cell number. |
| BM and mLP Selection TS510 | Purity and recovery of both bone marrow and mobilized apheresis product starting materials | Operator defines the starting material type. For BM, the product is loaded to chamber in stages, a buffy coat spin performed on each stage and RBC pellet adjusted as needed to fit product in 45 ml volume. After all product is loaded and adjusted to 70 ml cell suspension, ficoll separation is performed. MNCs harvested and returned to cleaned chamber, washed, labeled, post-label washed and CD34 selected. For mLP, product is loaded, platelet washed and process for CD34 selection without ficoll. |
| CD4 Depletion TS310 | CD4 depletion from dual-mobilized apheresis material achieving <3% CD4+ cells in depleted product | Very large cell number (1.2e11) and age of product (24-48 h) and high granulocyte content called for special measures to ensure success. Program is flexible for labeling with 1-4 vials of CD4 reagent depending on CD4 cell numbers (0-48 billion CD4+ cells). Product is loaded in stages, pellet size determined and if >110 ml RBCs are removed via V18 to fit product to chamber. After platelet wash product is adjusted to labeling volume specific to vial number being used. Prior to labeling, DNAse + MgCl2 solution is added to chamber and incubated to digest free DNA released by |

TABLE 8-continued

Exemplary embodiments of the disclosed processing modules and/or control software

| Program Abbreviated Name | Program Goal | Detailed Program Description |
|---|---|---|
| | | granulocytes. IVIg is then dispensed to block nonspecific binding, and finally CD4 reagent is dispensed and incubated. Unbound reagent is washed out and product is filtered and then applied to the column using depletion conditions. |
| CBU CD34 selection | Selection of CD34+ cells from thawed cord blood units | Following thaw, CBU is attached to the application bag and washed with dextran/HSA per the Rubenstein method. After dextran wash, cells are washed into the device buffer supplemented with DNAse, sodium citrate, and MgCl2. Cells are then labeled and selected following the device's standard CD34 selection sequence. |
| Fresh CBU CD34 selection | Selection of CD34+ cells from fresh cord blood units | Product is loaded to chamber and centrifuged at 300 g to pellet cells. Pellet size is measured using layer detection and RBCs removed to adjust pellet size to 45 ml if needed. After pellet adjustment, product is diluted and ficolled. MNCs harvested and returned to cleaned chamber, washed and CD34 selection process performed. |
| Culture Modules | Modular concept program for performing media exchanges, additions, volume adjustments, reagent additions, and formulation | Operator chooses from a menu of option which activity is to be performed. Activities options include: load cells to chamber, sample, add volume, remove volume, add reagent, culture, harvest, etc. Selection of a module takes the operator to that specific module to complete the activity. Once the activity is completed, the program returns to the Options menu for selection of the next activity. |
| Pan T Isolation programs | Negative selection of T cells using Pan T isolation kit (negative selection kit). | Adaptation of a small-scale isolation kit protocol to the overall device. The key to this is to adjust the cell suspension volume to very low volumes for labeling. Labeling volumes can be as low as 3 ml. Labeling volumes and stage numbers for column applications are determined by cell numbers input by operator. |
| Research Modules Programs | Modular concept offering flexibility in processing leukopaks for research cell isolations | Similar to culture modules, the program offers an Options menu for flexibility. Options include ficoll, platelet wash, sample, and cell isolation using Pan T, CD4, CD8 or NK isolation kits. |

TABLE 8-continued

Exemplary embodiments of the disclosed processing modules and/or control software

| Program Abbreviated Name | Program Goal | Detailed Program Description |
| --- | --- | --- |
| TCRab depiction | Depletion of TCRab+ cells from cultured T cells that have been treated with a TCRab knockout talen. | Made for large numbers of cultured T cells. Uses reduced washing compared to the TCRab process with a goal to perform the depletion in less than 8 hours. |
| Protein incubation and TCRab depletion | incubate mLP product with protein, and then deplete TCRab+ cells | Program performs special low-volume adjustment to reduce cell suspension volume to target volume for protein incubation. Protein is dispensed and product is incubated 1 hr at controlled temperature. After incubation washes are performed and TCRab labeling and depletion are performed |
| WB Protein Incubation | Incubate a whole blood product with protein | Whole blood is mixed with hetastarch and RBC reduced using hetastarch sedimentation process. After RBC reduction, product is returned to chamber, washed and adjusted to target volume for protein treatment. Incubated with protein 1 hr at controlled temperature and then washed and eluted. Provides option to elute only part of the product and volume-adjust to formulate the cell dose to the operator's desired concentration. |
| CD4CD8 1 ml beads TS510 | Co-enrichment of CD4/CD8 cells from a leukopak using only 1 ml of each reagent | Built for a process for enriching CD4/CD8s using 1 ml of each reagent. Labeling volume are adjusted to optimize labeling based on cell numbers. |
| Ficoll + CD14 enrichment | Generate PBMCs and subject 80% of the PBMCs to CD14 selection | Apheresis product is ficolled, MNCs harvested and returned to cleaned chamber and washed. 20% of the washed cells are returned to intermediate bag for offline use. Remaining 80% of cells are labeled with CD14 reagent and selected using a staged column-loading sequence based on cell number. |
| CD19 66% titer | B cell enrichment optimized for maximal recovery | Program uses titrated reagent, at 66% strength. Also uses special elution sequence for enhanced recovery of target cells from the column. B cell enrichment is notoriously difficult in terms of recovery, and this program resulted in doubling the recovery that could be obtained previously using another device. |

TABLE 8-continued

Exemplary embodiments of the disclosed processing modules and/or control software

| Program Abbreviated Name | Program Goal | Detailed Program Description |
|---|---|---|
| CD14, CD19, CD56 depletion | T cell enrichment by negative selection with desired purity >90% | Apheresis material is first subjected to ficoll. MNCs are harvested and returned to cleaned chamber for washing and then labeling with CD14, CD19 and CD56 reagents. Labeled cells are then depleted using bulk and sensitive depletion modes. |
| CD3/CD19 depletion | NK enrichment by depletion of T cells and B cells from apheresis material | Apheresis material is labeled with CD3 and CD19 reagent and labeled cells are depleted using bulk and sensitive depletion modes |
| CD3CD56 sequential | Selection of CD3+ and CD56+ cells, isolated in separate bags | Program has CD8CD4 sequential program as its core, with modifications made based on different reagent vial capacities |
| SCD CD 34 2 ml bead sw120 | Isolation of CD34+ cells from sickle cell disease transfusion discard material | Similar to BM CD34 program. Large volume of transfusion waste (2-3 L) if first buffy-coat reduced to 700 ml and loaded into device. Program further buffy coat reduces it using layer detection and RBC removal. Remaining product is ficolled, labeled and CD34 selected. |
| CD3 TS510 v1 | CD3 selection from apheresis material | Half-vial process, requires volume reduction to 45 ml for labeling. |
| CD4 CD8 TS510 v1 | CD4 CD8 dual enrichment from apheresis material | Labeling and reagent volumes are titrated based on target cell numbers. |
| CD19 TS510 v4 | Enrichment of engineered T cells artificially expressing CD19 | Uses special high-titer of CD19 reagent to capture high frequency CD19-expressing cells. |
| D 0 Wash v10 flexvol | Specific washing protocol | Gentle washing performed in stages, with washed cells subjected to minimal centrifugation time to reduce stress. |
| D7 BPX-501 Select v2 | CD19 selection after 7 days of culture | Uses special high-titer of CD19 reagent to capture high frequency CD19-expressing cells. |
| D7 pt 1 wash label v2 | Washing and labeling of cultured T cells | Uses special high-titer of CD19 reagent to capture high frequency CD19-expressing cells. Does not perform the column enrichment steps. |
| D7 pt2 post-sel v2 | Selection of cultured, engineered T cells expressing CD19 | Performs the column enrichment steps for cells labeled using part 1 program. |
| BM3 CD34 SELECT SEQUENCE TS510 | Column selection sequence for CD34+ labeled bone marrow HSCs | CD34 selection sequence modeled on a combination of CliniMACS CD34 Selection 1 and CD34 Selection 2 programs, with 3 column reapplications for high purity. |
| TREG TS510 p1 aug4 | Part 1 of 2-part Treg isolation process: CD4 enrichment by neg selection using research isolation kit | Labeling conditions are based on total cell number and are scaled up from the research isolation kit protocol. Unwanted cells are depleted using bulk and sensitive depletion conditions. |

TABLE 8-continued

Exemplary embodiments of the disclosed processing modules and/or control software

| Program Abbreviated Name | Program Goal | Detailed Program Description |
|---|---|---|
| TREG TS510 p1 jul30 | Part 1 of 2-part Treg isolation process: CD4 enrichment by neg selection using research isolation kit | Labeling conditions are based on total cell number and are scaled up from the research isolation kit protocol. Unwanted cells are depleted using bulk and sensitive depletion conditions. |
| TREG TS510 part 1 | Part 1 of 2-part Treg isolation process: CD4 enrichment by neg selection using research isolation kit | Labeling conditions are based on total cell number and are scaled up from the research isolation kit protocol. Unwanted cells are depleted using bulk and sensitive depletion conditions. |
| TREG TS510 part 2 | Part 2 of 2-part Treg isolation process: CD25 enrichment | Labeling conditions are based on starting cell count. Cells are returned to chamber, volume-adjusted to appropriate labeling volume per starting cell number. Appropriate volume of CD25 microbeads are added to chamber and incubated 15 m. Enrichment is then performed using multiple reapplications for high purity. |
| CD 34 SELEC TS510 v1 | CD34 selection on TS510, compatible with products up to 60 billion TNC, 600 million CD34+ | Includes platelet wash, volume reduction, blocking with IVIg, bead incubation with intermittent mixing, post-label washes and column sequence modeled after a combination of process CD34 1 and CD34 2 programs with 3 reapplications for high purity. |
| CD 34 SELEC TS510 v4 | CD34 selection on TS510, compatible with products up to 60 billion TNC, 600 million CD34 | Includes platelet wash, volume reduction, blocking with IVIg, bead incubation with intermittent mixing, post-label washes and column sequence modeled after a combination of process CD34 1 and CD34 2 programs with 3 reapplications for high purity. |
| BM CD 34 SELEC TS510 v5 | CD34 selection from >150 ml of bone marrow following ficoll | Product is loaded to chamber, pellet size measured and if >45 ml a calculated volume of RBCs is removed via port controlled by valve 18. After initial adjustment, product is diluted and ficolled. MNCs are harvested and returned to cleaned chamber, washed free of ficoll and then platelet washed, labeled using column sequence described for CD34 Selection programs. |
| CD4 CD8 TS510 | Co-enrichment of CD4/CD8 cells from nonmobilized apheresis, optimized for recovery | Program uses titrated CD4 and CD8 reagents based on starting cell number and T cell frequency. This improves recovery over full-vial processing and provides a more economical selection strategy. |

TABLE 8-continued

Exemplary embodiments of the disclosed processing modules and/or control software

| Program Abbreviated Name | Program Goal | Detailed Program Description |
|---|---|---|
| ficoll culture setup LP | TS730 installation and ficoll performed on nonmobilized apheresis | Cells are loaded to chamber and adjusted to 70 ml. Product is then diluted with a 2x volume of buffer and centrifugation initiated at 1800 rpm. Ficoll is underlayered thru valve 18, and centrifuge speed increased to 400 g. After 10 m wait, chamber is slowly decelerated. Excess ficoll removed to waste and PBMCs harvested to intermediate storage bag. Chamber is cleaned and PBMCs returned, platelet washed and eluted for counting and eventual return for culture. |
| ficoll culture setup WB | TS730 installation and ficoll of a whole blood unit up to 400 ml | Whole blood is loaded to chamber and adjusted to 70 ml, using layer detection and RBC removal calculated from measured pellet size and assigned ideal pellet maximum size. Product is then diluted with a 2x volume of buffer and centrifugation initiated at 1800 rpm. Ficoll is underlayered thru valve 18, and centrifuge speed increased to 400 g. After 10 m wait, chamber is slowly decelerated. Excess ficoll removed to waste and PBMCs harvested to intermediate storage bag. Chamber is cleaned and PBMCs returned, platelet washed and eluted for counting and eventual return for culture. |
| SPINOCULATION | Allows flexible time/speed control for centrifugation of cells during lentiviral transduction | Flexible program allowing operator to explore impact of centrifugation speed and time on lentiviral or retroviral transduction efficiency. |
| Concentrate v9 | Concentration of 1 L of cultured T cells and exchange into PBS/EDTA | Continuous centrifugation program using TS720 to volume-reduce 1 L of cultured T cells and wash them into labeling buffer. Program allows flexible entry of pump speed during continuous centrifugation phase to allow exploration of optimal loading speed for best recovery. |
| TCRa_b V7 | TCRa/b depletion from up to 60 billion cultured T cells | For depletion of TCRab cells from cultured T cells within a 6-hour timeframe. Adaptation of a manual protocol for efficient depletion within the limits of one work day. |
| CD34 SELEC TS310 | CD34 selection from day-old dual-mobilized apheresis following LOVO platelet reduction | Platelet-washed apheresis material is loaded to chamber, volume-adjusted and labeled with 2 vials of CD34 reagent. Product is then washed, filtered and applied to column using CD34 selection 2 conditions. |

TABLE 8-continued

Exemplary embodiments of the disclosed processing modules and/or control software

| Program Abbreviated Name | Program Goal | Detailed Program Description |
|---|---|---|
| CULTURE MODULES TS510 | Flexible, modular culture programming allowing for low-volume cultures under 50 ml | Flexible program enables all activities associated with 2-10 day culture of cells, including loading selected cells to chamber, washing into medium, adjusting volume to between 5 ml and 250 ml as needed. Also allows addition of reagents such as vectors or cytokines to the chamber as needed, as well as formulation washes and harvest. |
| 45RO, CD19, CD14, CD56v4 | Enrichment of naive Pan T cells using GMP-manufactured reagents | Program uses CD45RO from Miltenyi Biotec, Inc. along with other reagents to negatively select for naïve Pan T cells for downstream genetic modification. |
| SCD gene targeting program | Gene editing on CBU-derived CD34+ cells after 2 days culture using CRISPR gene editing and AAV | Very small cell numbers require for concentration from 32 ml culture to 5 ml or less for electroporation. After electroporation, cells with AAV will be returned to chamber for 1 h spin at ~80 rpm to pack cells in chamber corners with the AAV. After the 1 hr spin, cells are volumed up to 32 ml, cultured for 48 h with a 4 rpm chamber rotation |
| Culture modules with scheduler | Addition of capability to schedule events in the current culture modules program | Current culture modules program requires operator interaction with the device. This schedules future events such as washes or feeding so that they can occur at a set time. This eliminates the need for operator to come into the lab on a weekend or gown into a cleanroom. |
| CD38−CD34+ HSCs from BM or mLP | CD38 depletion followed by CD34 selection from either bone marrow or mLP. | For bone marrow, ficoll or HES RBC reduction will be used first. Then CD38 labeling and depletion, chamber and TS cleaning and then CD34 labeling and selection |
| CD38−CD133+ HSCs from BM or mLP | CD38 depletion followed by CD133 selection from either bone marrow or mLP. | For bone marrow, ficoll or HES RBC reduction will be used first. Then CD38 labeling and depletion, chamber and TS cleaning and then CD133 labeling and selection |
| CD45RA−CD34+ HSCs from BM or mLP | CD45RA depletion followed by CD34 selection from either bone marrow or mLP. | For bone marrow, ficoll or HES RBC reduction will be used first. Then CD45RA labeling and depletion, chamber and TS cleaning and then CD34 labeling and selection |
| CD45R−CD133+ HSCs from BM or mLP | CD45RA depletion followed by CD133 selection from either bone marrow or mLP. | For bone marrow, ficoll or HES RBC reduction will be used first. Then CD45RA labeling and depletion, chamber and TS cleaning and then CD133 labeling and selection |

TABLE 8-continued

Exemplary embodiments of the disclosed processing modules and/or control software

| Program Abbreviated Name | Program Goal | Detailed Program Description |
|---|---|---|
| CD34 from plerixafor-mobilized SCD donor mLP | CD34 selection from sickle cell donors mobilized with plerixafor may require special handling due to unknown nature of the starting material | Ficoll if SCD donor material has high HCT or high grans. |
| CD16-depletion of high-gran leukopaks Per Tim's new product request | A large-bead format CD16 reagent to bind and retain granulocytes in the application bag using size exclusion and/or magnetic separation | Recent changes in apheresis collection platforms has resulted in difficult-to-manage mobilized products. High gran content leads to excessive release of DNA which clogs our columns. Approach is to add a gran-depletion method to the up-front handling of any high-gran product. A large magnetic particle that could be simply added to a LP, incubated and left behind in the bag. |

For example, an embodiment includes a system for separating cells, comprising: a) a sample processing unit, comprising an input port, an output port, and a centrifuge chamber, wherein the centrifuge chamber comprises a circular bottom, a circular top, and a wall passing therebetween, thus forming an internal compartment that is configured to contain and process a biological sample comprising cells; wherein the sample processing unit is configured to rotate the centrifuge chamber about an axis that passes through the circular bottom and the circular top so as to apply a centrifugal force to a sample deposited in the chamber and thereby to separate at least a first component and a second component of the deposited sample; wherein the input port and the output port are configured and positioned to deliver a sample to and from the internal compartment while the centrifuge chamber is rotating; wherein the centrifuge chamber comprises a detection window that extends radially in the bottom or top of the chamber from a position adjacent to the rotation axis to a position near the perimeter of the chamber; and wherein the sample processing unit further comprises a detector that is constructed and aligned to receive light passing through a sample in the detection window of the centrifuge chamber so as to assess a characteristic of the deposited sample radially through and along the detection window, thereby monitoring separation of the first component from the second component in the chamber; b) a sample separation unit coupled to the output port of the sample processing unit, the sample separation unit comprising: a separation column holder, a pump, a plurality of valves configured to at least partially control fluid flow through a fluid circuitry, and a separation column positioned in the holder, wherein the separation column is configured to separate labeled and unlabeled components of a sample flowed through the column; c) a processor; and d) a memory having instructions stored thereon that, when executed by the processor, cause the device to perform operations comprising: receiving a type of starting material from an operator; loading a bone marrow product onto the centrifuge chamber in stages; performing a buffy coat spin on each stage and adjusting a red blood cell pellet to fit the bone marrow product in a 45 ml volume; adjusting the product to a 70 ml cell suspension; performing a ficoll separation; harvesting mononuclear cells; and returning mononuclear cells to a cleaned chamber, the mononuclear cells having been washed, labeled, post-label washed, and CD34 selected.

Additional functions that can be executed by the device singly or in combination with other functions, in accordance with embodiments of the invention, include: depletion of CD33+ cells; washing and labeling of cultured T cells; wash processes made to particular specifications; wash and exchange into electroporation medium; selection of engineered T cells expressing CD19; concentration and wash processes made to particular specifications; wash and formulation processes made to particular specifications; ficoll separation and wash processes made to particular specifications; flexible centrifugation of cells during lentiviral transduction; CD4 enrichment from nonmobilized apheresis unit; CD14 enrichment from nonmobilized apheresis unit; harvest of cells cultured in chamber and cleaning of chamber with sterile water to remove unwanted adherent cells; elute off all cells from chamber without wash or media exchange; culture; TS730 installation and ficoll of apheresis material to set up T cell culture; media exchange and harvest of cultured T cells; modular program allowing for adjustments/additions to cultured T cells including retroviral transduction; washing of thawed cells to set up culture; protein incubation in specified volume; negatively select for gamma delta T cells using research Isolation Kit; negatively select for memory CD8 cells using research isolation kit; isolate either memory or naïve CD4 or CD8 cells using research isolation kit; isolate naive Pan T cells using research Isolation Kit; perform CD38 depletion with research kit prior to CD34 selection; flexible program to allow testing of various parameters related to retroviral transduction; specification allowing transfer and holding of materials from one bag position to another; Program used to demonstrate CD45 enrichment of leukocytes from mouse lung digest preps; manufacturing of cultured, expanded NK cells; ficoll of nonmobilized leukopak for subsequent NK culture; manufacturing of culture-derived gamma delta T cells; Hetastarch sedimentation, RBC reduction, washing and CD34 labeling of bone marrow; Hetastarch sedimentation, RBC reduction and lineage depletion of bone marrow products; Hetastarch sedimentation, RBC reduction, washing and CD34 labeling of bone marrow; original Hetastarch RBC reduction, washing and labeling on TS100, for processing on, for example, monkey marrow; 2-step labeling process for CD34 labeling monkey marrow; CD34 selection sequence for cells labeled using XXX2 program described above; lentiviral transduction of monkey CD34+ cells enriched using above program and cultured using culture program; culturing of CD34+ cells isolated by use of the XXX1-3 programs; clean tubing set of vector following transduction; formulation and harvest of cells processed with programs 1-5; and expansion of current CD8CD4 selection program to make compatible with performing 3 subset isolations in a single day from a single pack, Exemplary Computer System Useful for Implementing Various Embodiments Various embodiments can be implemented, for example, using one or more computer systems, such as computer system 1600 shown in FIG. 16. Computer system 1600 can be used, for example, to implement methods and functionality described above. Computer system 1600 can be any computer capable of performing the functions described herein.

Computer system 1600 can be any well-known computer capable of performing the functions described herein.

Computer system 1600 includes one or more processors (also called central processing units, or CPUs), such as a processor 1604. Processor 1604 is connected to a communication infrastructure or bus 1606.

One or more processors 1604 may each be a graphics processing unit (GPU). In an embodiment, a GPU is a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 1600 also includes user input/output device(s) 1603, such as monitors, keyboards, pointing devices, etc., that communicate with communication infrastructure 1606 through user input/output interface(s) 1602.

Computer system 1600 also includes a main or primary memory 1608, such as random access memory (RAM). Main memory 1608 may include one or more levels of cache. Main memory 1608 has stored therein control logic (i.e., computer software) and/or data.

Computer system 1600 may also include one or more secondary storage devices or memory 1610. Secondary memory 1610 may include, for example, a hard disk drive 1612 and/or a removable storage device or drive 1614. Removable storage drive 1614 may be a floppy disk drive, a magnetic tape drive, a compact disk drive, an optical storage device, tape backup device, and/or any other storage device/drive.

Removable storage drive 1614 may interact with a removable storage unit 1618. Removable storage unit 1618 includes a computer usable or readable storage device having stored thereon computer software (control logic) and/or data. Removable storage unit 1618 may be a floppy disk, magnetic tape, compact disk, DVD, optical storage disk, and/any other computer data storage device. Removable storage drive 1614 reads from and/or writes to removable storage unit 1618 in a well-known manner.

According to an exemplary embodiment, secondary memory 1610 may include other means, instrumentalities or other approaches for allowing computer programs and/or other instructions and/or data to be accessed by computer system 1600. Such means, instrumentalities or other approaches may include, for example, a removable storage unit 1622 and an interface 1620. Examples of the removable storage unit 1622 and the interface 1620 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 1600 may further include a communication or network interface 1624. Communication interface 1624 enables computer system 1600 to communicate and interact with any combination of remote devices, remote networks, remote entities, etc. (individually and collectively referenced by reference number 1628). For example, communication interface 1624 may allow computer system 1600 to communicate with remote devices 1628 over communications path 1626, which may be wired and/or wireless, and which may include any combination of LANs, WANs, the Internet, etc. Control logic and/or data may be transmitted to and from computer system 1600 via communication path 1626.

In an embodiment, a tangible, non-transitory apparatus or article of manufacture comprising a tangible, non-transitory computer useable or readable medium having control logic (software) stored thereon is also referred to herein as a computer program product or program storage device. This includes, but is not limited to, computer system 1600, main memory 1608, secondary memory 1610, and removable storage units 1618 and 1622, as well as tangible articles of manufacture embodying any combination of the foregoing. Such control logic, when executed by one or more data processing devices (such as computer system 1600), causes such data processing devices to operate as described herein.

Based on the teachings contained in this disclosure, it will be apparent to persons skilled in the relevant art(s) how to make and use embodiments of this disclosure using data processing devices, computer systems and/or computer architectures other than that shown in FIG. 16. In particular, embodiments can operate with software, hardware, and/or operating system implementations other than those described herein.

Conclusion

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure.

Each of the applications and patents cited in this text, as well as each document or reference cited in each of the applications and patents (including during the prosecution of each issued patent "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein. Those skilled in the art will recognize, or be able to ascertain using no more than routine experimentation, many equivalents to the embodiments of the invention described herein. Such equivalents are encompassed by the following claims.

What is claimed is:

1. One or more machine-readable storage devices having encoded thereon computer readable instructions for causing one or more processing devices to control operations of various portions of a closed system portable device that includes a treatment chamber, and a target cell selector configured to separate target cells in a subject sample from non-target cells in the subject sample, the operations comprising:
   transferring the subject sample from the treatment chamber to the target cell selector;
   controlling operation of the target cell selector to separate the target cells from the non-target cells;
   transferring the target cells back into the treatment chamber;
   introducing a cell modifying substance to the target cells within the treatment chamber or the target cell selector, wherein the surface of the chamber is coated with the cell modifying substance and wherein contact of the target cells with the cell modifying substance results in genetically-modified target cells; and
   generating a formulation including genetically-modified target cells, wherein the generating comprises controlling the treatment chamber to pellet the genetically-modified target cells and to remove supernatant material; controlling a flow of a carrier medium into the treatment chamber; and controlling a flow of the carrier medium out of the treatment chamber in accordance with a target volume of the formulation to generate the formulation, the formulation being adapted for administration to a subject; and
   wherein the one or more machine-readable storage devices having encoded thereon computer readable instructions causes one or more processing devices to control operations of various portions of the closed system portable device.

2. The one or more machine-readable storage devices of claim 1, wherein transferring the subject sample from the treatment chamber to a target cell selector comprises electronically controlling at least one valve and/or a pump configured to control fluid flow between the treatment chamber and the target cell selector.

3. The one or more machine-readable storage devices of claim 1, wherein transferring the target cells back into the treatment chamber comprises electronically controlling at least one valve and/or a pump configured to control fluid flow between a receptacle configured to hold the target cells, and the treatment chamber, the receptacle being coupled to the target cell selector to receive the target cells.

4. The one or more machine-readable storage devices of claim 1, wherein controlling the operation of the target cell selector comprises priming a magnetic activated cell sorting (MACS) column of the target cell selector using a buffer solution.

5. The one or more machine-readable storage devices of claim 4, wherein the priming is controlled by controlling at least one valve and/or a pump configured to control fluid flow between a buffer reservoir and the target cell selector.

6. The one or more machine-readable storage devices of claim 1, wherein controlling the operation of the target cell selector comprises controlling a rate at which the subject sample is transferred to a magnetic activated cell sorting (MACS) column of the target cell selector.

7. The one or more machine-readable storage devices of claim 6, wherein the non-target cells include CD4 cells.

8. The one or more machine-readable storage devices of claim 1, further comprising:
   introducing of a medium into the treatment chamber subsequent to transferring the target cells back into to the treatment chamber; and
   executing a motion of the treatment chamber to facilitate contact between the target cells and the medium.

9. The one or more machine-readable storage devices of claim 8, wherein the steps of introducing the medium and executing the motion of the treatment chamber is repeated at least once.

10. The one or more machine-readable storage devices of claim 1, wherein generating the formulation further comprises controlling a cell culture process performed on the genetically-modified target cells.

11. The one or more machine-readable storage devices of claim 10, wherein controlling the cell culture process comprises:
   determining one or more parameters associated with at least one gas usable in the cell culture process;
   determining a target temperature of the treatment chamber during the cell culture process;
   controlling temperature of the treatment chamber in accordance with the target temperature for a predetermined amount of time; and
   controlling flow of the at least one gas into the treatment chamber in accordance with the one or more parameters.

12. The one or more machine-readable storage devices of claim 1, further comprising presenting, on a display device, a user interface configured to accept one or more user-inputs pertaining to one or more of the operations.

13. The one or more machine-readable storage devices of claim 12, further comprising adjusting at least one of the operations in accordance with the one or more user-inputs.

14. The one or more machine-readable storage devices of claim 13, wherein the one or more user-inputs identify at least one of: the target cells, the non-target cells, and a volume of the formulation.

15. The one or more machine-readable storage devices of claim 1, wherein controlling the treatment chamber comprises:

receiving user-input indicative of a supernatant volume;

executing a centrifugal motion of the treatment chamber to pellet the genetically-modified target cells; and removing the supernatant material in accordance with the supernatant volume.

16. The one or more machine-readable storage devices of claim 1, further comprising instructions for removal of the formulation from the treatment chamber.

17. The one or more machine-readable storage devices of claim 1, wherein the subject sample is a non-mobilized apheresis product, and the target cells are CD8 cells.

18. The one or more machine-readable storage devices of claim 1, wherein the introducing comprises initiating viral vector transduction within the treatment chamber of the closed system.

19. The one or more machine-readable storage devices of claim 1, wherein the operations further comprise removing the formulation from the treatment chamber.

20. The one or more machine-readable storage devices of claim 1, wherein the cell modifying substance inducing genetic modification of the target cells is selected from the group consisting of: a virus, a viral particle, an adenovirus, a lentivirus, RNA, DNA, non-coding small or large RNAs, mRNA- or shRNA-expression plasmids, protein, ligand, receptor, cytokine, stimulating or deactivating antibody, pharmacological agent, and feeder cells.

21. One or more machine-readable storage devices having encoded thereon computer readable instructions for causing one or more processing devices to control operations of various portions of a closed system portable device that includes a treatment chamber, and a target cell selector configured to separate lymphocytes in a subject sample from non-lymphocytes in the subject sample, the operations comprising:

transferring the subject sample from the treatment chamber to the target cell selector;

controlling operation of the target cell selector to separate the lymphocytes from the non-lymphocytes;

transferring the lymphocytes back into the treatment chamber;

introducing a genetic modifier to the lymphocytes within the treatment chamber or the target cell selector; and generating a formulation including genetically-modified lymphocytes, wherein the generating comprises controlling the treatment chamber to pellet the genetically-modified lymphocytes and to remove supernatant material; controlling a flow of a carrier medium into the treatment chamber; and controlling a flow of the carrier medium out of the treatment chamber in accordance with a target volume of the formulation to generate the formulation, the formulation being adapted for administration to a subject; and wherein the one or more machine-readable storage devices having encoded thereon computer readable instructions causes one or more processing devices to control operations of various portions of the closed system portable device.

* * * * *

UNITED STATES PATENT AND TRADEMARK OFFICE
CERTIFICATE OF CORRECTION

PATENT NO. : 11,339,407 B2
APPLICATION NO. : 15/663702
DATED : May 24, 2022
INVENTOR(S) : Timothy Wayne Waters, Stefan Miltenyi and Alexander Scheffold It is certified that error appears in the above-identified patent and that said Letters Patent is hereby corrected as shown below:

On the Title Page

In item (72), 2nd. Inventor's City & Country, Column 1, Line 1, delete "Bergish Gladbach (DE)" and insert -- Bergisch Gladbach (DE) --.

In Other Publications, Column 2, Lines 2-3, delete "Tranfusion," and insert -- Transfusion, --.

Signed and Sealed this
Twenty-fifth Day of October, 2022

Katherine Kelly Vidal
*Director of the United States Patent and Trademark Office*